United States Patent
Clark

(10) Patent No.: US 9,585,647 B2
(45) Date of Patent: Mar. 7, 2017

(54) MEDICAL DEVICE FOR REPAIRING A FISTULA

(71) Applicant: Abbott Laboratories, Abbott Park, IL (US)

(72) Inventor: Ian J. Clark, West Bloomfield, MI (US)

(73) Assignee: ABBOTT LABORATORIES, Abbott Park, IL (US)

(*) Notice: Subject to any disclaimer, the term of this patent is extended or adjusted under 35 U.S.C. 154(b) by 0 days.

(21) Appl. No.: 14/539,830

(22) Filed: Nov. 12, 2014

(65) Prior Publication Data

US 2015/0073471 A1 Mar. 12, 2015

Related U.S. Application Data

(62) Division of application No. 12/548,274, filed on Aug. 26, 2009, now abandoned.

(51) Int. Cl.
*A61B 17/00* (2006.01)

(52) U.S. Cl.
CPC *A61B 17/0057* (2013.01); *A61B 2017/00584* (2013.01); *A61B 2017/00641* (2013.01);
(Continued)

(58) Field of Classification Search
CPC ...... A61B 17/0644; A61B 2017/00584; A61B 2017/00592; A61B 2017/00668;
(Continued)

(56) References Cited

U.S. PATENT DOCUMENTS

| 287,046 A | 10/1883 | Norton |
| 438,400 A | 10/1890 | Brennen |

(Continued)

FOREIGN PATENT DOCUMENTS

| AU | 2003297432 | 7/2004 |
| CA | 2 339 060 | 2/2000 |

(Continued)

OTHER PUBLICATIONS

U.S. Appl. No. 09/610,128, filed Jul. 5, 2000, Kerievsky.
(Continued)

*Primary Examiner* — Alexander Orkin
(74) *Attorney, Agent, or Firm* — Workman Nydegger; Randy Shen

(57) ABSTRACT

A closure element applying medical device for repairing a fistula is described. The closure element applying medical device can be configured for repairing any type of fistula that provides an abnormal channel from one body part to another body part (e.g., organ to organ, organ to vessel, and/or vessel to vessel). Examples of fistulas that can be repaired with the present invention include anorectal fistulas, enteroenteral fistulas, enterocutaneous fistulas, vesicovaginal fistulas, arteriovenous fistulas, perilymph fistulas, rectovaginal fistulas, ureterocolon fistulas, and the like. The medical device can include a closure element, a shaft, a carrier assembly, and controller systems. The medical device can also include a locator assembly. Additionally, the closure element applying medical device can include endoscope components so as to function also as an endoscope.

17 Claims, 23 Drawing Sheets

(52) U.S. Cl.
CPC ............ *A61B 2017/00663* (2013.01); *A61B 2017/00668* (2013.01)

(58) Field of Classification Search
CPC .... A61B 2017/0649; A61B 2017/0647; A61B 17/0057; A61B 2017/0645
See application file for complete search history.

(56) References Cited

U.S. PATENT DOCUMENTS

| | | |
|---|---|---|
| 556,082 A | 3/1896 | Boeddinghaus |
| 1,088,393 A | 2/1914 | Backus |
| 1,123,290 A | 1/1915 | Von Herff |
| 1,331,401 A | 2/1920 | Summers |
| 1,596,004 A | 8/1926 | De Bengoa |
| 1,647,958 A | 11/1927 | Ciarlante |
| 1,880,569 A | 10/1932 | Weis |
| 2,087,074 A | 7/1937 | Tucker |
| 2,210,061 A | 8/1940 | Caminez |
| 2,254,620 A | 9/1941 | Miller |
| 2,316,297 A | 4/1943 | Southerland et al. |
| 2,371,978 A | 3/1945 | Perham |
| 2,453,227 A | 11/1948 | James |
| 2,583,625 A | 1/1952 | Bergan |
| 2,684,070 A | 7/1954 | Kelsey |
| 2,755,699 A | 7/1956 | Forster |
| 2,910,067 A | 10/1959 | White |
| 2,944,311 A | 7/1960 | Schneckenberger |
| 2,951,482 A | 9/1960 | Sullivan |
| 2,969,887 A | 1/1961 | Darmstadt et al. |
| 3,015,403 A | 1/1962 | Fuller |
| 3,113,379 A | 12/1963 | Frank |
| 3,120,230 A | 2/1964 | Skold |
| 3,142,878 A | 8/1964 | Santora |
| 3,209,754 A | 10/1965 | Brown |
| 3,482,428 A | 12/1969 | Kapitanov et al. |
| 3,494,533 A | 2/1970 | Green et al. |
| 3,510,923 A | 5/1970 | Blake |
| 3,523,351 A | 8/1970 | Filia |
| 3,586,002 A | 6/1971 | Wood et al. |
| 3,604,425 A | 9/1971 | Le Roy |
| 3,618,447 A | 11/1971 | Goins |
| 3,677,243 A | 7/1972 | Nerz |
| 3,757,629 A | 9/1973 | Schneider |
| 3,805,337 A | 4/1974 | Branstetter |
| 3,823,719 A | 7/1974 | Cummings |
| 3,828,791 A | 8/1974 | Santos |
| 3,856,016 A | 12/1974 | Davis |
| 3,874,388 A | 4/1975 | King et al. |
| 3,908,662 A | 9/1975 | Razgulov et al. |
| 3,926,194 A | 12/1975 | Greenberg et al. |
| 3,939,820 A | 2/1976 | Grayzel |
| 3,944,114 A | 3/1976 | Coppens |
| 3,960,147 A | 6/1976 | Murray |
| 3,985,138 A | 10/1976 | Jarvik |
| 4,007,743 A | 2/1977 | Blake |
| 4,014,492 A | 3/1977 | Rothfuss |
| 4,018,228 A | 4/1977 | Goosen |
| 4,047,533 A | 9/1977 | Perciaccante et al. |
| 4,064,881 A | 12/1977 | Meredith |
| 4,112,944 A | 9/1978 | Williams |
| 4,153,321 A | 5/1979 | Pombrol |
| 4,162,673 A | 7/1979 | Patel |
| 4,169,476 A | 10/1979 | Hiltebrandt |
| 4,192,315 A | 3/1980 | Hilzinger et al. |
| 4,201,215 A | 5/1980 | Crossett et al. |
| 4,204,541 A | 5/1980 | Kapitanov |
| 4,207,870 A | 6/1980 | Eldridge |
| 4,214,587 A | 7/1980 | Sakura, Jr. |
| 4,215,699 A | 8/1980 | Patel |
| 4,217,902 A | 8/1980 | March |
| 4,273,129 A | 6/1981 | Boebel |
| 4,274,415 A | 6/1981 | Kanamoto et al. |
| 4,278,091 A | 7/1981 | Borzone |
| 4,317,445 A | 3/1982 | Robinson |
| 4,317,451 A | 3/1982 | Cerwin et al. |
| 4,318,401 A | 3/1982 | Zimmerman |
| 4,327,485 A | 5/1982 | Rix |
| 4,345,606 A | 8/1982 | Littleford |
| 4,359,052 A | 11/1982 | Staub |
| 4,368,736 A | 1/1983 | Kaster |
| 4,396,139 A | 8/1983 | Hall et al. |
| 4,407,286 A | 10/1983 | Noiles et al. |
| 4,411,654 A | 10/1983 | Boarini et al. |
| 4,412,832 A | 11/1983 | Kling et al. |
| 4,428,376 A | 1/1984 | Mericle |
| 4,440,170 A | 4/1984 | Golden et al. |
| 4,449,531 A | 5/1984 | Cerwin et al. |
| 4,475,544 A | 10/1984 | Reis |
| 4,480,356 A | 11/1984 | Martin |
| 4,485,816 A | 12/1984 | Krumme |
| RE31,855 E | 3/1985 | Osborne |
| 4,505,273 A | 3/1985 | Braun et al. |
| 4,505,274 A | 3/1985 | Speelman |
| 4,523,591 A | 6/1985 | Kaplan et al. |
| 4,523,695 A | 6/1985 | Braun et al. |
| 4,525,157 A | 6/1985 | Valaincourt |
| 4,526,174 A | 7/1985 | Froehlich |
| 4,570,633 A | 2/1986 | Golden |
| 4,586,503 A | 5/1986 | Kirsch et al. |
| 4,592,498 A | 6/1986 | Braun et al. |
| 4,596,559 A | 6/1986 | Fleischhacker |
| 4,607,638 A | 8/1986 | Crainich |
| 4,610,251 A | 9/1986 | Kumar |
| 4,610,252 A | 9/1986 | Catalano |
| 4,635,634 A | 1/1987 | Santos |
| 4,635,637 A | 1/1987 | Schreiber |
| 4,644,956 A | 2/1987 | Morgenstern |
| 4,651,737 A | 3/1987 | Deniega |
| 4,664,305 A | 5/1987 | Blake, III et al. |
| 4,665,906 A | 5/1987 | Jervis |
| 4,687,469 A | 8/1987 | Osypka |
| 4,693,249 A | 9/1987 | Schenck et al. |
| 4,719,917 A | 1/1988 | Barrows et al. |
| 4,724,840 A | 2/1988 | McVay et al. |
| 4,738,658 A | 4/1988 | Magro et al. |
| 4,744,364 A | 5/1988 | Kensey |
| 4,747,407 A | 5/1988 | Liu et al. |
| 4,759,364 A | 7/1988 | Boebel |
| 4,771,782 A | 9/1988 | Millar |
| 4,772,266 A | 9/1988 | Groshong |
| 4,777,950 A | 10/1988 | Kees, Jr. |
| 4,789,090 A | 12/1988 | Blake, III |
| 4,832,688 A | 5/1989 | Sagae et al. |
| 4,836,204 A | 6/1989 | Landymore et al. |
| 4,852,568 A | 8/1989 | Kensey |
| 4,860,746 A | 8/1989 | Yoon |
| 4,865,026 A | 9/1989 | Barrett |
| 4,874,122 A | 10/1989 | Froelich et al. |
| 4,878,915 A | 11/1989 | Brantigan |
| 4,885,003 A | 12/1989 | Hillstead |
| 4,886,067 A | 12/1989 | Palermo |
| 4,887,601 A | 12/1989 | Richards |
| 4,890,612 A | 1/1990 | Kensey |
| 4,900,303 A | 2/1990 | Lemelson |
| 4,902,508 A | 2/1990 | Badylak et al. |
| 4,917,087 A | 4/1990 | Walsh et al. |
| 4,917,089 A | 4/1990 | Sideris |
| 4,929,240 A | 5/1990 | Kirsch et al. |
| 4,934,364 A | 6/1990 | Green |
| 4,950,258 A | 8/1990 | Kawai et al. |
| 4,957,499 A | 9/1990 | Lipatov et al. |
| 4,961,729 A | 10/1990 | Vaillancourt |
| 4,967,949 A | 11/1990 | Sandhaus |
| 4,976,721 A | 12/1990 | Blasnik et al. |
| 4,983,176 A | 1/1991 | Cushman et al. |
| 4,997,436 A | 3/1991 | Oberlander |
| 4,997,439 A | 3/1991 | Chen |
| 5,002,562 A | 3/1991 | Oberlander |
| 5,007,921 A | 4/1991 | Brown |
| 5,011,487 A | 4/1991 | Shichman |
| 5,015,247 A | 5/1991 | Michelson |
| 5,021,059 A | 6/1991 | Kensey et al. |
| 5,026,390 A | 6/1991 | Brown |
| 5,030,226 A | 7/1991 | Green et al. |

(56) References Cited

U.S. PATENT DOCUMENTS

| | | |
|---|---|---|
| 5,032,127 A | 7/1991 | Frazee et al. |
| 5,035,692 A | 7/1991 | Lyon et al. |
| 5,041,129 A | 8/1991 | Hayhurst et al. |
| 5,042,707 A | 8/1991 | Taheri |
| 5,047,047 A | 9/1991 | Yoon |
| 5,053,008 A | 10/1991 | Bajaj |
| 5,059,201 A | 10/1991 | Asnis |
| 5,061,274 A | 10/1991 | Kensey |
| 5,061,283 A | 10/1991 | Silvestrini |
| 5,078,731 A | 1/1992 | Hayhurst |
| 5,092,941 A | 3/1992 | Miura |
| 5,100,418 A | 3/1992 | Yoon et al. |
| 5,100,422 A | 3/1992 | Berguer et al. |
| 5,108,420 A | 4/1992 | Marks |
| 5,108,421 A | 4/1992 | Fowler |
| 5,114,032 A | 5/1992 | Laidlaw |
| 5,114,065 A | 5/1992 | Storace |
| 5,116,349 A | 5/1992 | Aranyi |
| 5,122,122 A | 6/1992 | Allgood |
| 5,122,156 A | 6/1992 | Granger et al. |
| 5,131,379 A | 7/1992 | Sewell, Jr. |
| 5,141,520 A | 8/1992 | Goble et al. |
| 5,147,381 A | 9/1992 | Heimerl et al. |
| 5,156,609 A | 10/1992 | Nakao et al. |
| 5,163,343 A | 11/1992 | Gish |
| 5,167,634 A | 12/1992 | Corrigan, Jr. et al. |
| 5,167,643 A | 12/1992 | Lynn |
| 5,171,249 A | 12/1992 | Stefanchik et al. |
| 5,171,250 A | 12/1992 | Yoon |
| 5,171,259 A | 12/1992 | Inoue |
| 5,176,648 A | 1/1993 | Holmes et al. |
| 5,192,288 A | 3/1993 | Thompson et al. |
| 5,192,300 A | 3/1993 | Fowler |
| 5,192,301 A | 3/1993 | Kamiya et al. |
| 5,192,302 A | 3/1993 | Kensey et al. |
| 5,192,602 A | 3/1993 | Spencer et al. |
| 5,193,533 A | 3/1993 | Body et al. |
| 5,197,971 A | 3/1993 | Bonutti |
| 5,207,697 A | 5/1993 | Carusillo et al. |
| 5,209,756 A | 5/1993 | Seedhorm et al. |
| 5,217,024 A | 6/1993 | Dorsey et al. |
| 5,222,974 A | 6/1993 | Kensey et al. |
| 5,226,908 A | 7/1993 | Yoon |
| 5,236,435 A | 8/1993 | Sewell, Jr. |
| 5,242,456 A | 9/1993 | Nash et al. |
| 5,242,457 A | 9/1993 | Akopov et al. |
| 5,242,459 A | 9/1993 | Buelna |
| 5,243,857 A | 9/1993 | Velez |
| 5,246,156 A | 9/1993 | Rothfuss et al. |
| 5,246,443 A | 9/1993 | Mai |
| 5,250,058 A | 10/1993 | Miller et al. |
| 5,254,105 A | 10/1993 | Haaga |
| 5,255,679 A | 10/1993 | Imran |
| 5,269,792 A | 12/1993 | Kovac et al. |
| 5,275,616 A | 1/1994 | Fowler |
| 5,281,422 A | 1/1994 | Badylak et al. |
| 5,282,808 A | 2/1994 | Kovac et al. |
| 5,282,827 A | 2/1994 | Kensey et al. |
| 5,284,488 A | 2/1994 | Sideris |
| 5,289,963 A | 3/1994 | McGarry et al. |
| 5,290,243 A | 3/1994 | Chodorow et al. |
| 5,290,310 A | 3/1994 | Makower et al. |
| 5,292,309 A | 3/1994 | Van Tassel et al. |
| 5,292,332 A | 3/1994 | Lee |
| 5,304,183 A | 4/1994 | Gourlay et al. |
| 5,304,184 A | 4/1994 | Hathaway et al. |
| 5,304,204 A | 4/1994 | Bregen |
| 5,306,254 A | 4/1994 | Nash et al. |
| 5,309,927 A | 5/1994 | Welch |
| 5,318,542 A | 6/1994 | Hirsch et al. |
| 5,320,639 A | 6/1994 | Rudnick |
| 5,322,694 A | 6/1994 | Sixsmith |
| 5,327,908 A | 7/1994 | Gerry |
| 5,330,445 A | 7/1994 | Haaga |
| 5,330,503 A | 7/1994 | Yoon |
| 5,334,216 A | 8/1994 | Vidal et al. |
| 5,334,217 A | 8/1994 | Das |
| 5,335,680 A | 8/1994 | Moore |
| 5,340,360 A | 8/1994 | Stefanchik |
| 5,342,393 A | 8/1994 | Stack |
| 5,344,439 A | 9/1994 | Otten |
| 5,350,399 A | 9/1994 | Erlebacher et al. |
| 5,352,229 A | 10/1994 | Goble et al. |
| 5,354,279 A | 10/1994 | Hofling |
| 5,364,406 A | 11/1994 | Sewell, Jr. |
| 5,364,408 A | 11/1994 | Gordon |
| 5,366,458 A | 11/1994 | Korthoff et al. |
| 5,366,479 A | 11/1994 | McGarry et al. |
| 5,383,896 A | 1/1995 | Gershony et al. |
| 5,383,897 A | 1/1995 | Wholey |
| RE34,866 E | 2/1995 | Kensey et al. |
| 5,392,978 A | 2/1995 | Velez et al. |
| 5,395,030 A | 3/1995 | Kuramoto et al. |
| 5,411,520 A | 5/1995 | Nash et al. |
| 5,413,571 A | 5/1995 | Katsaros et al. |
| 5,413,584 A | 5/1995 | Schulze |
| 5,416,584 A | 5/1995 | Kay |
| 5,417,699 A | 5/1995 | Klein et al. |
| 5,419,765 A | 5/1995 | Weldon et al. |
| 5,419,777 A | 5/1995 | Hofling |
| 5,421,832 A | 6/1995 | Lefebvre |
| 5,423,857 A | 6/1995 | Rosenman et al. |
| 5,425,489 A | 6/1995 | Shichman et al. |
| 5,425,740 A | 6/1995 | Hutchinson, Jr. |
| 5,431,639 A | 7/1995 | Shaw |
| 5,431,667 A | 7/1995 | Thompson et al. |
| 5,433,721 A | 7/1995 | Hooven et al. |
| 5,437,631 A | 8/1995 | Janzen |
| 5,439,479 A | 8/1995 | Shichman et al. |
| 5,443,477 A | 8/1995 | Marin et al. |
| 5,443,481 A | 8/1995 | Lee |
| 5,445,167 A | 8/1995 | Yoon et al. |
| 5,449,359 A | 9/1995 | Groiso |
| 5,451,235 A | 9/1995 | Lock et al. |
| 5,456,400 A | 10/1995 | Shichman et al. |
| 5,462,561 A | 10/1995 | Voda |
| 5,464,413 A | 11/1995 | Siska, Jr. et al. |
| 5,464,416 A | 11/1995 | Steckel |
| 5,466,241 A | 11/1995 | Leroy et al. |
| 5,470,010 A | 11/1995 | Rothfuss et al. |
| 5,471,982 A | 12/1995 | Edwards et al. |
| 5,474,557 A | 12/1995 | Mai |
| 5,474,569 A | 12/1995 | Zinreich et al. |
| 5,476,505 A | 12/1995 | Limon |
| 5,478,352 A | 12/1995 | Fowler |
| 5,478,353 A | 12/1995 | Yoon |
| 5,478,354 A | 12/1995 | Tovey et al. |
| 5,484,420 A | 1/1996 | Russo |
| 5,486,195 A | 1/1996 | Myers et al. |
| 5,496,332 A | 3/1996 | Sierra et al. |
| 5,497,933 A | 3/1996 | DeFonzo et al. |
| 5,507,744 A | 4/1996 | Tay et al. |
| 5,507,755 A | 4/1996 | Gresl et al. |
| 5,510,115 A | 4/1996 | Breillatt, Jr. et al. |
| 5,522,840 A | 6/1996 | Krajicek |
| 5,527,322 A | 6/1996 | Klein et al. |
| 5,536,251 A | 7/1996 | Evard et al. |
| 5,540,712 A | 7/1996 | Kleshinski et al. |
| 5,540,716 A | 7/1996 | Hlavacek |
| 5,544,802 A | 8/1996 | Crainich |
| 5,545,178 A | 8/1996 | Kensey et al. |
| 5,547,474 A | 8/1996 | Kloeckl et al. |
| 5,560,532 A | 10/1996 | DeFonzo et al. |
| 5,571,120 A | 11/1996 | Yoon |
| 5,573,784 A | 11/1996 | Badylak et al. |
| 5,575,771 A | 11/1996 | Walinsky |
| 5,582,616 A | 12/1996 | Bolduc et al. |
| 5,584,879 A | 12/1996 | Reimold et al. |
| 5,591,205 A | 1/1997 | Fowler |
| 5,593,412 A | 1/1997 | Martinez et al. |
| 5,601,602 A | 2/1997 | Fowler |
| 5,609,597 A | 3/1997 | Lehrer |
| 5,613,974 A | 3/1997 | Andreas et al. |
| 5,618,291 A | 4/1997 | Thompson et al. |

(56) References Cited

U.S. PATENT DOCUMENTS

| | | |
|---|---|---|
| 5,620,452 A | 4/1997 | Yoon |
| 5,620,461 A | 4/1997 | Muijs et al. |
| 5,626,614 A | 5/1997 | Hart |
| 5,634,936 A | 6/1997 | Linden et al. |
| 5,643,318 A | 7/1997 | Tsukernik et al. |
| 5,645,565 A | 7/1997 | Rudd et al. |
| 5,645,566 A | 7/1997 | Brenneman et al. |
| 5,645,567 A | 7/1997 | Crainich |
| 5,649,959 A | 7/1997 | Hannam et al. |
| D383,539 S | 9/1997 | Croley |
| 5,674,231 A | 10/1997 | Green et al. |
| 5,676,689 A | 10/1997 | Kensey et al. |
| 5,676,974 A | 10/1997 | Valdes et al. |
| 5,681,280 A | 10/1997 | Rusk et al. |
| 5,681,334 A | 10/1997 | Evans et al. |
| 5,683,405 A | 11/1997 | Yacoubian et al. |
| 5,690,674 A | 11/1997 | Diaz |
| 5,695,504 A | 12/1997 | Gifford, III et al. |
| 5,695,505 A | 12/1997 | Yoon |
| 5,695,524 A | 12/1997 | Kelley et al. |
| 5,697,943 A | 12/1997 | Sauer et al. |
| 5,700,273 A | 12/1997 | Buelna et al. |
| 5,709,224 A | 1/1998 | Behl et al. |
| 5,715,987 A | 2/1998 | Kelley et al. |
| 5,716,375 A | 2/1998 | Fowler |
| 5,720,755 A | 2/1998 | Dakov |
| 5,725,498 A | 3/1998 | Janzen et al. |
| 5,725,552 A | 3/1998 | Kotula et al. |
| 5,725,554 A | 3/1998 | Simon et al. |
| 5,728,110 A | 3/1998 | Vidal et al. |
| 5,728,114 A | 3/1998 | Evans et al. |
| 5,728,116 A | 3/1998 | Rosenman |
| 5,728,122 A | 3/1998 | Leschinsky et al. |
| 5,728,132 A | 3/1998 | Van Tassel et al. |
| 5,728,133 A | 3/1998 | Kontos |
| 5,732,872 A | 3/1998 | Bolduc et al. |
| 5,735,873 A | 4/1998 | MacLean |
| 5,749,826 A | 5/1998 | Faulkner |
| 5,752,966 A | 5/1998 | Chang |
| 5,755,726 A | 5/1998 | Pratt et al. |
| 5,755,727 A | 5/1998 | Kontos |
| 5,755,778 A | 5/1998 | Kleshinski |
| 5,766,217 A | 6/1998 | Christy |
| 5,766,246 A | 6/1998 | Mulhauser et al. |
| 5,769,870 A | 6/1998 | Salahieh et al. |
| 5,776,147 A | 7/1998 | Dolendo |
| 5,779,707 A | 7/1998 | Bertholet et al. |
| 5,780,807 A | 7/1998 | Saunders |
| 5,782,844 A | 7/1998 | Yoon et al. |
| 5,782,860 A | 7/1998 | Epstein et al. |
| 5,782,861 A | 7/1998 | Cragg et al. |
| 5,795,958 A | 8/1998 | Rao et al. |
| 5,797,928 A | 8/1998 | Kogasaka |
| 5,797,931 A | 8/1998 | Bito et al. |
| 5,797,933 A | 8/1998 | Snow et al. |
| 5,797,958 A | 8/1998 | Yoon |
| 5,797,960 A | 8/1998 | Stevens et al. |
| 5,810,776 A | 9/1998 | Bacich et al. |
| 5,810,846 A | 9/1998 | Virnich et al. |
| 5,810,851 A | 9/1998 | Yoon |
| 5,817,113 A | 10/1998 | Gifford, III et al. |
| 5,820,631 A | 10/1998 | Nobles |
| 5,827,298 A | 10/1998 | Hart et al. |
| 5,830,125 A | 11/1998 | Scribner et al. |
| 5,830,217 A | 11/1998 | Ryan |
| 5,830,221 A | 11/1998 | Stein et al. |
| 5,833,698 A | 11/1998 | Hinchliffe et al. |
| 5,843,164 A | 12/1998 | Frantzen et al. |
| 5,843,167 A | 12/1998 | Dwyer et al. |
| 5,853,421 A | 12/1998 | Leschinsky et al. |
| 5,853,422 A | 12/1998 | Huebsch et al. |
| 5,855,312 A | 1/1999 | Toledano |
| 5,858,082 A | 1/1999 | Cruz et al. |
| 5,860,991 A | 1/1999 | Klein et al. |
| 5,861,003 A | 1/1999 | Latson et al. |
| 5,861,005 A | 1/1999 | Kontos |
| 5,861,043 A | 1/1999 | Carn |
| 5,865,791 A * | 2/1999 | Whayne et al. ............... 604/500 |
| 5,868,755 A | 2/1999 | Kanner et al. |
| 5,868,762 A | 2/1999 | Cragg et al. |
| 5,868,763 A | 2/1999 | Spence et al. |
| 5,871,474 A | 2/1999 | Hermann et al. |
| 5,871,501 A | 2/1999 | Leschinsky et al. |
| 5,871,525 A | 2/1999 | Edwards et al. |
| 5,873,876 A | 2/1999 | Christy |
| 5,873,891 A | 2/1999 | Sohn |
| 5,879,366 A | 3/1999 | Shaw et al. |
| 5,891,088 A | 4/1999 | Thompson et al. |
| 5,897,487 A | 4/1999 | Ouchi |
| 5,902,310 A | 5/1999 | Foerster et al. |
| 5,904,696 A | 5/1999 | Rosenman |
| 5,904,697 A | 5/1999 | Gifford, III et al. |
| 5,904,703 A | 5/1999 | Gilson |
| 5,906,631 A | 5/1999 | Imran |
| 5,907,893 A | 6/1999 | Zadno-Azizi et al. |
| 5,908,149 A | 6/1999 | Welch et al. |
| 5,910,155 A | 6/1999 | Ratcliff et al. |
| 5,919,207 A | 7/1999 | Taheri |
| 5,922,009 A | 7/1999 | Epstein et al. |
| 5,928,231 A | 7/1999 | Klein et al. |
| 5,928,251 A | 7/1999 | Aranyi et al. |
| 5,928,260 A | 7/1999 | Chin et al. |
| 5,935,147 A | 8/1999 | Kensey et al. |
| 5,938,667 A | 8/1999 | Peyser et al. |
| 5,941,890 A | 8/1999 | Voegele et al. |
| 5,947,999 A | 9/1999 | Groiso |
| 5,948,001 A | 9/1999 | Larsen |
| 5,951,518 A | 9/1999 | Licata et al. |
| 5,951,575 A | 9/1999 | Bolduc et al. |
| 5,951,576 A | 9/1999 | Wakabayashi |
| 5,951,589 A | 9/1999 | Epstein et al. |
| 5,954,732 A | 9/1999 | Hart et al. |
| 5,957,900 A | 9/1999 | Ouchi |
| 5,957,936 A | 9/1999 | Yoon et al. |
| 5,957,938 A | 9/1999 | Zhu et al. |
| 5,957,940 A | 9/1999 | Tanner et al. |
| 5,964,782 A | 10/1999 | Lafontaine et al. |
| 5,972,023 A | 10/1999 | Tanner et al. |
| 5,972,034 A | 10/1999 | Hofmann et al. |
| 5,976,161 A | 11/1999 | Kirsch et al. |
| 5,976,174 A | 11/1999 | Ruiz |
| 5,984,934 A | 11/1999 | Ashby et al. |
| 5,984,948 A | 11/1999 | Hasson |
| 5,984,949 A | 11/1999 | Levin |
| 5,993,468 A | 11/1999 | Rygaard |
| 5,993,476 A | 11/1999 | Groiso |
| 6,001,110 A | 12/1999 | Adams |
| 6,004,341 A | 12/1999 | Zhu et al. |
| 6,007,563 A | 12/1999 | Nash et al. |
| 6,007,574 A | 12/1999 | Pulnev et al. |
| 6,010,517 A | 1/2000 | Baccaro |
| 6,013,084 A | 1/2000 | Ken et al. |
| 6,015,815 A | 1/2000 | Mollison |
| 6,019,779 A | 2/2000 | Thorud et al. |
| 6,022,372 A | 2/2000 | Kontos |
| 6,024,750 A | 2/2000 | Mastri |
| 6,024,756 A | 2/2000 | Huebsch et al. |
| 6,030,364 A | 2/2000 | Durgin et al. |
| 6,030,413 A | 2/2000 | Lazarus |
| 6,033,427 A | 3/2000 | Lee |
| 6,036,703 A | 3/2000 | Evans et al. |
| 6,036,720 A | 3/2000 | Abrams et al. |
| 6,045,570 A | 4/2000 | Epstein et al. |
| 6,048,358 A | 4/2000 | Barak |
| 6,056,768 A | 5/2000 | Cates et al. |
| 6,056,769 A | 5/2000 | Epstein et al. |
| 6,056,770 A | 5/2000 | Epstein et al. |
| 6,059,800 A | 5/2000 | Hart et al. |
| 6,059,825 A | 5/2000 | Hobbs et al. |
| 6,063,085 A | 5/2000 | Tay et al. |
| 6,063,114 A | 5/2000 | Nash et al. |
| 6,071,300 A | 6/2000 | Brenneman et al. |
| 6,074,395 A | 6/2000 | Trott et al. |
| 6,077,281 A | 6/2000 | Das |

(56) References Cited

U.S. PATENT DOCUMENTS

| | | |
|---|---|---|
| 6,077,291 A | 6/2000 | Das |
| 6,080,182 A | 6/2000 | Shaw et al. |
| 6,080,183 A | 6/2000 | Tsugita et al. |
| 6,090,130 A | 7/2000 | Nash et al. |
| 6,102,271 A | 8/2000 | Longo et al. |
| 6,110,184 A | 8/2000 | Weadock |
| 6,113,610 A | 9/2000 | Poncet |
| 6,113,611 A * | 9/2000 | Allen et al. .................. 606/151 |
| 6,113,612 A | 9/2000 | Swanson et al. |
| 6,117,125 A | 9/2000 | Rothbarth et al. |
| 6,117,144 A | 9/2000 | Nobles et al. |
| 6,117,148 A | 9/2000 | Ravo |
| 6,117,157 A | 9/2000 | Tekulve |
| 6,117,159 A | 9/2000 | Huebsch et al. |
| 6,120,524 A | 9/2000 | Taheri |
| 6,126,675 A | 10/2000 | Shchervinsky et al. |
| 6,136,010 A | 10/2000 | Modesitt et al. |
| 6,146,385 A | 11/2000 | Torrie et al. |
| 6,149,660 A | 11/2000 | Laufer et al. |
| 6,149,667 A | 11/2000 | Hovland et al. |
| 6,152,144 A | 11/2000 | Lesh et al. |
| 6,152,936 A | 11/2000 | Christy et al. |
| 6,152,937 A | 11/2000 | Peterson et al. |
| 6,165,204 A | 12/2000 | Levinson et al. |
| 6,171,277 B1 | 1/2001 | Ponzi |
| 6,171,329 B1 | 1/2001 | Shaw et al. |
| 6,174,322 B1 | 1/2001 | Schneidt |
| 6,179,849 B1 | 1/2001 | Yencho et al. |
| 6,179,860 B1 | 1/2001 | Fulton, III et al. |
| 6,183,775 B1 | 2/2001 | Ventouras |
| 6,193,708 B1 | 2/2001 | Ken et al. |
| 6,193,734 B1 | 2/2001 | Bolduc et al. |
| 6,197,042 B1 | 3/2001 | Ginn et al. |
| 6,198,974 B1 | 3/2001 | Webster, Jr. |
| 6,200,329 B1 | 3/2001 | Fung et al. |
| 6,200,330 B1 | 3/2001 | Benderev et al. |
| 6,206,895 B1 | 3/2001 | Levinson |
| 6,206,913 B1 | 3/2001 | Yencho et al. |
| 6,206,931 B1 | 3/2001 | Cook et al. |
| 6,210,407 B1 | 4/2001 | Webster |
| 6,210,418 B1 | 4/2001 | Storz et al. |
| 6,217,554 B1 | 4/2001 | Green |
| 6,220,248 B1 | 4/2001 | Voegele et al. |
| 6,221,102 B1 | 4/2001 | Baker et al. |
| 6,231,561 B1 | 5/2001 | Frazier et al. |
| 6,238,705 B1 | 5/2001 | Liu et al. |
| 6,241,740 B1 | 6/2001 | Davis et al. |
| 6,245,079 B1 | 6/2001 | Nobles et al. |
| 6,248,124 B1 | 6/2001 | Pedros et al. |
| 6,254,617 B1 | 7/2001 | Spence et al. |
| 6,254,642 B1 | 7/2001 | Taylor |
| 6,258,115 B1 | 7/2001 | Dubrul |
| 6,261,309 B1 | 7/2001 | Urbanski |
| 6,267,773 B1 | 7/2001 | Gadberry et al. |
| 6,273,903 B1 | 8/2001 | Wilk |
| 6,277,140 B2 | 8/2001 | Ginn et al. |
| 6,280,460 B1 | 8/2001 | Bolduc et al. |
| 6,287,322 B1 | 9/2001 | Zhu et al. |
| 6,287,335 B1 | 9/2001 | Drasler et al. |
| 6,290,674 B1 | 9/2001 | Roue et al. |
| 6,296,657 B1 | 10/2001 | Brucker |
| 6,302,870 B1 | 10/2001 | Jacobsen et al. |
| 6,302,898 B1 | 10/2001 | Edwards et al. |
| 6,305,891 B1 | 10/2001 | Burlingame |
| 6,309,416 B1 | 10/2001 | Swanson et al. |
| 6,319,258 B1 | 11/2001 | McAllen, III et al. |
| 6,322,580 B1 | 11/2001 | Kanner |
| 6,328,727 B1 | 12/2001 | Frazier et al. |
| 6,329,386 B1 | 12/2001 | Mollison |
| 6,334,865 B1 | 1/2002 | Redmond et al. |
| 6,348,064 B1 | 2/2002 | Kanner |
| 6,355,052 B1 | 3/2002 | Neuss et al. |
| 6,355,061 B1 | 3/2002 | Quiachon et al. |
| 6,358,258 B1 | 3/2002 | Arcia et al. |
| 6,375,671 B1 | 4/2002 | Kobayashi et al. |
| D457,958 S | 5/2002 | Dycus |
| 6,383,208 B1 | 5/2002 | Sancoff et al. |
| 6,391,048 B1 | 5/2002 | Ginn et al. |
| 6,395,015 B1 | 5/2002 | Borst et al. |
| 6,398,752 B1 | 6/2002 | Sweezer et al. |
| 6,402,765 B1 | 6/2002 | Monassevitch et al. |
| 6,409,739 B1 | 6/2002 | Nobles et al. |
| 6,419,669 B1 | 7/2002 | Frazier et al. |
| 6,421,899 B1 | 7/2002 | Zitnay |
| 6,423,054 B1 | 7/2002 | Ouchi |
| 6,425,911 B1 | 7/2002 | Akerfeldt et al. |
| 6,428,472 B1 | 8/2002 | Haas |
| 6,428,548 B1 | 8/2002 | Durgin et al. |
| 6,443,158 B1 | 9/2002 | Lafontaine et al. |
| 6,443,963 B1 | 9/2002 | Baldwin et al. |
| 6,447,540 B1 | 9/2002 | Fontaine et al. |
| 6,450,391 B1 | 9/2002 | Kayan et al. |
| 6,455,053 B1 | 9/2002 | Okada et al. |
| 6,458,130 B1 | 10/2002 | Frazier et al. |
| 6,461,364 B1 * | 10/2002 | Ginn et al. ................... 606/142 |
| 6,482,224 B1 | 11/2002 | Michler et al. |
| 6,488,692 B1 | 12/2002 | Spence et al. |
| 6,494,848 B1 | 12/2002 | Sommercorn et al. |
| 6,500,115 B2 | 12/2002 | Krattiger et al. |
| 6,506,210 B1 | 1/2003 | Kanner |
| 6,508,828 B1 | 1/2003 | Akerfeldt et al. |
| 6,514,280 B1 | 2/2003 | Gilson |
| 6,517,555 B1 | 2/2003 | Caro |
| 6,517,569 B2 | 2/2003 | Mikus et al. |
| 6,527,737 B2 | 3/2003 | Kaneshige |
| 6,533,762 B2 | 3/2003 | Kanner et al. |
| 6,533,812 B2 | 3/2003 | Swanson et al. |
| 6,537,288 B2 | 3/2003 | Vargas et al. |
| 6,544,230 B1 | 4/2003 | Flaherty et al. |
| 6,547,806 B1 | 4/2003 | Ding |
| 6,551,319 B2 | 4/2003 | Lieberman |
| 6,558,349 B1 | 5/2003 | Kirkman |
| 6,569,173 B1 | 5/2003 | Blatter et al. |
| 6,569,185 B2 | 5/2003 | Ungs |
| 6,572,629 B2 | 6/2003 | Kalloo et al. |
| 6,582,452 B2 | 6/2003 | Coleman et al. |
| 6,582,482 B2 | 6/2003 | Gillman et al. |
| 6,596,012 B2 | 7/2003 | Akerfeldt et al. |
| 6,596,013 B2 | 7/2003 | Yang et al. |
| 6,599,303 B1 | 7/2003 | Peterson et al. |
| 6,599,311 B1 | 7/2003 | Biggs et al. |
| 6,602,263 B1 | 8/2003 | Swanson et al. |
| 6,610,072 B1 | 8/2003 | Christy et al. |
| 6,613,059 B2 | 9/2003 | Schaller et al. |
| 6,616,686 B2 | 9/2003 | Coleman et al. |
| 6,620,165 B2 | 9/2003 | Wellisz |
| 6,623,509 B2 | 9/2003 | Ginn |
| 6,623,510 B2 | 9/2003 | Carley et al. |
| 6,626,918 B1 | 9/2003 | Ginn et al. |
| 6,626,919 B1 | 9/2003 | Swanstrom |
| 6,626,920 B2 | 9/2003 | Whayne |
| 6,626,930 B1 | 9/2003 | Allen et al. |
| 6,632,197 B2 | 10/2003 | Lyon |
| 6,632,238 B2 | 10/2003 | Ginn et al. |
| 6,634,537 B2 | 10/2003 | Chen |
| 6,645,205 B2 | 11/2003 | Ginn |
| 6,645,225 B1 | 11/2003 | Atkinson |
| 6,652,538 B2 | 11/2003 | Kayan et al. |
| 6,652,556 B1 | 11/2003 | VanTassel et al. |
| 6,663,633 B1 | 12/2003 | Pierson, III |
| 6,663,655 B2 | 12/2003 | Ginn et al. |
| 6,669,714 B2 | 12/2003 | Coleman et al. |
| 6,673,083 B1 | 1/2004 | Kayan et al. |
| 6,676,665 B2 | 1/2004 | Foley et al. |
| 6,676,671 B2 | 1/2004 | Robertson et al. |
| 6,676,685 B2 | 1/2004 | Pedros et al. |
| 6,679,904 B2 | 1/2004 | Gleeson et al. |
| 6,685,707 B2 | 2/2004 | Roman et al. |
| 6,689,147 B1 | 2/2004 | Koster, Jr. |
| 6,695,867 B2 | 2/2004 | Ginn et al. |
| 6,699,256 B1 | 3/2004 | Logan et al. |
| 6,702,826 B2 | 3/2004 | Liddicoat et al. |
| 6,712,836 B1 | 3/2004 | Berg et al. |
| 6,712,837 B2 | 3/2004 | Akerfeldt et al. |

(56) References Cited

U.S. PATENT DOCUMENTS

| | | |
|---|---|---|
| 6,719,777 B2 | 4/2004 | Ginn et al. |
| 6,726,704 B1 | 4/2004 | Loshakove et al. |
| 6,743,195 B2 | 6/2004 | Zucker |
| 6,743,243 B1 | 6/2004 | Roy et al. |
| 6,743,259 B2 | 6/2004 | Ginn |
| 6,746,472 B2 | 6/2004 | Frazier et al. |
| 6,749,621 B2 | 6/2004 | Pantages et al. |
| 6,749,622 B2 | 6/2004 | McGuckin et al. |
| 6,752,813 B2 | 6/2004 | Goldfarb et al. |
| 6,755,842 B2 | 6/2004 | Kanner et al. |
| 6,758,855 B2 | 7/2004 | Fulton, III et al. |
| 6,767,356 B2 | 7/2004 | Kanner et al. |
| 6,776,784 B2 | 8/2004 | Ginn |
| 6,780,197 B2 | 8/2004 | Roe et al. |
| 6,786,915 B2 | 9/2004 | Akerfeldt et al. |
| 6,790,218 B2 | 9/2004 | Jayaraman |
| 6,790,220 B2 | 9/2004 | Morris et al. |
| 6,837,893 B2 | 1/2005 | Miller |
| 6,837,906 B2 | 1/2005 | Ginn |
| 6,846,319 B2 | 1/2005 | Ginn et al. |
| 6,860,895 B1 | 3/2005 | Akerfeldt et al. |
| 6,890,343 B2 | 5/2005 | Ginn et al. |
| 6,896,687 B2 | 5/2005 | Dakov |
| 6,896,692 B2 | 5/2005 | Ginn et al. |
| 6,913,607 B2 | 7/2005 | Ainsworth et al. |
| 6,926,723 B1 | 8/2005 | Mulhauser et al. |
| 6,926,731 B2 | 8/2005 | Coleman et al. |
| 6,929,634 B2 | 8/2005 | Dorros et al. |
| 6,942,641 B2 | 9/2005 | Seddon |
| 6,942,674 B2 | 9/2005 | Belef et al. |
| 6,942,691 B1 | 9/2005 | Chuter |
| 6,964,668 B2 | 11/2005 | Modesitt et al. |
| 6,969,391 B1 | 11/2005 | Gazzani |
| 6,969,397 B2 | 11/2005 | Ginn |
| 6,989,003 B2 | 1/2006 | Wing et al. |
| 6,989,016 B2 | 1/2006 | Tallarida et al. |
| 7,001,398 B2 | 2/2006 | Carley et al. |
| 7,001,400 B1 | 2/2006 | Modesitt et al. |
| 7,008,435 B2 | 3/2006 | Cummins |
| 7,008,439 B1 | 3/2006 | Janzen et al. |
| 7,025,776 B1 | 4/2006 | Houser et al. |
| 7,033,379 B2 | 4/2006 | Peterson |
| 7,060,084 B1 | 6/2006 | Loshakove et al. |
| 7,063,711 B1 | 6/2006 | Loshakove et al. |
| 7,074,232 B2 | 7/2006 | Kanner et al. |
| 7,076,305 B2 | 7/2006 | Imran et al. |
| 7,083,635 B2 | 8/2006 | Ginn |
| 7,087,064 B1 | 8/2006 | Hyde |
| 7,087,088 B2 | 8/2006 | Berg et al. |
| 7,108,709 B2 | 9/2006 | Cummins |
| 7,111,768 B2 | 9/2006 | Cummins et al. |
| 7,112,225 B2 | 9/2006 | Ginn |
| 7,144,411 B2 | 12/2006 | Ginn et al. |
| 7,163,551 B2 | 1/2007 | Anthony et al. |
| 7,169,158 B2 | 1/2007 | Sniffin et al. |
| 7,169,164 B2 | 1/2007 | Borillo et al. |
| 7,211,101 B2 | 5/2007 | Carley et al. |
| 7,220,268 B2 | 5/2007 | Blatter |
| 7,229,452 B2 | 6/2007 | Kayan |
| 7,261,716 B2 | 8/2007 | Strobel et al. |
| 7,306,614 B2 | 12/2007 | Weller et al. |
| 7,311,720 B2 | 12/2007 | Mueller et al. |
| 7,316,704 B2 | 1/2008 | Bagaoisan et al. |
| 7,316,706 B2 | 1/2008 | Bloom et al. |
| 7,322,995 B2 | 1/2008 | Buckman et al. |
| 7,326,230 B2 | 2/2008 | Ravikumar |
| 7,331,979 B2 | 2/2008 | Khosravi et al. |
| 7,335,220 B2 | 2/2008 | Khosravi et al. |
| D566,272 S | 4/2008 | Walburg et al. |
| D361,178 S | 4/2008 | Hearn et al. |
| 7,361,183 B2 | 4/2008 | Ginn |
| 7,361,185 B2 | 4/2008 | O'Malley et al. |
| 7,393,363 B2 | 7/2008 | Ginn |
| 7,396,359 B1 | 7/2008 | Derowe et al. |
| 7,431,729 B2 | 10/2008 | Chanduszko |
| 7,445,596 B2 | 11/2008 | Kucklick et al. |
| 7,465,286 B2 | 12/2008 | Patterson et al. |
| 7,533,790 B1 | 5/2009 | Knodel et al. |
| 7,556,632 B2 | 7/2009 | Zadno |
| 7,582,103 B2 | 9/2009 | Young et al. |
| 7,582,104 B2 | 9/2009 | Corcoran et al. |
| 7,597,706 B2 | 10/2009 | Kanner et al. |
| 7,618,427 B2 | 11/2009 | Ortiz et al. |
| 7,622,628 B2 | 11/2009 | Bergin et al. |
| D611,144 S | 3/2010 | Reynolds |
| 7,678,135 B2 | 3/2010 | Maahs et al. |
| 7,780,696 B2 | 8/2010 | Daniel et al. |
| 7,806,904 B2 | 10/2010 | Carley et al. |
| 7,819,895 B2 | 10/2010 | Ginn et al. |
| 7,824,419 B2 | 11/2010 | Boraiah |
| 7,841,502 B2 | 11/2010 | Walberg et al. |
| 7,842,068 B2 | 11/2010 | Ginn |
| 7,850,709 B2 | 12/2010 | Cummins et al. |
| 7,850,710 B2 | 12/2010 | Huss |
| 7,850,797 B2 | 12/2010 | Carley et al. |
| 7,854,810 B2 | 12/2010 | Carley et al. |
| 7,857,828 B2 | 12/2010 | Jabba et al. |
| 7,867,249 B2 | 1/2011 | Palermo et al. |
| 7,875,054 B2 | 1/2011 | LaFontaine |
| 7,879,071 B2 | 2/2011 | Carley et al. |
| 7,887,555 B2 | 2/2011 | Carley et al. |
| 7,887,563 B2 | 2/2011 | Cummins et al. |
| 7,901,428 B2 | 3/2011 | Ginn et al. |
| 7,905,900 B2 | 3/2011 | Palermo |
| 7,918,873 B2 | 4/2011 | Cummins et al. |
| 7,931,669 B2 | 4/2011 | Ginn et al. |
| 7,931,671 B2 | 4/2011 | Tenerz |
| 7,967,842 B2 | 6/2011 | Bakos |
| 8,007,512 B2 | 8/2011 | Ginn et al. |
| 8,083,768 B2 | 12/2011 | Ginn et al. |
| 8,103,327 B2 | 1/2012 | Harlev et al. |
| 8,105,352 B2 | 1/2012 | Egnelöv |
| 8,128,644 B2 | 3/2012 | Carley et al. |
| 8,172,749 B2 | 5/2012 | Melsheimer |
| 8,182,497 B2 | 5/2012 | Carley et al. |
| 8,192,459 B2 | 6/2012 | Cummins et al. |
| 8,202,283 B2 | 6/2012 | Carley et al. |
| 8,202,293 B2 | 6/2012 | Ellingwood et al. |
| 8,202,294 B2 | 6/2012 | Jabba et al. |
| 8,211,122 B2 | 7/2012 | McIntosh |
| 8,216,260 B2 | 7/2012 | Lam et al. |
| 8,226,681 B2 | 7/2012 | Clark et al. |
| 8,236,026 B2 | 8/2012 | Carley et al. |
| 8,257,390 B2 | 9/2012 | Carley et al. |
| 8,303,624 B2 | 11/2012 | Fortson |
| 8,313,497 B2 | 11/2012 | Walberg et al. |
| 8,323,312 B2 | 12/2012 | Clark |
| 8,398,656 B2 | 3/2013 | Palermo et al. |
| 8,398,676 B2 | 3/2013 | Roorda et al. |
| 8,403,929 B2 | 3/2013 | Weisshaupt et al. |
| 8,409,228 B2 | 4/2013 | Blatter et al. |
| 8,469,995 B2 | 6/2013 | Cummins et al. |
| 8,480,687 B2 | 7/2013 | Ducharme et al. |
| 8,486,092 B2 | 7/2013 | Carley et al. |
| 8,486,108 B2 | 7/2013 | Carley et al. |
| 8,518,057 B2 | 8/2013 | Walberg et al. |
| 8,529,587 B2 | 9/2013 | Ellingwood et al. |
| 8,556,930 B2 | 10/2013 | Ellingwood |
| 8,556,932 B2 | 10/2013 | Ziobro |
| 8,562,630 B2 | 10/2013 | Campbell |
| 8,574,244 B2 | 11/2013 | Reynolds |
| 8,579,932 B2 | 11/2013 | Pantages |
| 8,585,836 B2 | 11/2013 | Carley et al. |
| 8,590,760 B2 | 11/2013 | Cummins et al. |
| 8,597,325 B2 | 12/2013 | Ginn |
| 8,603,116 B2 | 12/2013 | Roorda |
| 8,603,136 B2 | 12/2013 | Ginn |
| 8,617,184 B2 | 12/2013 | Oepen |
| 8,657,852 B2 | 2/2014 | Roorda et al. |
| 8,672,953 B2 | 3/2014 | Reyes et al. |
| 8,690,910 B2 | 4/2014 | Carley et al. |
| 8,728,119 B2 | 5/2014 | Cummins |
| 8,758,396 B2 | 6/2014 | Ginn et al. |
| 8,758,398 B2 | 6/2014 | Carley |

(56) References Cited

U.S. PATENT DOCUMENTS

| | | |
|---|---|---|
| 8,758,399 B2 | 6/2014 | Fortson et al. |
| 8,758,400 B2 | 6/2014 | Ginn et al. |
| 8,784,447 B2 | 7/2014 | Coleman et al. |
| 8,808,310 B2 | 8/2014 | Jones et al. |
| 8,820,602 B2 | 9/2014 | Walberg et al. |
| 8,821,534 B2 | 9/2014 | Voss |
| 8,834,494 B2 | 9/2014 | Schorr et al. |
| 8,858,594 B2 | 10/2014 | Clark |
| 8,893,947 B2 | 11/2014 | Reynolds et al. |
| 8,905,937 B2 | 12/2014 | Ellingwood et al. |
| 8,926,656 B2 | 1/2015 | Palermo et al. |
| 8,992,549 B2 | 3/2015 | Bennett, III |
| 2001/0007077 A1 | 7/2001 | Ginn et al. |
| 2001/0021855 A1 | 9/2001 | Levinson |
| 2001/0031972 A1 | 10/2001 | Robertson et al. |
| 2001/0031973 A1 | 10/2001 | Nobles et al. |
| 2001/0044639 A1 | 11/2001 | Levinson |
| 2001/0046518 A1 | 11/2001 | Sawhney |
| 2001/0047180 A1 | 11/2001 | Grudem et al. |
| 2002/0022822 A1 | 2/2002 | Cragg et al. |
| 2002/0026215 A1 | 2/2002 | Redmond et al. |
| 2002/0026216 A1 | 2/2002 | Grimes |
| 2002/0029050 A1 | 3/2002 | Gifford, III et al. |
| 2002/0038127 A1 | 3/2002 | Blatter et al. |
| 2002/0042622 A1 | 4/2002 | Vargas et al. |
| 2002/0049427 A1 | 4/2002 | Wiener et al. |
| 2002/0049453 A1 | 4/2002 | Nobles et al. |
| 2002/0056460 A1 | 5/2002 | Boyd et al. |
| 2002/0058960 A1 | 5/2002 | Hudson et al. |
| 2002/0062104 A1 | 5/2002 | Ashby et al. |
| 2002/0077656 A1 | 6/2002 | Ginn et al. |
| 2002/0077657 A1 | 6/2002 | Ginn et al. |
| 2002/0077658 A1 | 6/2002 | Ginn |
| 2002/0082641 A1 | 6/2002 | Ginn et al. |
| 2002/0095164 A1 | 7/2002 | Andreas et al. |
| 2002/0095181 A1 | 7/2002 | Beyar |
| 2002/0099389 A1 | 7/2002 | Michler et al. |
| 2002/0106409 A1 | 8/2002 | Sawhney et al. |
| 2002/0107542 A1 | 8/2002 | Kanner et al. |
| 2002/0151921 A1 | 10/2002 | Kanner et al. |
| 2002/0151963 A1 | 10/2002 | Brown et al. |
| 2002/0169475 A1 | 11/2002 | Gainor et al. |
| 2002/0183786 A1 | 12/2002 | Girton |
| 2002/0183787 A1 | 12/2002 | Wahr et al. |
| 2002/0188170 A1 | 12/2002 | Santamore et al. |
| 2002/0198562 A1 | 12/2002 | Akerfeldt et al. |
| 2002/0198589 A1 | 12/2002 | Leong |
| 2003/0004543 A1 | 1/2003 | Gleeson et al. |
| 2003/0009180 A1 | 1/2003 | Hinchliffe et al. |
| 2003/0018358 A1 | 1/2003 | Saadat |
| 2003/0023248 A1 | 1/2003 | Parodi |
| 2003/0032981 A1 | 2/2003 | Kanner et al. |
| 2003/0033006 A1 | 2/2003 | Phillips et al. |
| 2003/0045893 A1 | 3/2003 | Ginn |
| 2003/0055455 A1 | 3/2003 | Yang et al. |
| 2003/0060846 A1 | 3/2003 | Egnelov et al. |
| 2003/0065358 A1 | 4/2003 | Frecker et al. |
| 2003/0078465 A1 | 4/2003 | Pai et al. |
| 2003/0083679 A1 | 5/2003 | Grudem et al. |
| 2003/0093096 A1 | 5/2003 | McGuckin et al. |
| 2003/0093108 A1 | 5/2003 | Avellanet et al. |
| 2003/0097140 A1 | 5/2003 | Kanner |
| 2003/0109890 A1 | 6/2003 | Kanner et al. |
| 2003/0125766 A1 | 7/2003 | Ding |
| 2003/0139819 A1 | 7/2003 | Beer et al. |
| 2003/0144695 A1 | 7/2003 | McGuckin, Jr. et al. |
| 2003/0158578 A1 | 8/2003 | Pantages et al. |
| 2003/0167063 A1 | 9/2003 | Kerr |
| 2003/0195504 A1 | 10/2003 | Tallarida et al. |
| 2003/0208211 A1 | 11/2003 | Kortenbach |
| 2004/0002763 A1 | 1/2004 | Phillips et al. |
| 2004/0009205 A1 | 1/2004 | Sawhney |
| 2004/0044350 A1 | 3/2004 | Martin et al. |
| 2004/0049224 A1 | 3/2004 | Buehlmann et al. |
| 2004/0059376 A1 | 3/2004 | Breuniger |
| 2004/0068273 A1 | 4/2004 | Fariss et al. |
| 2004/0078053 A1 | 4/2004 | Berg et al. |
| 2004/0082906 A1 | 4/2004 | Tallarida et al. |
| 2004/0087985 A1 | 5/2004 | Loshakove et al. |
| 2004/0092962 A1 | 5/2004 | Thornton et al. |
| 2004/0092964 A1 | 5/2004 | Modesitt et al. |
| 2004/0092968 A1 | 5/2004 | Caro et al. |
| 2004/0092973 A1 | 5/2004 | Chanduszko et al. |
| 2004/0093024 A1 | 5/2004 | Lousararian et al. |
| 2004/0093027 A1 | 5/2004 | Fabisiak et al. |
| 2004/0097978 A1 | 5/2004 | Modesitt et al. |
| 2004/0106980 A1 | 6/2004 | Solovay et al. |
| 2004/0127940 A1 | 7/2004 | Ginn et al. |
| 2004/0143290 A1 | 7/2004 | Brightbill |
| 2004/0143291 A1 | 7/2004 | Corcoran et al. |
| 2004/0147957 A1 | 7/2004 | Pierson, III |
| 2004/0158127 A1 | 8/2004 | Okada |
| 2004/0158287 A1 | 8/2004 | Cragg et al. |
| 2004/0158309 A1 | 8/2004 | Wachter et al. |
| 2004/0167511 A1 | 8/2004 | Buehlmann et al. |
| 2004/0191277 A1 | 9/2004 | Sawhney et al. |
| 2004/0215232 A1 | 10/2004 | Belhe et al. |
| 2004/0225301 A1 | 11/2004 | Roop et al. |
| 2004/0243216 A1 | 12/2004 | Gregorich |
| 2004/0249412 A1 | 12/2004 | Snow et al. |
| 2004/0254591 A1 | 12/2004 | Kanner et al. |
| 2004/0267193 A1 | 12/2004 | Bagaoisan et al. |
| 2004/0267308 A1 | 12/2004 | Bagaoisan et al. |
| 2004/0267312 A1 | 12/2004 | Kanner et al. |
| 2005/0038460 A1 | 2/2005 | Jayaraman |
| 2005/0038500 A1 | 2/2005 | Boylan et al. |
| 2005/0059982 A1 | 3/2005 | Zung et al. |
| 2005/0075654 A1 | 4/2005 | Kelleher |
| 2005/0075665 A1 | 4/2005 | Brenzel et al. |
| 2005/0085851 A1 | 4/2005 | Fiehler et al. |
| 2005/0085854 A1 | 4/2005 | Ginn |
| 2005/0085855 A1 | 4/2005 | Forsberg |
| 2005/0090859 A1 | 4/2005 | Ravlkumar |
| 2005/0119695 A1 | 6/2005 | Carley et al. |
| 2005/0121042 A1 | 6/2005 | Belhe et al. |
| 2005/0148818 A1 | 7/2005 | Mesallum |
| 2005/0149066 A1 | 7/2005 | Stafford |
| 2005/0149117 A1 | 7/2005 | Khosravi et al. |
| 2005/0152949 A1 | 7/2005 | Hotchkiss et al. |
| 2005/0154401 A1 | 7/2005 | Weldon et al. |
| 2005/0165357 A1 | 7/2005 | McGuckin et al. |
| 2005/0169974 A1 | 8/2005 | Tenerz et al. |
| 2005/0177189 A1 | 8/2005 | Ginn et al. |
| 2005/0187564 A1 | 8/2005 | Jayaraman |
| 2005/0203552 A1 | 9/2005 | Laufer et al. |
| 2005/0222614 A1 | 10/2005 | Ginn et al. |
| 2005/0228405 A1 | 10/2005 | Maruyama et al. |
| 2005/0228443 A1 | 10/2005 | Yassinzadeh |
| 2005/0245876 A1 | 11/2005 | Khosravi et al. |
| 2005/0256532 A1 | 11/2005 | Nayak et al. |
| 2005/0267495 A1* | 12/2005 | Ginn ............... A61B 17/0057 606/151 |
| 2005/0267524 A1 | 12/2005 | Chanduszko |
| 2005/0273136 A1 | 12/2005 | Belef et al. |
| 2005/0273137 A1 | 12/2005 | Ginn |
| 2005/0283188 A1 | 12/2005 | Loshakove et al. |
| 2006/0030867 A1 | 2/2006 | Zadno |
| 2006/0034930 A1 | 2/2006 | Khosravi et al. |
| 2006/0047313 A1 | 3/2006 | Khanna et al. |
| 2006/0064115 A1 | 3/2006 | Allen et al. |
| 2006/0069397 A1 | 3/2006 | Nobles et al. |
| 2006/0100664 A1 | 5/2006 | Pai et al. |
| 2006/0142784 A1 | 6/2006 | Kontos |
| 2006/0190014 A1 | 8/2006 | Ginn et al. |
| 2006/0190036 A1 | 8/2006 | Wendel et al. |
| 2006/0190037 A1 | 8/2006 | Ginn et al. |
| 2006/0195123 A1 | 8/2006 | Ginn et al. |
| 2006/0195125 A1 | 8/2006 | Sakakine et al. |
| 2006/0206146 A1 | 9/2006 | Tenerz |
| 2006/0217744 A1* | 9/2006 | Bender et al. ............... 606/142 |
| 2006/0229553 A1 | 10/2006 | Hammack et al. |
| 2006/0253037 A1 | 11/2006 | Ginn et al. |
| 2006/0253072 A1 | 11/2006 | Pai et al. |
| 2006/0281968 A1 | 12/2006 | Duran et al. |

(56) References Cited

U.S. PATENT DOCUMENTS

| | | |
|---|---|---|
| 2006/0287673 A1 | 12/2006 | Brett et al. |
| 2006/0287674 A1 | 12/2006 | Ginn et al. |
| 2006/0293698 A1 | 12/2006 | Douk |
| 2007/0005093 A1 | 1/2007 | Cox |
| 2007/0010851 A1 | 1/2007 | Chanduszko et al. |
| 2007/0010853 A1 | 1/2007 | Ginn et al. |
| 2007/0021778 A1 | 1/2007 | Carly |
| 2007/0027476 A1 | 2/2007 | Harris et al. |
| 2007/0027525 A1 | 2/2007 | Ben-Muvhar |
| 2007/0049968 A1 | 3/2007 | Sibbitt, Jr. et al. |
| 2007/0049970 A1 | 3/2007 | Belef et al. |
| 2007/0060858 A1* | 3/2007 | Sogard et al. ............... 604/8 |
| 2007/0060895 A1 | 3/2007 | Sibbitt, Jr. et al. |
| 2007/0060950 A1 | 3/2007 | Khosravi et al. |
| 2007/0073337 A1 | 3/2007 | Abbott et al. |
| 2007/0078302 A1 | 4/2007 | Ortiz et al. |
| 2007/0083230 A1 | 4/2007 | Javois |
| 2007/0083231 A1 | 4/2007 | Lee |
| 2007/0093869 A1 | 4/2007 | Bloom et al. |
| 2007/0112304 A1 | 5/2007 | Voss |
| 2007/0112365 A1 | 5/2007 | Hilal et al. |
| 2007/0112385 A1 | 5/2007 | Conlon |
| 2007/0123816 A1 | 5/2007 | Zhu et al. |
| 2007/0123817 A1 | 5/2007 | Khosravi et al. |
| 2007/0149996 A1 | 6/2007 | Coughlin |
| 2007/0167981 A1 | 7/2007 | Opolski et al. |
| 2007/0172430 A1 | 7/2007 | Brito et al. |
| 2007/0179527 A1 | 8/2007 | Eskuri et al. |
| 2007/0185529 A1 | 8/2007 | Coleman et al. |
| 2007/0185530 A1 | 8/2007 | Chin-Chen et al. |
| 2007/0203507 A1 | 8/2007 | McLaughlin et al. |
| 2007/0225755 A1 | 9/2007 | Preinitz et al. |
| 2007/0225756 A1 | 9/2007 | Preinitz et al. |
| 2007/0225757 A1 | 9/2007 | Preinitz et al. |
| 2007/0225758 A1 | 9/2007 | Preinitz et al. |
| 2007/0239209 A1 | 10/2007 | Fallman |
| 2007/0265658 A1 | 11/2007 | Nelson et al. |
| 2007/0275036 A1 | 11/2007 | Green, III et al. |
| 2007/0276488 A1 | 11/2007 | Wachter et al. |
| 2007/0282373 A1 | 12/2007 | Ashby et al. |
| 2008/0009794 A1 | 1/2008 | Bagaoisan et al. |
| 2008/0033459 A1 | 2/2008 | Shafi et al. |
| 2008/0045979 A1 | 2/2008 | Ma |
| 2008/0058839 A1 | 3/2008 | Nobles et al. |
| 2008/0065151 A1 | 3/2008 | Ginn |
| 2008/0082123 A1 | 4/2008 | Forsberg et al. |
| 2008/0086075 A1 | 4/2008 | Isik et al. |
| 2008/0091235 A1 | 4/2008 | Sirota |
| 2008/0093414 A1 | 4/2008 | Bender et al. |
| 2008/0097509 A1 | 4/2008 | Beyar et al. |
| 2008/0114378 A1 | 5/2008 | Matsushita |
| 2008/0114395 A1 | 5/2008 | Mathisen et al. |
| 2008/0177288 A1 | 7/2008 | Carlson |
| 2008/0208225 A1 | 8/2008 | Seibold et al. |
| 2008/0210737 A1 | 9/2008 | Ginn et al. |
| 2008/0215089 A1 | 9/2008 | Williams et al. |
| 2008/0215090 A1* | 9/2008 | Gonzales et al. ............ 606/219 |
| 2008/0221616 A1 | 9/2008 | Ginn et al. |
| 2008/0243148 A1 | 10/2008 | Mikkaichi et al. |
| 2008/0243182 A1 | 10/2008 | Bates et al. |
| 2008/0249504 A1 | 10/2008 | Lattouf et al. |
| 2008/0269801 A1 | 10/2008 | Coleman et al. |
| 2008/0269802 A1 | 10/2008 | Coleman et al. |
| 2008/0272173 A1 | 11/2008 | Coleman et al. |
| 2008/0287988 A1 | 11/2008 | Smith et al. |
| 2008/0294001 A1 | 11/2008 | Surti |
| 2008/0300628 A1 | 12/2008 | Ellingwood |
| 2008/0312667 A1 | 12/2008 | Drasler et al. |
| 2008/0312686 A1 | 12/2008 | Ellingwood |
| 2008/0312740 A1 | 12/2008 | Wachter et al. |
| 2009/0054912 A1 | 2/2009 | Heanue et al. |
| 2009/0062846 A1 | 3/2009 | Ken |
| 2009/0112306 A1 | 4/2009 | Bonsignore et al. |
| 2009/0132031 A1 | 5/2009 | Cook et al. |
| 2009/0137900 A1 | 5/2009 | Bonner et al. |
| 2009/0157101 A1 | 6/2009 | Reyes et al. |
| 2009/0171388 A1 | 7/2009 | Dave et al. |
| 2009/0187215 A1 | 7/2009 | Mackiewicz et al. |
| 2009/0216267 A1 | 8/2009 | Willard et al. |
| 2009/0221960 A1 | 9/2009 | Albrecht et al. |
| 2009/0227938 A1 | 9/2009 | Fasching et al. |
| 2009/0230168 A1 | 9/2009 | Coleman et al. |
| 2009/0254119 A1 | 10/2009 | Sibbitt, Jr. et al. |
| 2009/0259233 A1 | 10/2009 | Bogart et al. |
| 2009/0281555 A1 | 11/2009 | Stone |
| 2009/0287244 A1 | 11/2009 | Kokish |
| 2009/0299133 A1 | 12/2009 | Gifford, III et al. |
| 2009/0312789 A1 | 12/2009 | Kassab et al. |
| 2010/0022821 A1 | 1/2010 | Dubi et al. |
| 2010/0042118 A1 | 2/2010 | Garrison et al. |
| 2010/0042144 A1 | 2/2010 | Bennett |
| 2010/0114119 A1* | 5/2010 | McLawhorn ........ A61B 17/064 606/139 |
| 2010/0114156 A1 | 5/2010 | Mehl |
| 2010/0130965 A1 | 5/2010 | Sibbitt, Jr. et al. |
| 2010/0179567 A1 | 7/2010 | Voss et al. |
| 2010/0179571 A1 | 7/2010 | Voss |
| 2010/0179572 A1 | 7/2010 | Voss et al. |
| 2010/0179589 A1 | 7/2010 | Roorda et al. |
| 2010/0179590 A1 | 7/2010 | Fortson et al. |
| 2010/0185216 A1 | 7/2010 | Garrison et al. |
| 2010/0185234 A1 | 7/2010 | Fortson et al. |
| 2010/0249828 A1 | 9/2010 | Mavani et al. |
| 2011/0054492 A1 | 3/2011 | Clark |
| 2011/0082495 A1 | 4/2011 | Ruiz |
| 2011/0137340 A1 | 6/2011 | Cummins |
| 2011/0178548 A1 | 7/2011 | Tenerz |
| 2011/0190793 A1 | 8/2011 | Nobles et al. |
| 2011/0218568 A1 | 9/2011 | Voss |
| 2011/0270282 A1 | 11/2011 | Lemke |
| 2011/0288563 A1 | 11/2011 | Gianotti et al. |
| 2011/0313452 A1 | 12/2011 | Carley et al. |
| 2012/0101520 A1 | 4/2012 | Ginn et al. |
| 2012/0245623 A1 | 9/2012 | Kariniemi et al. |
| 2013/0053792 A1 | 2/2013 | Fischell et al. |
| 2013/0138144 A1 | 5/2013 | Yibarren |
| 2013/0190778 A1 | 7/2013 | Palermo |
| 2013/0253539 A1 | 9/2013 | Walberg et al. |
| 2013/0310853 A1 | 11/2013 | Zaugg et al. |
| 2013/0338708 A1 | 12/2013 | Cummins et al. |
| 2014/0005692 A1 | 1/2014 | Ellingwood et al. |
| 2014/0018850 A1 | 1/2014 | Ellingwood |
| 2014/0081318 A1 | 3/2014 | Houser et al. |
| 2014/0142624 A1 | 5/2014 | Pantages et al. |
| 2014/0180311 A1 | 6/2014 | Voss |
| 2014/0222068 A1 | 8/2014 | Carley et al. |
| 2014/0222069 A1 | 8/2014 | Carley et al. |
| 2014/0309686 A1 | 10/2014 | Ginn et al. |
| 2014/0364900 A1 | 12/2014 | Fortson et al. |
| 2014/0364903 A1 | 12/2014 | Roorda et al. |
| 2015/0265279 A1 | 9/2015 | Walberg et al. |

FOREIGN PATENT DOCUMENTS

| | | |
|---|---|---|
| DE | 197 11 288 | 10/1998 |
| DE | 29723736 U1 | 4/1999 |
| DE | 19859952 | 2/2000 |
| DE | 102006056283 | 6/2008 |
| EP | 0 386 361 | 9/1990 |
| EP | 0 534 696 | 3/1993 |
| EP | 0 621 032 | 10/1994 |
| EP | 0 756 851 | 2/1997 |
| EP | 0 774 237 | 5/1997 |
| EP | 0 858 776 | 8/1998 |
| EP | 0 941 697 | 9/1999 |
| EP | 1 867 287 | 12/2007 |
| FR | 2 443 238 | 7/1980 |
| FR | 2 715 290 | 7/1995 |
| FR | 2 722 975 | 2/1996 |
| FR | 2 768 324 | 3/1999 |
| GB | 1 358 466 | 7/1974 |
| GB | 2 075 144 | 11/1981 |
| GB | 2 397 240 | 7/2004 |
| IE | S2000/0722 | 10/2001 |

(56) References Cited

FOREIGN PATENT DOCUMENTS

| | | |
|---|---|---|
| IE | S2000/0724 | 10/2001 |
| IE | S2001/0547 | 7/2002 |
| IE | S2001/0815 | 7/2002 |
| IE | S2001/0748 | 8/2002 |
| IE | S2001/0749 | 8/2002 |
| IE | S2002/0452 | 12/2002 |
| IE | S2002/0664 | 2/2003 |
| IE | S2002/0665 | 2/2003 |
| IE | S2002/0451 | 7/2003 |
| IE | S2002/0552 | 7/2003 |
| IE | S2003/0424 | 12/2003 |
| IE | S2003/0490 | 1/2004 |
| IE | S2004/0368 | 11/2005 |
| IE | S2005/0342 | 11/2005 |
| JP | 58-181006 | 12/1983 |
| JP | 12 74750 | 11/1989 |
| JP | 11500642 | 8/1997 |
| JP | 2000102546 | 4/2000 |
| NL | 9302140 | 7/1995 |
| PL | 171425 | 4/1997 |
| RU | 2086192 | 8/1997 |
| SU | 495067 | 12/1975 |
| SU | 912155 | 3/1982 |
| SU | 1243708 | 7/1986 |
| SU | 1324650 | 7/1987 |
| SU | 1405828 | 6/1988 |
| SU | 1456109 | 2/1989 |
| SU | 1560133 | 4/1990 |
| WO | WO 96/24291 | 8/1996 |
| WO | WO 97/00046 | 1/1997 |
| WO | WO 97/07741 | 3/1997 |
| WO | WO 97/20505 | 6/1997 |
| WO | WO 97/27897 | 8/1997 |
| WO | WO 98/06346 | 2/1998 |
| WO | WO 98/06448 | 2/1998 |
| WO | WO 98/16161 | 4/1998 |
| WO | WO 98/17179 | 4/1998 |
| WO | WO 98/18389 | 5/1998 |
| WO | WO 98/24374 | 6/1998 |
| WO | WO 98/25508 | 6/1998 |
| WO | WO 98/58591 | 12/1998 |
| WO | WO 99/21491 | 5/1999 |
| WO | WO 99/40849 | 8/1999 |
| WO | WO 99/60941 | 12/1999 |
| WO | WO 99/62408 | 12/1999 |
| WO | WO 99/62415 | 12/1999 |
| WO | WO 00/06029 | 2/2000 |
| WO | WO 00/07505 | 2/2000 |
| WO | WO 00/07640 | 2/2000 |
| WO | WO 00/27311 | 5/2000 |
| WO | WO 00/27313 | 5/2000 |
| WO | WO 00/56223 | 9/2000 |
| WO | WO 00/56227 | 9/2000 |
| WO | WO 00/56228 | 9/2000 |
| WO | WO 00/71032 | 11/2000 |
| WO | WO 01/21058 | 3/2001 |
| WO | WO 01/35832 | 5/2001 |
| WO | WO 01/47594 | 7/2001 |
| WO | WO 01/49186 | 7/2001 |
| WO | WO 01/91628 | 12/2001 |
| WO | WO 02/19915 | 3/2002 |
| WO | WO 02/19920 | 3/2002 |
| WO | WO 02/19922 | 3/2002 |
| WO | WO 02/19924 | 3/2002 |
| WO | WO 02/28286 | 4/2002 |
| WO | WO 02/38055 | 5/2002 |
| WO | WO 02/45593 | 6/2002 |
| WO | WO 02/45594 | 6/2002 |
| WO | WO 02/062234 | 8/2002 |
| WO | WO 02/098302 | 12/2002 |
| WO | WO 03/013363 | 2/2003 |
| WO | WO 03/013364 | 2/2003 |
| WO | WO 03/047434 | 6/2003 |
| WO | WO 03/071955 | 9/2003 |
| WO | WO 03/071956 | 9/2003 |
| WO | WO 03/071957 | 9/2003 |
| WO | WO 03/094748 | 11/2003 |
| WO | WO 03/101310 | 12/2003 |
| WO | WO 2004/004578 | 1/2004 |
| WO | WO 2004/012602 | 2/2004 |
| WO | WO 2004/060169 | 7/2004 |
| WO | WO 2004/069054 | 8/2004 |
| WO | WO 2005/000126 | 1/2005 |
| WO | WO 2005/006990 | 1/2005 |
| WO | WO 2005/041782 | 5/2005 |
| WO | WO 2005/063129 | 7/2005 |
| WO | WO 2005/082256 | 9/2005 |
| WO | WO 2005/092204 | 10/2005 |
| WO | WO 2005/110240 | 11/2005 |
| WO | WO 2005/112782 | 12/2005 |
| WO | WO 2005/115251 | 12/2005 |
| WO | WO 2005/115521 | 12/2005 |
| WO | WO 2006/000514 | 1/2006 |
| WO | WO 2006/026116 | 3/2006 |
| WO | WO 2006/052611 | 5/2006 |
| WO | WO 2006/052612 | 5/2006 |
| WO | WO 2006/078578 | 7/2006 |
| WO | WO 2006/083889 | 8/2006 |
| WO | WO 2006/115901 | 11/2006 |
| WO | WO 2006/115904 | 11/2006 |
| WO | WO 2006/118877 | 11/2006 |
| WO | WO 2007/005585 | 1/2007 |
| WO | WO 2007/025014 | 3/2007 |
| WO | WO 2007/081836 | 7/2007 |
| WO | WO 2007/088069 | 8/2007 |
| WO | WO 2008/031102 | 3/2008 |
| WO | WO 2008/036384 | 3/2008 |
| WO | WO 2008/074027 | 6/2008 |
| WO | WO 2008/150915 | 12/2008 |
| WO | WO 2009/079091 | 6/2009 |
| WO | WO 2010/062693 | 6/2010 |
| WO | WO 2010/081101 | 7/2010 |
| WO | WO 2010/081102 | 7/2010 |
| WO | WO 2010/081103 | 7/2010 |
| WO | WO 2010/081106 | 7/2010 |
| ZA | 200100527 | 1/2001 |
| ZA | 200100528 | 1/2001 |

OTHER PUBLICATIONS

U.S. Appl. No. 09/866,551, filed May 25, 2001, Ginn.
U.S. Appl. No. 12/113,092, filed Apr. 30, 2008, Ginn et al.
U.S. Appl. No. 13/017,636, filed Jan. 31, 2011, Carley et al.
U.S. Appl. No. 60/693,531, filed Jun. 24, 2005, Carly.
U.S. Appl. No. 60/696,069, filed Jul. 1, 2005, Pantages et al.
U.S. Appl. No. 60/793,444, filed Apr. 20, 2006, Jones et al.
U.S. Appl. No. 60/946,026, filed Jun. 25, 2007, Ellingwood.
U.S. Appl. No. 60/946,030, filed Jun. 25, 2007, Voss et al.
U.S. Appl. No. 60/946,042, filed Jun. 25, 2007, Ellingwood et al.
U.S. Appl. No. 61/015,144, filed Dec. 19, 2007, Mackiewicz et al.
U.S. Appl. No. 61/109,822, filed Oct. 30, 2008, Mehl et al.
U.S. Appl. No. 61/139,995, filed Dec. 22, 2008, Clark.
U.S. Appl. No. 61/141,597, filed Dec. 30, 2008, Clark.
U.S. Appl. No. 61/143,748, filed Jan. 9, 2009, Mehl et al.
U.S. Appl. No. 61/143,751, filed Jan. 9, 2009, Voss et al.
U.S. Appl. No. 61/145,468, filed Jan. 16, 2009, Fortson, et al.
U.S. Appl. No. 14/562,467, filed Dec. 5, 2014, Ellingwood et al.
"Hand tool for forming telephone connections—comprises pliers with reciprocably driven ram crimping clip around conductors against anvil", Derwent-ACC-No. 1978-B8090A. (Jan. 10, 1978).
Database WPI; Section PQ, Week 200120; Derwent Publications Ltd., London GB; Class P31, AN 2001-203165; XP002199926 & ZA 200 100 528 A (Anthony T), Feb. 28, 2001 (Feb. 28, 2001) abstract.
Deepak Mital et al, Renal Transplantation Without Sutures Using the Vascular Clipping System for Renal Artery and Vein Anastomosis—A New Technique, Transplantation Issue, Oct. 1996, pp. 1171-1173, vol. 62—No. 8, Section of Transplantation Surgery, Department of General Surgery, Rush-Presbyterian/St. Luke's Medical Center, Chigago, IL.

(56) References Cited

OTHER PUBLICATIONS

DL Wessel et al, Outpatient closure of the patent ductus arteriosus, Circulation, May 1988, pp. 1068-1071, vol. 77—No. 5, Department of Anesthesia, Children's Hospital, Boston, MA.
E Pikoulis et al, Arterial reconstruction with vascular clips is safe and quicker than sutured repair, Cardiovascular Surgery, Dec. 1998, pp. 573-578(6), vol. 6—No. 6, Department of Surgery, Uniformed Services University of the Health Sciences, Bethesda, MD.
G Gershony et al, Novel vascular sealing device for closure of percutaneous vascular access sites, Cathet. Cardiovasc. Diagn., Jan. 1998, pp. 82-88, vol. 45.
H De Swart et al, A new hemostatic puncture closure device for the immediate sealing of arterial puncture sites, American journal of cardiology, Aug. 1993, pp. 445-449, vol. 72—No. 5, Department of Cardiology, Academic Hospital Maastricht, The Netherlands.
Harrith M. Hasson M.D., Laparoscopic Cannula Cone with Means for Cannula Stabilization and Wound Closure, The Journal of the American Association of Gynecologic Laparoscopists, May 1998, pp. 183-185, vol. 5—No. 2, Division of Obstetrics and Gynecology, University of Chicago, Chigago, IL.
J. Findlay et al, Carotid Arteriotomy Closure Using a Vascular Clip System, Neurosurgery, Mar. 1998, pp. 550-554, vol. 42—No. 3, Division of Neurosurgery, University of Alberta, Edmonton, Canada.
Jeremy L Gilbert PHD, Wound Closure Biomaterials and Devices, Shock., Mar. 1999, p. 226, vol. 11—No. 3, Institution Northwestern University (editorial review).
Jochen T. Cremer, MD, et al, Different approaches for minimally invasive closure of atrial septal defects, Ann. Thorac. Surg., Nov. 1998, pp. 1648-1652, vol. 67, a Division of Thoracic and Cardiovascular Surgery, Surgical Center, Hannover Medical School. Hannover, Germany.
K Narayanan et al, Simultaneous primary closure of four fasciotomy wounds in a single setting using the Sure-Closure device, Injury, Jul. 1996, pp. 449-451, vol. 27—No. 6, Department of Surgery, Mercy Hospital of Pittsburgh, PA.
Marshall A.C., Lock J.E., Structural and Compliant Anatomy of the Patent Foramen Ovale in Patients Undergoing Transcatheter Closure, Am Heart J Aug. 2000; 140(2); pp. 303-307.
Md Gonze et al, Complications associated with percutaneous closure devices, Conference: Annual Meeting of the Society for Clinical Vascular Surgery, The American journal of surgery, Mar. 1999, pp. 209-211, vol. 178, No. 3, Department of Surgery, Section of Vascular Surgery, Ochsner Medical Institutions, New Orleans, LA.
Md Hellinger et al, Effective peritoneal and fascial closure of abdominal trocar sites utilizing the Endo-Judge, J Laparoendosc Surg., Oct. 1996, pp. 329-332, vol. 6—No. 5, Orlando Regional Medical Center, FL.
Michael Gianturco, A Play on Catheterization, Forbes, Dec. 1996, p. 146, vol. 158—No. 15.
Inlet Medical Inc. Brochure, pp. 1-2, referencing Om Elashry et al, Comparative clinical study of port-closure techniques following laparoscopic surgery, Department of Surgery, Mallickrodt Institute of Radiography, J Am Coll Surg., Oct. 1996, pp. 335-344, vol. 183—No. 4.
P M N Werker, et al, Review of facilitated approaches to vascular anastomosis surgery, Conference: Utrecht MICABG Workshop 2, The Annals of thoracic surgery, Apr. 1996, pp. S122-S127, vol. 63—No. 6, Department of Plastic, Reconstructive and Hand surgery, University Hospital Utrecht Netherlands Departments of Cardiology and Cardiopulmonary Surgery, Heart Lung Institute, Utrecht Netherlands.; Utrect University Hospital Utrecht Netherlands.
Peter Rhee MD et al, Use of Titanium Vascular Staples in Trauma, Journal of Trauma-Injury Infection & Critical Care, Dec. 1998, pp. 1097-1099, vol. 45—No. 6, Institution from the Department of Surgery, Washington Hospital Center, Washington DC, and Uniformed Services University of the Health Sciences, Bethesda, Maryland.
ProstarXL—Percutaneous Vascular Surgical Device, www.Archive.org, Jun. 1998, Original Publisher: http://prostar.com, may also be found at http://web.archive.org/web/19980630040429/www.perclose.com/htm 1/prstrxl.html.
Sa Beyer-Enke et al, Immediate sealing of arterial puncture site following femoropopliteal angioplasty: A prospective randomized trial, Cardiovascular and Interventional Radiology 1996, Nov.-Dec. 1996, pp. 406-410, vol. 19—No. 6, Gen Hosp North, Dept Dianost & Intervent Radiol, Nurnberg, Germany (Reprint).
Scott Hensley, Closing Wounds. New Devices seal arterial punctures in double time, Modern Healthcare (United States), Mar. 23, 2008, p. 48.
Sigmund Silber et al, A novel vascular device for closure of percutaneous arterial access sites, The American Journal of Cardiology, Apr. 1999, pp. 1248-1252, vol. 83—No. 8.
Simonetta Blengino et al, A Randomized Study of the 8 French Hemostatic Puncture Closure Device vs Manual Compression After Coronary Interventions, Journal of the American College of Cardiology, Feb. 1995, p. 262A, vol. 25.—No. 2, Supplement 1.
Stretch Comb by Scunci, retrieved via internet at www.scunci.com/productdetail by examiner on Oct. 9, 2007, publication date unavailable.
Swee Lian Tan, MD, PhD, FACS, Explanation of Infected Hemostatic Puncture Closure Devices—A Case Report, Vascular and Endovascular Surgery, 1999, pp. 507-510, vol. 33—No. 5, Parkland Medical Center, Derry, New Hampshire.
Sy Nakada et al, Comparison of newer laparoscopic port closure techniques in the porcine model, J Endourol, Oct. 1995, pp. 397-401, vol. 9—No. 5, Department of Surgery/Urology, University of Wisconsin Medical School, Madison.
Taber's Cyclopedic Medical Dictionary, 18th Ed. 1997, pp. 747 and 1420.
Thomas P. Baum RPA-C et al, Delayed Primary Closure Using Silastic Vessel Loops and Skin Staples: Description of the Technique and Case Reports, Annals of Plastic Surgery, Mar. 1999, pp. 337-340, vol. 42—No. 3, Institution Department of Plastic and Reconstructive Surgery, Albert Einstein College of Medicine and Montefiore Medical Center, Bronx, NY.
Tomoaki Hinohara, Percutaneous vascular surgery (Prostar® Plus and Techstar® for femoral artery site closure), Interventional Cardiology Newsletter, May-Jul. 1997, pp. 19-22, pp. 24-28, vol. 5—No. 3-4.
Ut Aker et al, Immediate arterial hemostasis after cardiac catheterization: initial experience with a new puncture closure device, Cathet Cardiovasc Diagn, Mar. 1994, pp. 228-232, vol. 33—No. 3, Missouri Baptist Medical Center, St. Louis.
Wei Qu et al, An absorbable pinned-ring device for microvascular anastomosis of vein grafts: Experimental studies, Microsurgery 1999, Mar. 1999, pp. 128-134, vol. 19—No. 3, Department of Orthopaedic Surgery, Hiroshima University School of Medicine, Hiroshima, Japan.
William G. Kussmaul III MD, et al., Rapid arterial hemostasis and decreased access site complications after cardiac catheterization and angioplasty: Results of a randomized trial of a novel hemostatic device, Journal of the American College of Cardiology, Jun. 1995, pp. 1685-1692, vol. 25—No. 7.
U.S. Appl. No. 09/478,178, Nov. 6, 2000, Notice of Allowance.
U.S. Appl. No. 09/546,998, May 6, 2002, Notice of Allowance.
U.S. Appl. No. 09/610,238, Mar. 26, 2001, Notice of Allowance.
U.S. Appl. No. 09/610,238, Sep. 5, 2001 Office Action.
U.S. Appl. No. 09/610,238, Feb. 11, 2002, Notice of Allowance.
U.S. Appl. No. 09/680,837, Jul. 9, 2002, Office Action.
U.S. Appl. No. 09/680,837, Nov. 6, 2002, Office Action.
U.S. Appl. No. 09/680,837, Mar. 25, 2003, Office Action.
U.S. Appl. No. 09/680,837, Jun. 16, 2003, Notice of Allowance.
U.S. Appl. No. 09/732,178, Aug. 1, 2002, Office Action.
U.S. Appl. No. 09/732,178, Dec. 24, 2002, Office Action.
U.S. Appl. No. 09/732,178, Jun. 10, 2003, Office Action.
U.S. Appl. No. 09/732,178, Jul. 3, 2003, Office Action.
U.S. Appl. No. 09/732,178, Nov. 17, 2003, Notice of Allowance.
U.S. Appl. No. 09/732,835, Sep. 11, 2003, Office Action.
U.S. Appl. No. 09/732,835, Feb. 9, 2004, Office Action.
U.S. Appl. No. 09/732,835, Mar. 17, 2004, Notice of Allowance.

(56) References Cited

OTHER PUBLICATIONS

U.S. Appl. No. 09/764,813, Mar. 26, 2001, Office Action.
U.S. Appl. No. 09/764,813, Jun. 4, 2001, Notice of Allowance.
U.S. Appl. No. 09/933,299, Feb. 26, 2003, Office Action.
U.S. Appl. No. 09/933,299, Jun. 16, 2003, Notice of Allowance.
U.S. Appl. No. 09/948,813, Jan. 31, 2003, Notice of Allowance.
U.S. Appl. No. 09/949,398, Mar. 4, 2003, Office Action.
U.S. Appl. No. 09/949,398, Jul. 28, 2003, Notice of Allowance.
U.S. Appl. No. 09/949,438, Dec. 17, 2002, Office Action.
U.S. Appl. No. 09/949,438, Apr. 21, 2003, Notice of Allowance.
U.S. Appl. No. 10/006,400, Aug. 27, 2004, Office Action.
U.S. Appl. No. 10/006,400, Feb. 23, 2005, Office Action.
U.S. Appl. No. 10/006,400, Apr. 11, 2005, Office Action.
U.S. Appl. No. 10/006,400, Jul. 27, 2005, Office Action.
U.S. Appl. No. 10/006,400, Mar. 6, 2006, Office Action.
U.S. Appl. No. 10/006,400, May 24, 2006, Office Action.
U.S. Appl. No. 10/006,400, Oct. 26, 2006, Office Action.
U.S. Appl. No. 10/006,400, Apr. 19, 2007, Office Action.
U.S. Appl. No. 10/006,400, Apr. 2, 2008, Office Action.
U.S. Appl. No. 10/006,400, Jan. 2, 2009, Office Action.
U.S. Appl. No. 10/006,400, Jul. 9, 2009, Notice of Allowance.
U.S. Appl. No. 10/006,400, Jan. 13, 2010, Notice of Allowance.
U.S. Appl. No. 10/006,400, Apr. 27, 2010, Notice of Allowance.
U.S. Appl. No. 10/006,400, Aug. 2, 2010, Notice of Allowance.
U.S. Appl. No. 10/081,717, Sep. 29, 2003, Notice of Allowance.
U.S. Appl. No. 10/081,723, Sep. 29, 2004, Office Action.
U.S. Appl. No. 10/081,723, May 13, 2005, Notice of Allowance.
U.S. Appl. No. 10/081,725, Feb. 9, 2004, Notice of Allowance.
U.S. Appl. No. 10/081,725, Apr. 13, 2004, Office Action.
U.S. Appl. No. 10/081,726, Apr. 11, 2003, Notice of Allowance.
U.S. Appl. No. 10/081,726, Jun. 9, 2003, Notice of Allowance.
U.S. Appl. No. 10/147,774, Nov. 4, 2004, Office Action.
U.S. Appl. No. 10/147,774, May 4, 2005, Office Action.
U.S. Appl. No. 10/147,774, Oct. 18, 2005, Office Action.
U.S. Appl. No. 10/147,774, Apr. 18, 2007, Notice of Allowance.
U.S. Appl. No. 10/147,774, Sep. 27, 2007, Notice of Allowance.
U.S. Appl. No. 10/147,774, Feb. 4, 2008, Notice of Allowance.
U.S. Appl. No. 10/147,774, Jun. 30, 2008, Office Action.
U.S. Appl. No. 10/147,774, Mar. 18, 2009, Office Action.
U.S. Appl. No. 10/147,774, Oct. 26, 2009, Office Action.
U.S. Appl. No. 10/147,774, Jun. 8, 2010, Office Action.
U.S. Appl. No. 10/147,774, Dec. 2, 2010, Notice of Allowance.
U.S. Appl. No. 10/240,183, Jul. 27, 2004, Office Action.
U.S. Appl. No. 10/240,183, Dec. 17, 2004, Office Action.
U.S. Appl. No. 10/240,183, Mar. 9, 2005, Notice of Allowance.
U.S. Appl. No. 10/240,183, Aug. 11, 2006, Office Action.
U.S. Appl. No. 10/264,306, Feb. 9, 2005, Office Action.
U.S. Appl. No. 10/264,306, Oct. 4, 2005, Office Action.
U.S. Appl. No. 10/264,306, May 10, 2006, Notice of Allowance.
U.S. Appl. No. 10/264,306, Jul. 2, 2007, Notice of Allowance.
U.S. Appl. No. 10/264,306, Feb. 4, 2008, Notice of Allowance.
U.S. Appl. No. 10/264,306, Jun. 27, 2008, Office Action.
U.S. Appl. No. 10/264,306, Feb. 26, 2009, Office Action.
U.S. Appl. No. 10/264,306, Aug. 13, 2009, Office Action.
U.S. Appl. No. 10/264,306, Jan. 27, 2010, Office Action.
U.S. Appl. No. 10/264,306, Jun. 15, 2010, Office Action.
U.S. Appl. No. 10/264,306, Oct. 29, 2010, Notice of Allowance.
U.S. Appl. No. 10/335,075, Aug. 10, 2005, Office Action.
U.S. Appl. No. 10/335,075, Dec. 19, 2005, Office Action.
U.S. Appl. No. 10/335,075, Apr. 21, 2006, Office Action.
U.S. Appl. No. 10/335,075, Dec. 27, 2006, Notice of Allowance.
U.S. Appl. No. 10/356,214, Nov. 30, 2005, Office Action.
U.S. Appl. No. 10/356,214, Aug. 23, 2006, Office Action.
U.S. Appl. No. 10/356,214, Feb. 13, 2007, Office Action.
U.S. Appl. No. 10/356,214, Sep. 12, 2007, Office Action.
U.S. Appl. No. 10/356,214, Mar. 6, 2008, Office Action.
U.S. Appl. No. 10/356,214, Nov. 4, 2008, Office Action.
U.S. Appl. No. 10/356,214, Apr. 29, 2009, Office Action.
U.S. Appl. No. 10/356,214, Jan. 13, 2010, Notice of Allowance.
U.S. Appl. No. 10/356,214, May 13, 2010, Notice of Allowance.
U.S. Appl. No. 10/356,214, Sep. 3, 2010, Notice of Allowance.
U.S. Appl. No. 10/435,104, Jun. 10, 2004, Office Action.
U.S. Appl. No. 10/435,104, Sep. 21, 2004, Notice of Allowance.
U.S. Appl. No. 10/435,104, Jan. 3, 2006, Examiner's Amendment.
U.S. Appl. No. 10/435,104, May 16, 2006, Office Action.
U.S. Appl. No. 10/435,104, Dec. 28, 2006, Notice of Allowance.
U.S. Appl. No. 10/435,104, Jul. 10, 2007, Notice of Allowance.
U.S. Appl. No. 10/435,104, Aug. 2, 2007, Notice of Allowance.
U.S. Appl. No. 10/435,104, Oct. 26, 2007, Notice of Allowance.
U.S. Appl. No. 10/435,104, Nov. 14, 2007, Notice of Allowance.
U.S. Appl. No. 10/435,104, Apr. 4, 2008, Notice of Allowance.
U.S. Appl. No. 10/435,104, Sep. 26, 2008, Notice of Allowance.
U.S. Appl. No. 10/435,104, Dec. 22, 2008, Notice of Allowance.
U.S. Appl. No. 10/435,104, Jul. 23, 2009, Notice of Allowance.
U.S. Appl. No. 10/435,104, Jan. 20, 2010, Notice of Allowance.
U.S. Appl. No. 10/435,104, Jun. 2, 2010, Office Action.
U.S. Appl. No. 10/435,104, Oct. 5, 2010, Notice of Allowance.
U.S. Appl. No. 10/455,768, Nov. 16, 2004, Office Action.
U.S. Appl. No. 10/455,768, Apr. 6, 2005, Notice of Allowance.
U.S. Appl. No. 10/486,067, Jan. 10, 2006, Office Action.
U.S. Appl. No. 10/486,067, Sep. 20, 2006, Notice of Allowance.
U.S. Appl. No. 10/486,070, Apr. 20, 2005, Office Action.
U.S. Appl. No. 10/486,070, Aug. 10, 2005, Office Action.
U.S. Appl. No. 10/486,070, Oct. 18, 2005, Notice of Allowance.
U.S. Appl. No. 10/517,004, Aug. 13, 2007, Office Action.
U.S. Appl. No. 10/517,004, Jan. 30, 2008, Office Action.
U.S. Appl. No. 10/517,004, Aug. 13, 2008, Notice of Allowance.
U.S. Appl. No. 10/517,004, Feb. 10, 2009, Notice of Allowance.
U.S. Appl. No. 10/517,004, Mar. 24, 2009, Notice of Allowance.
U.S. Appl. No. 10/517,004, Jun. 26, 2009, Notice of Allowance.
U.S. Appl. No. 10/517,004, Jan. 11, 2010, Notice of Allowance.
U.S. Appl. No. 10/517,004, Apr. 23, 2010, Notice of Allowance.
U.S. Appl. No. 10/517,004, Aug. 3, 2010, Notice of Allowance.
U.S. Appl. No. 10/519,778, Feb. 23, 2006, Office Action.
U.S. Appl. No. 10/519,778, May 31, 2006, Notice of Allowance.
U.S. Appl. No. 10/541,083, Oct. 16, 2007, Office Action.
U.S. Appl. No. 10/541,083, Oct. 31, 2007, Office Action.
U.S. Appl. No. 10/541,083, May 5, 2008, Office Action.
U.S. Appl. No. 10/541,083, Sep. 19, 2008, Notice of Allowance.
U.S. Appl. No. 10/541,083, Dec. 29, 2008, Notice of Allowance.
U.S. Appl. No. 10/541,083, Apr. 16, 2009, Notice of Allowance.
U.S. Appl. No. 10/541,083, Sep. 30, 2009, Notice of Allowance.
U.S. Appl. No. 10/541,083, Feb. 5, 2010, Notice of Allowance.
U.S. Appl. No. 10/541,083, May 10, 2010, Notice of Allowance.
U.S. Appl. No. 10/541,083, Aug. 17, 2010, Notice of Allowance.
U.S. Appl. No. 10/616,832, Jun. 30, 2006, Office Action.
U.S. Appl. No. 10/616,832, Oct. 20, 2006, Office Action.
U.S. Appl. No. 10/616,832, May 29, 2007, Office Action.
U.S. Appl. No. 10/616,832, Jan. 22, 2008, Office Action.
U.S. Appl. No. 10/616,832, Sep. 17, 2008, Office Action.
U.S. Appl. No. 10/616,832, Jul. 21, 2009, Office Action.
U.S. Appl. No. 10/616,832, Jan. 11, 2010, Notice of Allowance.
U.S. Appl. No. 10/616,832, May 12, 2010, Notice of Allowance.
U.S. Appl. No. 10/616,832, Sep. 20, 2010, Notice of Allowance.
U.S. Appl. No. 10/617,090, Mar. 22, 2005, Office Action.
U.S. Appl. No. 10/617,090, Jul. 6, 2005, Notice of Allowance.
U.S. Appl. No. 10/617,090, Oct. 5, 2005, Notice of Allowance.
U.S. Appl. No. 10/638,115, Sep. 22, 2006, Office Action.
U.S. Appl. No. 10/638,115, Jan. 31, 2007, Office Action.
U.S. Appl. No. 10/638,115, Sep. 18, 2007, Office Action.
U.S. Appl. No. 10/638,115, Feb. 7, 2008, Office Action.
U.S. Appl. No. 10/638,115, Oct. 29, 2008, Office Action.
U.S. Appl. No. 10/638,115, May 7, 2009, Notice of Allowance.
U.S. Appl. No. 10/638,115, Dec. 1, 2009, Notice of Allowance.
U.S. Appl. No. 10/638,115, Apr. 2, 2010, Notice of Allowance.
U.S. Appl. No. 10/638,115, Aug. 13, 2010, Notice of Allowance.
U.S. Appl. No. 10/667,144, Sep. 19, 2006, Office Action.
U.S. Appl. No. 10/667,144, May 2, 2007, Office Action.
U.S. Appl. No. 10/667,144, Nov. 19, 2007, Office Action.
U.S. Appl. No. 10/667,144, Dec. 5, 2007, Office Action.
U.S. Appl. No. 10/667,144, May 12, 2008, Office Action.
U.S. Appl. No. 10/667,144, Mar. 24, 2009, Office Action.
U.S. Appl. No. 10/667,144, Nov. 23, 2009, Office Action.

(56) References Cited

OTHER PUBLICATIONS

U.S. Appl. No. 10/667,144, Jun. 22, 2010, Office Action.
U.S. Appl. No. 10/667,144, Jun. 6, 2011, Office Action.
U.S. Appl. No. 10/667,144, Oct. 28, 2011, Notice of Allowance.
U.S. Appl. No. 10/669,313, Oct. 31, 2005, Office Action.
U.S. Appl. No. 10/669,313, Jan. 11, 2006, Notice of Allowance.
U.S. Appl. No. 10/669,313, Jun. 28, 2006, Notice of Allowance.
U.S. Appl. No. 10/682,459, Sep. 15, 2006, Office Action.
U.S. Appl. No. 10/682,459, Apr. 18, 2007, Office Action.
U.S. Appl. No. 10/682,459, Apr. 2, 2008, Office Action.
U.S. Appl. No. 10/682,459, Dec. 4, 2008, Office Action.
U.S. Appl. No. 10/682,459, Jun. 10, 2009, Office Action.
U.S. Appl. No. 10/682,459, Dec. 23, 2009, Office Action.
U.S. Appl. No. 10/682,459, Apr. 28, 2010, Office Action.
U.S. Appl. No. 10/682,459, Oct. 12, 2010, Office Action.
U.S. Appl. No. 10/682,459, Apr. 1, 2011, Notice of Allowance.
U.S. Appl. No. 10/786,444, Oct. 30, 2006, Office Action.
U.S. Appl. No. 10/786,444, Apr. 17, 2007, Office Action.
U.S. Appl. No. 10/786,444, Aug. 31, 2007, Office Action.
U.S. Appl. No. 10/786,444, Apr. 24, 2008, Office Action.
U.S. Appl. No. 10/786,444, Oct. 17, 2008, Office Action.
U.S. Appl. No. 10/786,444, Jun. 18, 2009, Office Action.
U.S. Appl. No. 10/786,444, Jan. 14, 2010, Office Action.
U.S. Appl. No. 10/786,444, Jul. 11, 2013, Notice of Allowance.
U.S. Appl. No. 10/787,073, Nov. 30, 2006, Office Action.
U.S. Appl. No. 10/787,073, Sep. 5, 2007, Office Action.
U.S. Appl. No. 10/787,073, Feb. 22, 2008, Office Action.
U.S. Appl. No. 10/787,073, Nov. 12, 2008, Office Action.
U.S. Appl. No. 10/787,073, Aug. 13, 2009, Office Action.
U.S. Appl. No. 10/787,073, Feb. 17, 2010, Notice of Allowance.
U.S. Appl. No. 10/787,073, Aug. 25, 2010, Notice of Allowance.
U.S. Appl. No. 10/908,721, Oct. 19, 2006, Office Action.
U.S. Appl. No. 10/908,721, Aug. 10, 2007, Office Action.
U.S. Appl. No. 10/908,721, Jan. 25, 2008, Office Action.
U.S. Appl. No. 10/908,721, Nov. 25, 2008, Office Action.
U.S. Appl. No. 10/908,721, Jun. 23, 2009, Office Action.
U.S. Appl. No. 10/908,721, Feb. 2, 2010, Office Action.
U.S. Appl. No. 10/908,721, Jul. 18, 2013, Notice of Allowance.
U.S. Appl. No. 11/048,503, Mar. 13, 2009, Office Action.
U.S. Appl. No. 11/048,503, Jun. 26, 2009, Office Action.
U.S. Appl. No. 11/048,503, Jan. 11, 2010, Notice of Allowance.
U.S. Appl. No. 11/048,503, Apr. 26, 2010, Notice of Allowance.
U.S. Appl. No. 11/048,503, Jul. 30, 2010, Notice of Allowance.
U.S. Appl. No. 11/113,549, Feb. 6, 2007, Office Action.
U.S. Appl. No. 11/113,549, May 30, 2007, Office Action.
U.S. Appl. No. 11/113,549, Nov. 9, 2007, Office Action.
U.S. Appl. No. 11/113,549, Apr. 16, 2008, Office Action.
U.S. Appl. No. 11/113,549, Jul. 21, 2009, Office Action.
U.S. Appl. No. 11/113,549, Jul. 6, 2010, Office Action.
U.S. Appl. No. 11/113,549, Jan. 4, 2011, Office Action.
U.S. Appl. No. 11/113,549, Mar. 14, 2014, Notice of Allowance.
U.S. Appl. No. 11/152,562, May 13, 2008, Office Action.
U.S. Appl. No. 11/152,562, Feb. 13, 2009, Office Action.
U.S. Appl. No. 11/152,562, Jul. 6, 2009, Office Action.
U.S. Appl. No. 11/152,562, Mar. 31, 2010, Office Action.
U.S. Appl. No. 11/152,562, Sep. 16, 2010, Notice of Allowance.
U.S. Appl. No. 11/198,811, Aug. 26, 2008, Office Action.
U.S. Appl. No. 11/198,811, Apr. 6, 2009, Office Action.
U.S. Appl. No. 11/198,811, Sep. 22, 2009, Office Action.
U.S. Appl. No. 11/198,811, Jun. 29, 2010, Notice of Allowance.
U.S. Appl. No. 11/344,793, Jan. 22, 2009, Office Action.
U.S. Appl. No. 11/344,868, Mar. 25, 2009, Office Action.
U.S. Appl. No. 11/344,891, Apr. 29, 2008, Office Action.
U.S. Appl. No. 11/344,891, Dec. 8, 2008, Office Action.
U.S. Appl. No. 11/344,891, Feb. 26, 2009, Office Action.
U.S. Appl. No. 11/344,891, Oct. 7, 2009, Office Action.
U.S. Appl. No. 11/344,891, May 7, 2010, Office Action.
U.S. Appl. No. 11/344,891, Jan. 22, 2013, Notice of Allowance.
U.S. Appl. No. 11/390,586, Jun. 24, 2009, Office Action.
U.S. Appl. No. 11/390,586, Jul. 6, 2010, Office Action.
U.S. Appl. No. 11/390,586, May 3, 2012, Notice of Allowance.
U.S. Appl. No. 11/396,141, May 22, 2009, Office Action.
U.S. Appl. No. 11/396,141, Aug. 26, 2009, Office Action.
U.S. Appl. No. 11/396,141, May 4, 2010, Office Action.
U.S. Appl. No. 11/396,141, Apr. 30, 2013, Office Action.
U.S. Appl. No. 11/396,141, Aug. 21, 2013, Office Action.
U.S. Appl. No. 11/396,141, Nov. 4, 2013, Notice of Allowance.
U.S. Appl. No. 11/396,731, Feb. 13, 2009, Office Action.
U.S. Appl. No. 11/396,731, May 22, 2009, Office Action.
U.S. Appl. No. 11/396,731, Jun. 29, 2010, Office Action.
U.S. Appl. No. 11/396,731, Mar. 22, 2011, Office Action.
U.S. Appl. No. 11/396,731, Sep. 1, 2011, Office Action.
U.S. Appl. No. 11/406,203, May 14, 2007, Office Action.
U.S. Appl. No. 11/406,203, Jan. 29, 2008, Notice of Allowance.
U.S. Appl. No. 11/406,203, May 23, 2008, Notice of Allowance.
U.S. Appl. No. 11/406,203, Sep. 22, 2008, Notice of Allowance.
U.S. Appl. No. 11/406,203, Mar. 3, 2009, Office Action.
U.S. Appl. No. 11/406,203, Sep. 16, 2009, Office Action.
U.S. Appl. No. 11/406,203, Jun. 18, 2010, Notice of Allowance.
U.S. Appl. No. 11/411,925, Jun. 6, 2007, Office Action.
U.S. Appl. No. 11/411,925, Feb. 5, 2008, Office Action.
U.S. Appl. No. 11/411,925, Jan. 12, 2009, Office Action.
U.S. Appl. No. 11/411,925, Sep. 10, 2009, Office Action.
U.S. Appl. No. 11/411,925, Oct. 1, 2013, Office Action.
U.S. Appl. No. 11/411,925, Feb. 5, 2014, Notice of Allowance.
U.S. Appl. No. 11/427,297, Jan. 30, 2009, Office Action.
U.S. Appl. No. 11/427,297, Sep. 15, 2009, Office Action.
U.S. Appl. No. 11/427,297, Sep. 15, 2010, Office Action.
U.S. Appl. No. 11/427,297, Mar. 21, 2011, Office Action.
U.S. Appl. No. 11/427,297, Jun. 26, 2012, Notice of Allowance.
U.S. Appl. No. 11/427,309, May 28, 2008, Office Action.
U.S. Appl. No. 11/427,309, Jan. 2, 2009, Office Action.
U.S. Appl. No. 11/427,309, Apr. 20, 2009, Office Action.
U.S. Appl. No. 11/427,309, Nov. 6, 2009, Office Action.
U.S. Appl. No. 11/427,309, Apr. 26, 2010, Office Action.
U.S. Appl. No. 11/427,309, Nov. 15, 2010, Office Action.
U.S. Appl. No. 11/427,309, Jun. 7, 2013, Notice of Allowance.
U.S. Appl. No. 11/455,993, Feb. 17, 2009, Office Action.
U.S. Appl. No. 11/455,993, Dec. 16, 2009, Office Action.
U.S. Appl. No. 11/455,993, Jan. 29, 2014, Office Action.
U.S. Appl. No. 11/455,993, Aug. 11, 2014, Notice of Allowance.
U.S. Appl. No. 11/455,993, Dec. 17, 2014, Issue Notification.
U.S. Appl. No. 11/532,325, Feb. 23, 2009, Office Action.
U.S. Appl. No. 11/532,325, Jun. 17, 2009, Office Action.
U.S. Appl. No. 11/532,325, Jan. 5, 2010, Office Action.
U.S. Appl. No. 11/532,325, Jul. 17, 2013, Office Action.
U.S. Appl. No. 11/532,325, Dec. 2, 2013, Office Action.
U.S. Appl. No. 11/532,325, Jan. 16, 2015, Notice of Allowance.
U.S. Appl. No. 11/532,576, Mar. 1, 2010, Office Action.
U.S. Appl. No. 11/532,576, Apr. 23, 2010, Office Action.
U.S. Appl. No. 11/532,576, Oct. 13, 2010, Notice of Allowance.
U.S. Appl. No. 11/674,930, Jan. 8, 2009, Office Action.
U.S. Appl. No. 11/674,930, Jun. 4, 2009, Office Action.
U.S. Appl. No. 11/674,930, Jan. 8, 2010, Office Action.
U.S. Appl. No. 11/674,930, Apr. 3, 2014, Notice of Allowance.
U.S. Appl. No. 11/675,462, Dec. 10, 2009, Office Action.
U.S. Appl. No. 11/675,462, Aug. 31, 2010, Office Action.
U.S. Appl. No. 11/675,462, Aug. 3, 2011, Office Action.
U.S. Appl. No. 11/675,462, Dec. 22, 2011, Notice of Allowance.
U.S. Appl. No. 11/744,089, Nov. 26, 2008, Office Action.
U.S. Appl. No. 11/744,089, Aug. 14, 2009, Office Action.
U.S. Appl. No. 11/744,089, Aug. 8, 2012, Office Action.
U.S. Appl. No. 11/744,089, Apr. 15, 2013, Office Action.
U.S. Appl. No. 11/744,089, Aug. 8, 2013, Notice of Allowance.
U.S. Appl. No. 11/757,108, Nov. 25, 2009, Office Action.
U.S. Appl. No. 11/767,818, Dec. 24, 2009, Office Action.
U.S. Appl. No. 11/767,818, Mar. 22, 2010, Office Action.
U.S. Appl. No. 11/767,818, Sep. 30, 2010, Office Action.
U.S. Appl. No. 11/767,818, Feb. 16, 2011, Office Action.
U.S. Appl. No. 11/767,818, Feb. 3, 2012, Notice of Allowance.
U.S. Appl. No. 11/852,190, Jun. 24, 2010, Office Action.
U.S. Appl. No. 11/852,190, Nov. 1, 2010, Office Action.
U.S. Appl. No. 11/852,190, Mar. 2, 2011, Office Action.

(56) References Cited

OTHER PUBLICATIONS

U.S. Appl. No. 11/852,190, Apr. 24, 2013, Office Action.
U.S. Appl. No. 11/852,190, Nov. 26, 2013, Office Action.
U.S. Appl. No. 11/852,190, Feb. 12, 2014, Notice of Allowance.
U.S. Appl. No. 11/958,281, Sep. 2, 2010, Office Action.
U.S. Appl. No. 11/958,281, Oct. 8, 2010, Office Action.
U.S. Appl. No. 11/958,281, Mar. 10, 2011, Office Action.
U.S. Appl. No. 11/958,295, Aug. 27, 2009, Office Action.
U.S. Appl. No. 11/958,295, May 25, 2010, Office Action.
U.S. Appl. No. 11/958,295, Jun. 13, 2014, Notice of Allowance.
U.S. Appl. No. 11/959,334, Aug. 19, 2009, Office Action.
U.S. Appl. No. 11/959,334, Jan. 12, 2010, Notice of Allowance.
U.S. Appl. No. 11/959,334, Apr. 14, 2010, Notice of Allowance.
U.S. Appl. No. 11/959,334, Jul. 23, 2010, Notice of Allowance.
U.S. Appl. No. 12/106,928, Jan. 23, 2009, Office Action.
U.S. Appl. No. 12/106,928, Oct. 5, 2009, Office Action.
U.S. Appl. No. 12/106,928, May 10, 2010, Office Action.
U.S. Appl. No. 12/106,928, Oct. 25, 2010, Office Action.
U.S. Appl. No. 12/106,928, Jun. 28, 2013, Office Action.
U.S. Appl. No. 12/106,928, Dec. 2, 2013, Office Action.
U.S. Appl. No. 12/106,928, Mar. 25, 2014, Advisory Action.
U.S. Appl. No. 12/106,928, Oct. 3, 2014, Notice of Allowance.
U.S. Appl. No. 12/106,928, Jan. 27, 2015, Issue Notification.
U.S. Appl. No. 12/106,937, Mar. 30, 2009, Office Action.
U.S. Appl. No. 12/106,937, Nov. 18, 2009, Office Action.
U.S. Appl. No. 12/106,937, Jun. 28, 2013, Office Action.
U.S. Appl. No. 12/106,937, Jan. 22, 2014, Office Action.
U.S. Appl. No. 12/113,851, Apr. 27, 2010, Office Action.
U.S. Appl. No. 12/113,851, Jun. 24, 2010, Office Action.
U.S. Appl. No. 12/113,851, Dec. 16, 2010, Office Action.
U.S. Appl. No. 12/113,851, Apr. 27, 2011, Office Action.
U.S. Appl. No. 12/113,851, Mar. 29, 2012, Office Action.
U.S. Appl. No. 12/113,851, Mar. 17, 2014, Office Action.
U.S. Appl. No. 12/113,851, Aug. 21, 2014, Office Action.
U.S. Appl. No. 12/114,031, Oct. 5, 2010, Office Action.
U.S. Appl. No. 12/114,031, Nov. 22, 2010, Office Action.
U.S. Appl. No. 12/114,031, May 11, 2011, Office Action.
U.S. Appl. No. 12/114,031, Aug. 2, 2011, Office Action.
U.S. Appl. No. 12/114,031, Mar. 6, 2012, Office Action.
U.S. Appl. No. 12/114,031, Mar. 10, 2014, Office Action.
U.S. Appl. No. 12/114,091, Oct. 27, 2010, Office Action.
U.S. Appl. No. 12/114,091, Dec. 17, 2010, Office Action.
U.S. Appl. No. 12/114,091, Jul. 7, 2011, Office Action.
U.S. Appl. No. 12/114,091, Apr. 5, 2012, Office Action.
U.S. Appl. No. 12/114,091, Nov. 8, 2012, Office Action.
U.S. Appl. No. 12/122,603, Mar. 3, 2011, Office Action.
U.S. Appl. No. 12/122,603, Apr. 22, 2011, Office Action.
U.S. Appl. No. 12/122,603, Sep. 23, 2011, Office Action.
U.S. Appl. No. 12/122,603, Nov. 20, 2013, Office Action.
U.S. Appl. No. 12/122,603, Apr. 30, 2014, Office Action.
U.S. Appl. No. 12/135,858, Jul. 13, 2011, Office Action.
U.S. Appl. No. 12/135,858, Feb. 16, 2012, Office Action.
U.S. Appl. No. 12/143,020, May 11, 2011, Office Action.
U.S. Appl. No. 12/143,020, Aug. 31, 2011, Office Action.
U.S. Appl. No. 12/143,020, Feb. 23, 2012, Notice of Allowance.
U.S. Appl. No. 12/338,977, Jan. 19, 2012, Office Action.
U.S. Appl. No. 12/338,977, Jul. 11, 2012, Office Action.
U.S. Appl. No. 12/338,977, Nov. 28, 2012, Office Action.
U.S. Appl. No. 12/338,977, Jun. 19, 2013, Office Action.
U.S. Appl. No. 12/393,877, Sep. 29, 2011, Office Action.
U.S. Appl. No. 12/393,877, Dec. 13, 2011, Office Action.
U.S. Appl. No. 12/393,877, May 21, 2012, Office Action.
U.S. Appl. No. 12/393,877, Aug. 4, 2014, Notice of Allowance.
U.S. Appl. No. 12/402,398, Mar. 9, 2010, Office Action.
U.S. Appl. No. 12/402,398, May 20, 2010, Office Action.
U.S. Appl. No. 12/402,398, Jan. 24, 2011, Office Action.
U.S. Appl. No. 12/402,398, Sep. 20, 2012, Office Action.
U.S. Appl. No. 12/402,398, Mar. 13, 2013, Notice of Allowance.
U.S. Appl. No. 12/403,256, Dec. 16, 2009, Office Action.
U.S. Appl. No. 12/403,256, Mar. 30, 2010, Office Action.
U.S. Appl. No. 12/403,256, Aug. 19, 2010, Notice of Allowance.
U.S. Appl. No. 12/403,277, Jul. 8, 2010, Office Action.
U.S. Appl. No. 12/403,277, Oct. 12, 2010, Office Action.
U.S. Appl. No. 12/403,277, Mar. 31, 2011, Office Action.
U.S. Appl. No. 12/403,277, Apr. 3, 2012, Office Action.
U.S. Appl. No. 12/403,277, Nov. 5, 2012, Office Action.
U.S. Appl. No. 12/403,277, Jan. 27, 2014, Office Action.
U.S. Appl. No. 12/403,277, Aug. 15, 2014, Office Action.
U.S. Appl. No. 12/481,377, Apr. 28, 2011, Office Action.
U.S. Appl. No. 12/481,377, Jun. 21, 2011, Office Action.
U.S. Appl. No. 12/481,377, Jan. 3, 2012, Office Action.
U.S. Appl. No. 12/481,377, Aug. 10, 2012, Notice of Allowance.
U.S. Appl. No. 12/548,274, Dec. 28, 2011, Office Action.
U.S. Appl. No. 12/548,274, Mar. 2, 2012, Office Action.
U.S. Appl. No. 12/548,274, Sep. 10, 2012, Office Action.
U.S. Appl. No. 12/548,274, Aug. 14, 2014, Office Action.
U.S. Appl. No. 12/608,769, Feb. 10, 2012, Office Action.
U.S. Appl. No. 12/608,769, Aug. 22, 2012, Office Action.
U.S. Appl. No. 12/608,769, Nov. 5, 2012, Notice of Allowance.
U.S. Appl. No. 12/608,773, Jun. 7, 2012, Office Action.
U.S. Appl. No. 12/608,773, Jul. 20, 2012, Office Action.
U.S. Appl. No. 12/608,773, Jan. 7, 2013, Office Action.
U.S. Appl. No. 12/608,773, Jul. 17, 2014, Office Action.
U.S. Appl. No. 12/642,319, Feb. 27, 2012, Office Action.
U.S. Appl. No. 12/642,319, Aug. 28, 2012, Office Action.
U.S. Appl. No. 12/642,319, Dec. 16, 2013, Office Action.
U.S. Appl. No. 12/642,319, May 27, 2014, Notice of Allowance.
U.S. Appl. No. 12/684,400, Feb. 13, 2012, Office Action.
U.S. Appl. No. 12/684,400, May 9, 2012, Office Action.
U.S. Appl. No. 12/684,400, Oct. 16, 2012, Office Action.
U.S. Appl. No. 12/684,470, Dec. 20, 2011, Office Action.
U.S. Appl. No. 12/684,470, Mar. 23, 2012, Office Action.
U.S. Appl. No. 12/684,470, Aug. 30, 2012, Office Action.
U.S. Appl. No. 12/684,470, Jun. 4, 2014, Office Action.
U.S. Appl. No. 12/684,470, Nov. 14, 2014, Office Action.
U.S. Appl. No. 12/684,542, Jan. 30, 2012, Office Action.
U.S. Appl. No. 12/684,542, Apr. 16, 2012, Office Action.
U.S. Appl. No. 12/684,542, Sep. 13, 2012, Office Action.
U.S. Appl. No. 12/684,542, Jun. 18, 2014, Office Action.
U.S. Appl. No. 12/684,542, Dec. 1, 2014, Office Action.
U.S. Appl. No. 12/684,562, Dec. 28, 2011, Office Action.
U.S. Appl. No. 12/684,562, Feb. 16, 2012, Office Action.
U.S. Appl. No. 12/684,562, Aug. 21, 2012, Office Action.
U.S. Appl. No. 12/684,562, Sep. 10, 2014, Office Action.
U.S. Appl. No. 12/684,569, Dec. 20, 2011, Office Action.
U.S. Appl. No. 12/684,569, Jan. 27, 2012, Office Action.
U.S. Appl. No. 12/684,569, Jul. 30, 2012, Office Action.
U.S. Appl. No. 12/684,569, Apr. 23, 2014, Office Action.
U.S. Appl. No. 12/688,065, Mar. 13, 2012, Office Action.
U.S. Appl. No. 12/688,065, Apr. 26, 2012, Office Action.
U.S. Appl. No. 12/688,065, Oct. 12, 2012, Office Action.
U.S. Appl. No. 12/688,065, Oct. 18, 2013, Office Action.
U.S. Appl. No. 12/688,065, Apr. 8, 2014, Office Action.
U.S. Appl. No. 12/724,304, Feb. 10, 2012, Office Action.
U.S. Appl. No. 12/724,304, Mar. 13, 2012, Interview Summary.
U.S. Appl. No. 12/724,304, Jul. 11, 2012, Notice of Allowance.
U.S. Appl. No. 12/848,642, Sep. 20, 2012, Office Action.
U.S. Appl. No. 12/848,642, Nov. 9, 2012, Office Action.
U.S. Appl. No. 12/848,642, Apr. 26, 2013, Office Action.
U.S. Appl. No. 12/848,642, Feb. 3, 2014, Notice of Allowance.
U.S. Appl. No. 12/850,242, Aug. 6, 2012, Office Action.
U.S. Appl. No. 12/850,242, Oct. 17, 2012, Office Action.
U.S. Appl. No. 12/850,242, Apr. 18, 2013, Office Action.
U.S. Appl. No. 12/850,242, Aug. 6, 2013, Notice of Allowance.
U.S. Appl. No. 12/897,358, Aug. 22, 2011, Office Action.
U.S. Appl. No. 12/897,358, Jan. 12, 2012, Notice of Allowance.
U.S. Appl. No. 12/897,358, Mar. 5, 2012, Notice of Allowance.
U.S. Appl. No. 12/941,809, Dec. 13, 2011, Office Action.
U.S. Appl. No. 12/941,809, Jan. 30, 2012, Office Action.
U.S. Appl. No. 12/941,809, Jun. 1, 2012, Office Action.
U.S. Appl. No. 12/941,809, Jul. 3, 2013, Office Action.
U.S. Appl. No. 12/941,809, Nov. 8, 2013, Office Action.
U.S. Appl. No. 12/941,809, Feb. 3, 2014, Notice of Allowance.

(56) References Cited

OTHER PUBLICATIONS

U.S. Appl. No. 12/945,646, Jan. 20, 2011, Office Action.
U.S. Appl. No. 12/945,646, Jul. 6, 2011, Office Action.
U.S. Appl. No. 12/945,646, Oct. 26, 2011, Office Action.
U.S. Appl. No. 12/945,646, Feb. 21, 2012, Notice of Allowance.
U.S. Appl. No. 12/950,628, Apr. 25, 2014, Notice of Allowance.
U.S. Appl. No. 12/955,859, May 26, 2011, Office Action.
U.S. Appl. No. 12/955,859, Jul. 21, 2011, Office Action.
U.S. Appl. No. 12/955,859, Dec. 15, 2011, Office Action.
U.S. Appl. No. 12/955,859, Aug. 6, 2012, Office Action.
U.S. Appl. No. 12/955,859, May 16, 2013, Office Action.
U.S. Appl. No. 12/955,859, Aug. 1, 2013, Notice of Allowance.
U.S. Appl. No. 12/961,331, Dec. 4, 2012, Office Action.
U.S. Appl. No. 12/961,331, Feb. 1, 2013, Office Action.
U.S. Appl. No. 12/961,331, Jul. 3, 2013, Office Action.
U.S. Appl. No. 12/961,331, Sep. 20, 2013, Advisory Action.
U.S. Appl. No. 12/961,331, Apr. 25, 2014, Notice of Allowance.
U.S. Appl. No. 12/966,923, Feb. 3, 2012, Notice of Allowance.
U.S. Appl. No. 12/973,204, Mar. 7, 2012, Notice of Allowance.
U.S. Appl. No. 12/987,792, Mar. 13, 2012, Office Action.
U.S. Appl. No. 12/987,792, Sep. 17, 2012, Office Action.
U.S. Appl. No. 12/987,792, Jan. 21, 2014, Office Action.
U.S. Appl. No. 12/987,792, Jun. 11, 2014, Office Action.
U.S. Appl. No. 12/987,792, Aug. 25, 2014, Notice of Allowance.
U.S. Appl. No. 13/026,989, Sep. 16, 2011, Office Action.
U.S. Appl. No. 13/026,989, Jun. 8, 2012, Office Action.
U.S. Appl. No. 13/026,989, Aug. 23, 2013, Office Action.
U.S. Appl. No. 13/028,041, Jan. 4, 2013, Office Action.
U.S. Appl. No. 13/028,041, Feb. 26, 2013, Office Action.
U.S. Appl. No. 13/028,041, Aug. 21, 2013, Notice of Allowance.
U.S. Appl. No. 13/030,922, Dec. 18, 2012, Office Action.
U.S. Appl. No. 13/030,922, Jan. 31, 2013, Office Action.
U.S. Appl. No. 13/030,922, Jul. 18, 2013, Office Action.
U.S. Appl. No. 13/030,922, Jan. 8, 2014, Notice of Allowance.
U.S. Appl. No. 13/039,087, Jul. 17, 2012, Office Action.
U.S. Appl. No. 13/039,087, Nov. 6, 2012, Notice of Allowance.
U.S. Appl. No. 13/111,371, Oct. 12, 2012, Office Action.
U.S. Appl. No. 13/111,371, Dec. 18, 2012, Office Action.
U.S. Appl. No. 13/111,371, Jun. 6, 2013, Notice of Allowance.
U.S. Appl. No. 13/112,618, Mar. 29, 2013, Office Action.
U.S. Appl. No. 13/112,618, Jun. 7, 2013, Office Action.
U.S. Appl. No. 13/112,618, Nov. 20, 2013, Office Action.
U.S. Appl. No. 13/112,618, Dec. 15, 2014, Office Action.
U.S. Appl. No. 13/112,631, Mar. 29, 2013, Office Action.
U.S. Appl. No. 13/112,631, Jun. 26, 2013, Office Action.
U.S. Appl. No. 13/112,631, Dec. 2, 2013, Office Action.
U.S. Appl. No. 13/112,631, Nov. 20, 2014, Office Action.
U.S. Appl. No. 13/153,594, Jan. 29, 2013, Office Action.
U.S. Appl. No. 13/153,594, May 29, 2013, Office Action.
U.S. Appl. No. 13/153,594, Oct. 16, 2013, Notice of Allowance.
U.S. Appl. No. 13/222,899, Jan. 10, 2014, Office Action.
U.S. Appl. No. 13/222,899, Jul. 31, 2014, Office Action.
U.S. Appl. No. 13/308,227, Apr. 10, 2013, Office Action.
U.S. Appl. No. 13/308,227, Sep. 11, 2013, Office Action.
U.S. Appl. No. 13/488,233, Feb. 5, 2013, Notice of Allowance.
U.S. Appl. No. 13/490,143, Jan. 4, 2013, Office Action.
U.S. Appl. No. 13/490,143, Apr. 29, 2013, Notice of Allowance.
U.S. Appl. No. 13/525,839, Apr. 1, 2013, Office Action.
U.S. Appl. No. 13/525,839, Jul. 15, 2013, Notice of Allowance.
U.S. Appl. No. 13/615,547, Jan. 18, 2013, Office Action.
U.S. Appl. No. 13/615,547, Apr. 12, 2013, Notice of Allowance.
U.S. Appl. No. 13/791,829, May 29, 2013, Office Action.
U.S. Appl. No. 13/791,829, Oct. 8, 2013, Notice of Allowance.
U.S. Appl. No. 13/898,202, Jan. 3, 2014, Office Action.
U.S. Appl. No. 13/898,202, Aug. 21, 2014, Office Action.
U.S. Appl. No. 14/017,039, Jan. 23, 2015, Office Action.
U.S. Appl. No. 29/296,370, Aug. 18, 2008, Office Action.
U.S. Appl. No. 29/296,370, Dec. 2, 2008, Notice of Allowance.
U.S. Appl. No. 29/296,370, Apr. 1, 2009, Notice of Allowance.
U.S. Appl. No. 14/839,658, filed Aug. 31, 2015, Cummins et al.
U.S. Appl. No. 14/855,080, filed Sep. 15, 2015, Voss et al.
Carpenter et al, Midterm results of the multicenter trial of the Powerlink bifurcated system for endovascular aortic aneurysm repair, Journal of Vascular Surgery, vol. 40, No. 5, Nov. 2004, p. 849-859.e5.
Eisenack et al, Percutaneous Endovascular Aortic Aneurysm Repair: A Prospective Evaluation of Safety, Efficiency, and Risk Factors, Journal of Endovascular Ther., 2009, vol. 16, p. 708-713.
Greenhalgh et al, Endovascular versus open repair of abdominal aortic aneurysm, The New England journal of medicine, vol. 362, No. 20, 2010, p. 1863-1871.
Grossman, W., Cardiac Catheterization and Angiography, 3rd Ed., Lea & Febiger, Philadelphia, pp. 1-49, 52-247. 1986.
Howell et al, Percutaneous Repair of Abdominal Aortic Aneurysms Using the aneuRx Stent Graft and the Percutaneous Vascular Surgery Device, Catheterization and cardiovascular interventions, vol. 55, No. 3, 2002, p. 281-287.
Jean-Baptiste et al., Percutaneous closure devices for endovascular repair of infrarenal abdominal aortic aneurysms: a prospective, non-randomized comparative study, European Journal of Vascular and Endovascular Surgery, vol. 35, No. 4, 2008, p. 422-428.
Krajcer and Gregoric, Totally percutaneous aortic aneurysm repair: methods and outcomes using the fully integrated IntuiTrak endovascular system, The Journal of cardiovascular surgery, vol. 51, No. 4, 2010, p. 493-501.
Lederle et al, Outcomes following endovascular vs open repair of abdominal aortic aneurysm: a randomized trial, Jama, vol. 302, No. 14, 2009, p. 1535-1542.
Lee et al, Total percutaneous access for endovascular aortic aneurysm repair ("Preclose" technique), Journal of vascular surgery, vol. 45, No. 6, 2007, p. 1095-1101.
Malkawi et al, Percutaneous access for endovascular aneurysm repair: a systematic review, European Journal of Vascular and Endovascular Surgery, vol. 39, No. 6, 2010, p. 676-682.
Morasch et al, Percutaneous repair of abdominal aortic aneurysm, Journal of vascular surgery, vol. 40, No. 1, 2004, p. 12-16.
Rachel et al, Percutaneous endovascular abdominal aortic aneurysm repair, Annals of vascular surgery, vol. 16, No. 1, 2002, p. 43-49.
Starnes et al, Totally percutaneous aortic aneurysm repair: experience and prudence, Journal of vascular surgery, vol. 43, No. 2, 2006, p. 270-276.
Teh et al, Use of the percutaneous vascular surgery device for closure of femoral access sites during endovascular aneurysm repair: lessons from our experience, European Journal of Vascular and Endovascular Surgery, vol. 22, No. 5, 2001, p. 418-423.
Torsello et al, Endovascular suture versus cutdown for endovascular aneurysm repair: a prospective randomized pilot study, Journal of vascular surgery, vol. 38, No. 1, 2003, p. 78-82.
Traul et al, Percutaneous endovascular repair of infrarenal abdominal aortic aneurysms: a feasibility study, Journal of vascular surgery, vol. 32, No. 4, 2000, p. 770-776.
Watelet et al, Percutaneous repair of aortic aneurysms: a prospective study of suture-mediated closure devices, European journal of vascular and endovascular surgery, vol. 32, No. 3, 2006, p. 261-265.
U.S. Appl. No. 11/396,731, Feb. 12, 2015, Office Action.
U.S. Appl. No. 11/396,731, Jul. 9, 2015, Notice of Allowance.
U.S. Appl. No. 12/106,937, Mar. 5, 2015, Notice of Allowance.
U.S. Appl. No. 12/113,851, Feb. 20, 2015, Notice of Allowance.
U.S. Appl. No. 12/114,091, Feb. 12, 2015, Office Action.
U.S. Appl. No. 12/114,091, Jul. 23, 2015, Office Action.
U.S. Appl. No. 12/122,603, Apr. 9, 2015, Office Action.
U.S. Appl. No. 12/122,603, Sep. 23, 2015, Notice of Allowance.
U.S. Appl. No. 12/608,773, Mar. 12, 2015, Office Action.
U.S. Appl. No. 12/608,773, Sep. 17, 2015, Notice of Allowance.
U.S. Appl. No. 12/684,400, Feb. 23, 2015, Office Action.
U.S. Appl. No. 12/684,400, Jul. 28, 2015, Notice of Allowance.
U.S. Appl. No. 12/684,470, Aug. 26, 2015, Office Action.
U.S. Appl. No. 12/684,562, Feb. 17, 2015, Notice of Allowance.
U.S. Appl. No. 13/112,618, May 18, 2015, Office Action.
U.S. Appl. No. 13/112,631, Apr. 15, 2015, Office Action.
U.S. Appl. No. 13/222,899, Apr. 1, 2015, Office Action.
U.S. Appl. No. 13/222,899, Aug. 5, 2015, Office Action.
U.S. Appl. No. 13/308,227, Jul. 14, 2015, Office Action.

(56) References Cited

OTHER PUBLICATIONS

U.S. Appl. No. 13/725,589, Sep. 17, 2015, Office Action.
U.S. Appl. No. 13/791,846, Jun. 4, 2015, Office Action.
U.S. Appl. No. 13/791,846, Oct. 27, 2015, Notice of Allowance.
U.S. Appl. No. 13/837,801, Dec. 16, 2015, Office Action.
U.S. Appl. No. 13/898,202, Feb. 10, 2015, Notice of Allowance.
U.S. Appl. No. 13/908,796, Jul. 21, 2015, Office Action.
U.S. Appl. No. 13/908,796, Nov. 6, 2015, Notice of Allowance.
U.S. Appl. No. 14/017,039, Jun. 10, 2015, Office Action.
U.S. Appl. No. 14/017,039, Oct. 27, 2015, Office Action.
U.S. Appl. No. 14/023,428, Jul. 27, 2015, Office Action.
U.S. Appl. No. 14/077,007, Jul. 27, 2015, Office Action.
U.S. Appl. No. 14/246,926, Aug. 5, 2015, Office Action.
U.S. Appl. No. 14/246,926, Nov. 23, 2015, Office Action.
U.S. Appl. No. 14/246,973, Aug. 3, 2015, Office Action.
U.S. Appl. No. 14/246,973, Nov. 24, 2015, Office Action.
U.S. Appl. No. 14/323,753, Nov. 3, 2015, Office Action.
U.S. Appl. No. 14/466,576, Jul. 8, 2015, Office Action.
U.S. Appl. No. 14/466,576, Dec. 15, 2015, Notice of Allowance.
U.S. Appl. No. 14/928,950, filed Oct. 30, 2015, Voss.
U.S. Appl. No. 15/056,281, filed Feb. 29, 2016, Palermo et al.
U.S. Appl. No. 15/069,230, filed Mar. 14, 2016, Kokish.
U.S. Appl. No. 15/005,780, filed Jan. 25, 2016, Mehl.
U.S. Appl. No. 12/114,091, Apr. 6, 2016, Notice of Allowance.
U.S. Appl. No. 12/684,470, Jan. 21, 2016, Office Action.
U.S. Appl. No. 12/684,470, Apr. 22, 2016, Notice of Allowance.
U.S. Appl. No. 13/112,618, Jan. 29, 2016, Office Action.
U.S. Appl. No. 13/222,899, Jan. 7, 2016, Notice of Allowance.
U.S. Appl. No. 13/308,227, Feb. 1, 2016, Notice of Allowance.
U.S. Appl. No. 13/308,227, Apr. 20, 2016, Issue Notification.
U.S. Appl. No. 13/725,589, Mar. 18, 2016, Notice of Allowance.
U.S. Appl. No. 14/017,039, Apr. 4, 2016, Notice of Allowance.
U.S. Appl. No. 14/023,428, Feb. 9, 2016, Office Action.
U.S. Appl. No. 14/077,007, Jan. 29, 2016, Office Action.
U.S. Appl. No. 14/312,339, Jan. 22, 2016, Office Action.
U.S. Appl. No. 14/323,753, Apr. 15, 2016, Notice of Allowance.
U.S. Appl. No. 15/131,786, filed Apr. 18, 2016, Roorda et al.
U.S. Appl. No. 15/142,106, filed Apr. 29, 2016, Voss.
U.S. Appl. No. 12/114,091, Jul. 13, 2016, Issue Notification.
U.S. Appl. No. 13/112,618, Jul. 6, 2016, Notice of Allowance.
U.S. Appl. No. 13/837,801, Jun. 9, 2016, Office Action.
U.S. Appl. No. 14/017,039, Jul. 5, 2016, Issue Notification.
U.S. Appl. No. 14/023,428, Jun. 13, 2016, Office Action.
U.S. Appl. No. 14/246,926, Jun. 15, 2016, Office Action.
U.S. Appl. No. 14/246,973, Jul. 7, 2016, Office Action.
U.S. Appl. No. 14/312,339, May 3, 2016, Office Action.

\* cited by examiner

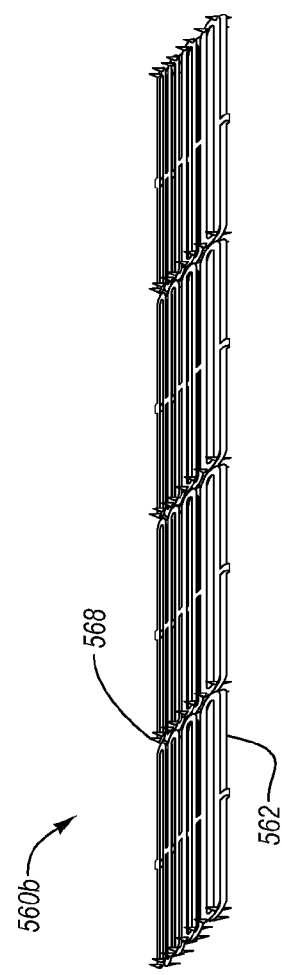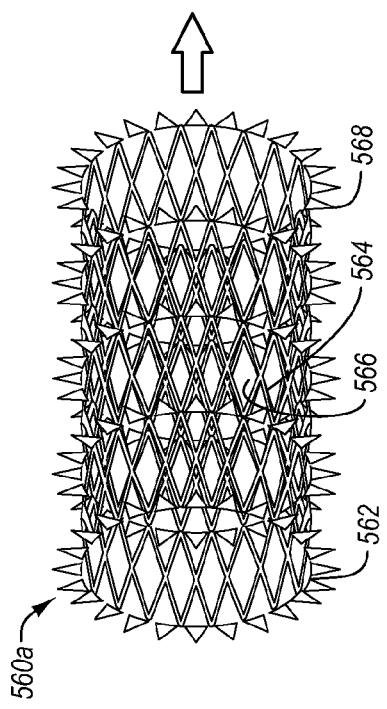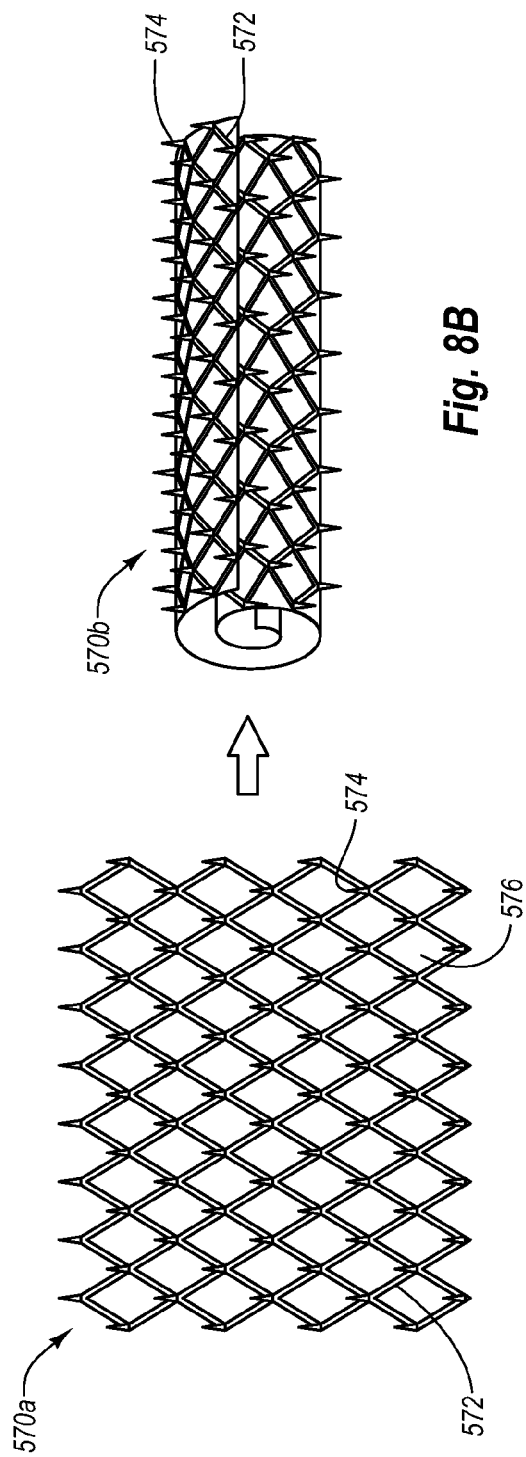

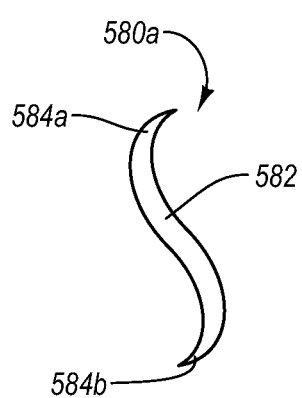
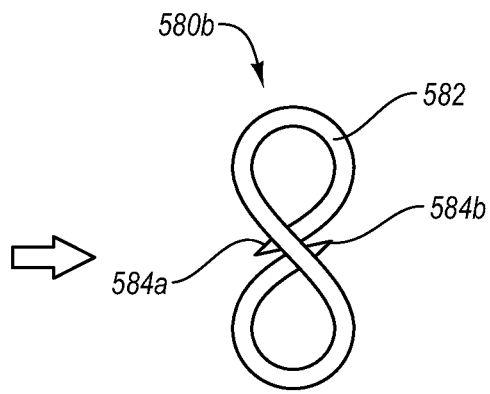
Fig. 9A                Fig. 9B
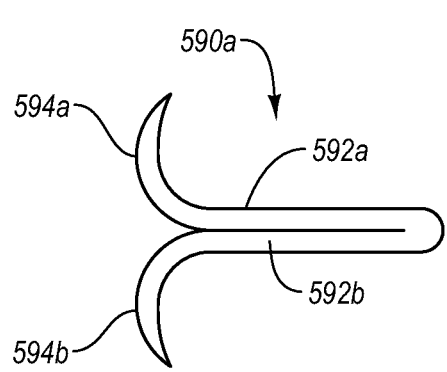
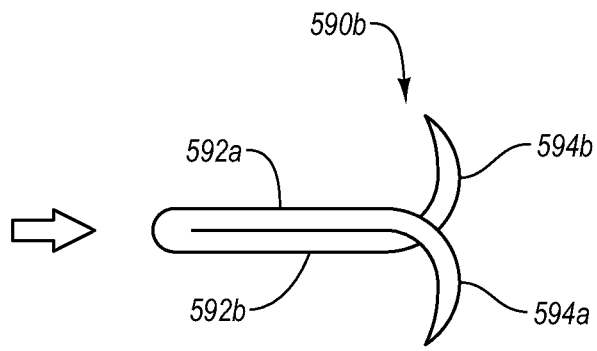
Fig. 10A               Fig. 10B

MEDICAL DEVICE FOR REPAIRING A FISTULA

CROSS-REFERENCE TO RELATED APPLICATIONS

This application is a divisional of U.S. patent application Ser. No. 12/548,274, filed Aug. 26, 2009.

BACKGROUND OF THE INVENTION

1. The Field of the Invention

The present invention relates to medical devices usable to repair a fistula. More particularly, the present invention relates to medical devices having distal flexibility and/or controllability to repair a fistula.

2. The Related Technology

In medicine, a fistula is an abnormal connection or passageway between two organs or vessels that normally do not connect. Usually, a fistula is an abnormal passageway between two such organs or vessels, where a first body lumen thereby is abnormally connected to a second body lumen (e.g., organ to organ, organ to vessel, and/or vessel to vessel). The fistula itself is often not well defined and can be represented as a tear, opening, or hole in the tissue so as to have two different openings.

Fistulas can be malformations within the body with serious health consequences, and may even lead to death. Often, the body fluid contained in one body organ or lumen can pass through the fistula to another body organ or lumen. Such passage of body fluids can contaminate or cross-contaminate the body lumens when the fluids should not be passed therebetween. Also, a fistula in a vessel can lead to unfavorable blood deposits in an adjacent lumen or organ.

Some fistulas can be caused by disease. For example, inflammatory bowel diseases, such as Crohn's disease and ulcerative colitis, are the leading causes of anorectal, enteroenteral, and enterocutaneous fistulas. A person with severe stage-3 hidradenitis suppurativa may also develop fistulas.

Some fistulas can be an unfortunate consequence of a medical procedure, where the fistula forms during the implementation of the medical procedure. For example, complications from gallbladder surgery can lead to a biliary fistula. Also, radiation therapy can lead to a vesicovaginal fistula. However, an intentional arteriovenous fistula can be deliberately created in some instances as part of a therapy.

Some fistulas can be caused by trauma. For example, head trauma can lead to perilymph fistulas, whereas trauma to other parts of the body can cause unwanted arteriovenous fistulas. Obstructed labor can lead to vesicovaginal and rectovaginal fistulas. An obstetric fistula develops when blood supply to the tissues of the vagina and the bladder and/or rectum is cut off during prolonged obstructed labor. At some point, the tissues can die and a hole forms in the tissue through which urine and/or feces pass uncontrollably. Vesicovaginal and rectovaginal fistulas may also be caused by trauma.

Fistulas need to be repaired because they are painful and can cause secondary ailments from certain body fluids or other substances passing into a conduit, lumen, or other body cavity or tissue in which the body fluid does not belong. This can include urine passing into the vaginal or colon conduits, food or drink passing into the lungs, and blood passing from a vessel into another type of body conduit, such as an airway. Currently, fistulas are difficult to fix and require invasive surgery where the fistula is manually stitched closed. Often, surgeries that fix fistulas actually require forming an incision in a patient larger than the actual fistula itself, which is problematic because the incision also has to heal and is susceptible to infection from the surrounding environment and from the fistula itself.

Surgery is often required to ensure adequate drainage of the fistula so that pus may escape without forming an abscess. Various surgical procedures are commonly used to close a fistula, and utilize a common suture to stitch the fistula closed. For example, a fistulotomy can include placement of a seton, which is a cord that is passed through the path of the fistula to keep it open for draining. Also, an endorectal flap procedure can be performed where healthy tissue is pulled over the internal side of the fistula to keep feces or other material from reinfecting the channel. Additionally, treatments can include filling the fistula with fibrin glue, or plugging it with plugs made of porcine small intestine submucosa or other biocompatible substance. Surgery for anorectal fistulae is not without side effects, including recurrence, reinfection, and incontinence. The limited space available during the surgical procedure complicates the ability to properly stitch the fistula closed.

BRIEF SUMMARY OF THE INVENTION

The present invention includes a medical device configured to apply a closure element to tissue surrounding a fistula for repairing the fistula. The fistula can be any type of fistula has an abnormal channel from one body part to another body part (e.g., organ to organ, organ to vessel, vessel to vessel, etc.). The medical device of the present invention can be configured to apply a closure element to tissue adjacent to a fistula to repair any type of fistula at any location within the body of a subject. Examples of fistulas that can be repaired with the present invention include anorectal fistulas, enteroenteral fistulas, enterocutaneous fistulas, vesicovaginal fistulas, arteriovenous fistulas, perilymph fistulas, rectovaginal fistulas, ureterocolon fistulas, and the like.

In one embodiment, the present invention can include a medical device for delivering a closure element to tissue within, proximal, defining, and/or adjacent to a fistula of a subject so as to close and repair the fistula. The medical device can include a closure element, a shaft, a carrier assembly, and controller systems. The closure element can have tissue-grabbing members, and can be configured for being deployed into tissue within and/or adjacent to a fistula so as to close and repair the fistula. The shaft can have a distal end, proximal end, and a sufficient length and flexibility at a selected portion to be inserted into a natural opening or incision that communicates with the fistula, and be controllably delivered to the fistula and placed in a manner such that the distal end of the medical device can be placed at or within the fistula. Such placement can allow for the closure element to be applied and repair the fistula.

The shaft can include a carrier assembly having a plurality of members cooperatively configured for retaining the closure element within the carrier assembly. The carrier assembly can be configured with a garage for retaining the closure element, and selectively controllable members for deploying the closure element from the carrier assembly. The carrier assembly can include a proximal end and a distal end, where the distal end can have sufficient flexibility so as to be capable of being pointed at or inserted into the fistula. A controller system can be configured as a delivery controller and can be operably coupled to the distal end of the shaft.

The delivery controller can be configured for controlling the delivery and placement of the distal end (e.g., garage) of the shaft at or within the fistula.

A controller system can be configured to be capable of selectively deploy the closure element by being operatively coupled to the carrier assembly and/or members of the carrier assembly that can facilitate deployment of the closure element. The deployment controller system can be configured for controlling a plurality of members in the carrier assembly so as to deploy the closure element from the garage and into the tissue within and/or adjacent to the fistula so as to repair the fistula.

In one embodiment, the medical device can further include a locator assembly and a corresponding controller system. The locator assembly can have a distal end and a proximal end, where the distal end can have a locator configured for locating the fistula. For example, the locator can include a selectively expandable locator members, such as locator wings, that are configured for expanding to a diameter sufficient for contacting the tissue within and/or adjacent to the fistula such that the location of the fistula can be identified. A controller can be configured to control the locator assembly so as to be capable of locating the fistula and/or tissue adjacent, within, or defining the fistula.

The medical device can be configured in accordance with at least one of the following characteristics: the outer diameter of the shaft and/or carrier assembly can from about 0.2 cm to about 1 cm, more preferably from about 0.3 cm to about 0.75, and most preferably from about 0.4 cm to about 0.6 cm, or larger than about 0.17 inches. However, the outer diameter could be smaller such as about 0.01 cm, 0.05, or 0.01 cm as well as larger to about 1.5 cm, 2 cm, or 4 cm, if feasible. The length of the shaft and/or carrier assembly can vary greatly depending on the access point in the body and the corresponding position of the fistula. For example, the length can be longer than about 5 cm, between about 10 cm to about 200 cm, more preferably about 20 cm to about 150 cm, and most preferably about 30 cm to about 100 cm.

The shaft can include a distal end portion as a selected portion having flexibility; controlling members for controlling the deflection or bending of the selected portion; the shaft can include components of an endoscope such that the medical device can function as an endoscope; the distal end portion can be flexed, bent, or deflected such that the tip is at an angle of at least about 45, about 90, about 120, or about 180 degrees with respect to the shaft; the closure element can be one of a star closure element, collapsible tubular closure element, self-rolling closure element, reverse closure element, clam closure element, or combinations thereof.

The locator can have a length of at least about 0.25 cm, between about 0.3 cm to about 3 cm, more preferably about 0.4 cm to about 2 cm, and most preferably about 0.5 cm to about 1 cm. The locator can include at least one, two, three, four or more locator wings, said locator wings can have an expanded diameter of at least about 0.25 cm, between about 0.3 cm to about 3 cm, more preferably about 0.4 cm to about 2 cm, and most preferably about 0.5 cm to about 1 cm. The locator assembly can be configured to collapse and withdraw from the fistula as the closure element is deployed. Alternatively, the locator assembly can be pulled back through the closure element once the closure element is deployed. The shape-memory of the closure element allows the locator assembly to be pulled through an aperture of the closure element so as to deform the closure element, and the closure element can then revert to a substantially planar orientation to closure the vessel.

In one embodiment, the present invention can include a method for delivering a closure element into tissue within and/or adjacent to a fistula of a subject so as to close and repair the fistula. The method can include the following: inserting a distal end of a medical device configured to repair a fistula into a natural opening or incision in the subject, the distal end having a garage retaining a closure element configured for being deployed into tissue within and/or adjacent to a fistula so as to repair the fistula; delivering the distal end and garage to the fistula; and deploying the closure element into tissue within and/or adjacent to a fistula so as to repair the fistula.

In one embodiment, the method can further include flexing, bending, or deflecting the distal end portion during the delivering such that the tip is at an angle of at least about 45, about 90, about 120, or about 180.

In one embodiment, the method can further include: inserting a locator into the fistula, the locator having selectively expandable locator wings configured for expanding to a diameter sufficient for contacting the tissue within and/or adjacent to the fistula such that the location of the fistula can be identified; expanding locator wings of the locator such that the locator wings contact the tissue within and/or adjacent to the fistula; and identifying the locator to be at or within the fistula to locate the fistula. Also, the method can further include the following: collapsing the locator wings; and withdrawing the locator from the fistula as the closure element is deployed.

These and other embodiments and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which:

FIGS. 7A-7B illustrate a collapsible tubular closure element.

FIGS. 8A-8B illustrate a self-rolling closure element.

FIGS. 9A-9B illustrate a reverse closure element.

FIGS. 10A-10B illustrate a clam closure element.

DETAILED DESCRIPTION OF THE PREFERRED EMBODIMENTS

Generally, the present invention includes a medical device for repairing a fistula. The fistula can be any type of fistula that provides an abnormal channel from one body part to another body part (e.g., organ to organ, organ to vessel, and/or vessel to vessel). The medical device of the present invention can be configured to repair any type of fistula at any location within the body of a subject. Examples of fistulas that can be repaired with the present invention include anorectal fistulas, enteroenteral fistulas, enterocutaneous fistulas, vesicovaginal fistulas, arteriovenous fistulas, perilymph fistulas, rectovaginal fistulas, ureterocolon fistulas, vesicointestinal, bronchoesophageal, cervical, colocutaneous, abdominal, biliary, blind, congenital, genitourinary, orofacial, uretocutaneous, uretovaginal, vessical, duodenal, and the like.

The present invention can include a medical device having an elongate shaft with a distal garage housing a closure element that is configured for being delivered into tissue surrounding a fistula in order to promote fistula repair. Additionally, the medical device can have sufficient distal flexibility and/or controllability so as to be capable of traversing through a natural opening that communicates with a body lumen to a fistula formed with another body lumen. The closure element can be applied to the tissue on the outer edge or internal surface or any other location related to the fistula in order to repair the fistula. The shaft and/or garage that retains the closure element during placement proximal to the fistula can have increased flexibility at the distal end in order to enhance the ability to traverse around bends or junctions in body lumens for placement adjacent to or within a fistula. The increased flexibility can also enhance the ability to point the tip (e.g., garage) toward or into the fistula when at an angle with respect to the orientation of the body lumen.

I. Fistula Repair

The medical device of the present invention can be configured to repair a fistula by applying a closure element to tissue adjacent to or within a fistula. There are various strategies that can be employed in order to repair a fistula, which includes various areas of tissue that are proximal or associated with the fistula in which the closure element can be applied. This can include applying a closure element to the tissue surrounding a fistula, to the tissue within a fistula canal, to the tissue both surrounding the fistula and the tissue within the fistula canal, to tissue on an opposite side of the fistula, to tissue on both sides of the fistula canal, to tissue adjacent to both openings of the fistula, and the like. Accordingly, the medical device of the present invention can be configured such that the closure element applier can deliver an embodiment of closure element to repair the fistula as described in connection to FIGS. 1A-1I.

Figure 1A:
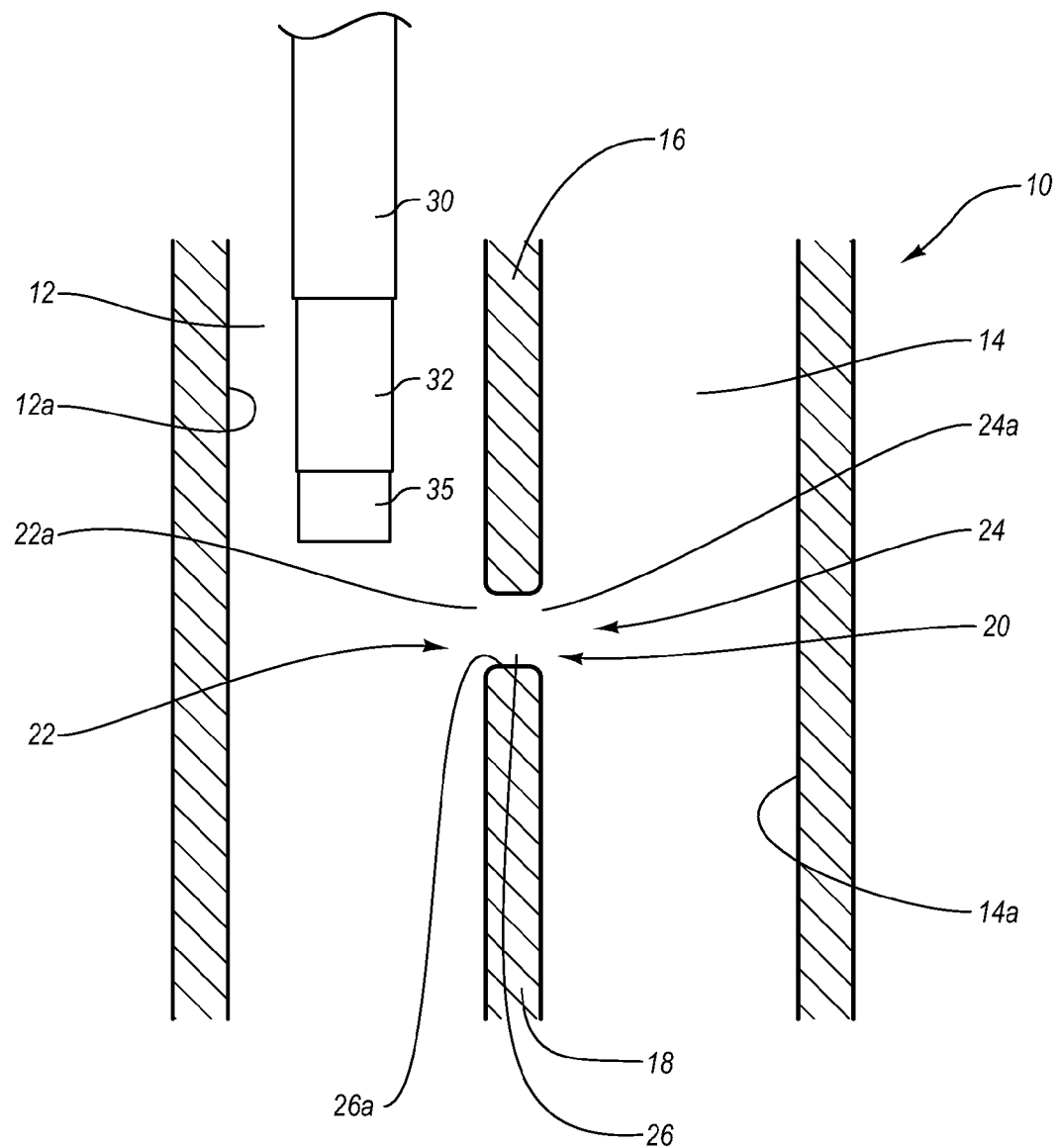
FIG. 1A is a schematic representation of a medical device being delivered through a lumen to a fistula.

FIG. 1A is a general schematic representation of a body portion 10 having a first body lumen 12 and a second body lumen 14 separated by a first tissue portion 16 and a second tissue portion 18 with a fistula 20 disposed therebetween. The fistula 20 has a first opening 22 defined by a first opening wall 22a (e.g., tissue) that communicates with the first body lumen 12 and a second opening 24 defined by a second opening wall 24a (e.g., tissue) that communicates with the second body lumen 14. A fistula conduit 26 defined by a fistula conduit wall 26a (e.g., abnormal tear surface) can extend between the first opening 22 and second opening 24 of the fistula 20. The body lumens 12, 14 can also be body cavities or organs, which are referred to herein generally as body lumens.

A medical device 30 having a flexible portion 32 and garage 35 retaining a closure element 34 (FIG. 1B) is shown to be disposed in the first body lumen 12 and the garage 35 is aligned along the longitudinal direction of the first body lumen. As shown, the flexible portion 32 is not bent or deflected toward the fistula 20.

Figure 1B:
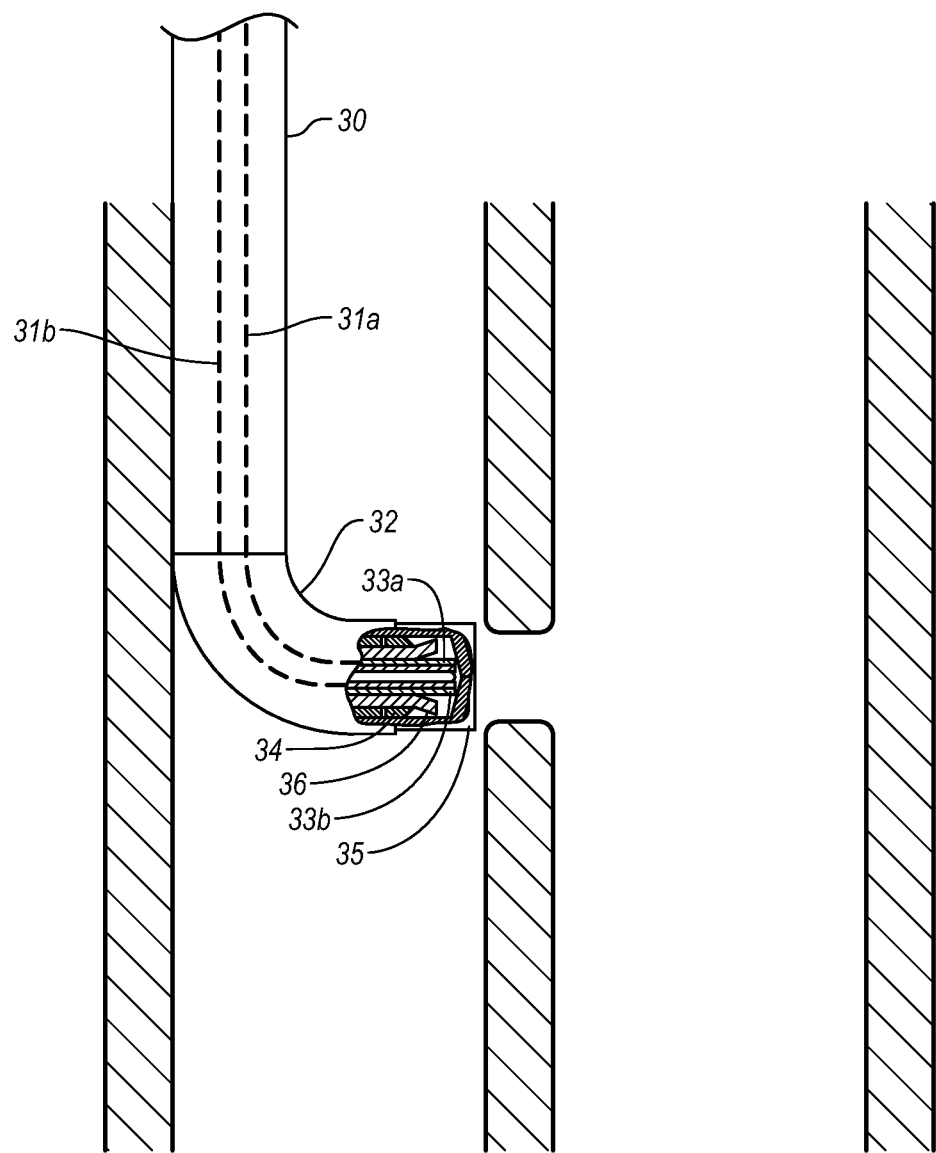
FIG. 1B is a schematic representation of a flexible portion of the medical device being bent so as to point toward the fistula.

FIGS. 1B-1I are schematic representations of the medical device 30 being inserted into the first body lumen 12, and positioned at the corresponding opening 22 of the fistula 20. As shown in FIG. 1B, the medical device 30 can be inserted into the first body lumen 12 via a natural body opening that naturally communicates with one of the body lumens. A natural body opening can be the mouth, nostril, urethra, vagina, anus, and the like. Also, the medical device 30 can be inserted through the fistula itself. As such, the medical device 30 can be inserted into and moved through the natural body opening until the flexible portion 32 and garage 35 passes through the body lumen 12 and reaches the fistula 20. Such positioning can be achieved with the distal end of the medical device 30 having a flexible portion 32. The flexible portion 32 is flexed by controlling bending elements 31a, 31b that are coupled to a contraction point 33a or an extension point 33b, or vice versa depending on orientation. For example, the bending element 31a is contracted so as to pull the contraction point 33a is a proximal direction, and the bending element 31b is extended so as to push the extension point 33b in a distal direction. The simultaneous movement of the bending elements 31a, 31b can selectively bend the flexible portion 32 to point the garage in a desired direction, such as toward the fistula 20. The garage 35 of the medical device 30 can then be positioned adjacent to the fistula 20 such that the closure element 34 can be applied to the tissue of the repair location 28 adjacent to or defining the fistula 20 in order to repair the fistula 20.

Delivery of the medical device 30 through a natural body lumen or organ to the site of the fistula 20 can be advantageous in that many of the body lumens 12, 14 susceptible to developing a fistula 20 have a diameter of sufficient size to allow for a medical device 30, such as a catheter or endoscope, to be passed therethrough. This also allows for the medical device 30 to have a size that is large enough to provide a garage 35 for maintaining deployment components (e.g., bending elements 31a, 31b, contraction point 33a, extension point 33b, etc.) that are configured to be manipulated and controlled by a user so as to control the deployment of the garage 35 of the medical device 30 to the fistula 20. The deployment components can be any component that operates so as to allow the flexible portion 32 of the medical device so be flexed or bent so as to be passed around tight bends, into select lumen, or bend to be at any angle relative to the longitudinal direction of the lumen.

For example, the deployment components can be manipulated so that the position and orientation of the garage 35 can be passed into a fistula 20 having a substantially longitudinal axis that is at an angle (e.g., alpha) with respect to the longitudinal axis of the body lumen. This can include manipulating the flexible portion 32 of the medical device 30 to be at an angle (e.g., alpha) of about 45 degrees, 90 degrees, 135 degrees, 180 degrees, and any angle therebetween. For example, the route of deployment may result in the tip of the medical device 30 needing to be turned in 180 degrees in order to enter an opening of the fistula 20, and the deployment components can cause the tip to be turned at 180 degrees for deployment of the closure element 34.

In one embodiment, the flexible portion 32 can be sufficient flexibility so as to be capable of being bent at an angle of about 45 degrees, about 90 degrees, about 135 degrees, about 180 degrees, and any angle therebetween. This can be achieved by utilizing materials for the various components that are included in the garage 35 and for the garage 35 itself. Many medical-grade polymers can be configured to be elastic enough for such flexibility. The flexible portion 32 or entire distal end of the medical device 30 including the garage 35 can be configured to have sufficient flexibility to bend as described herein. Optionally, the medical device 30 and the components thereof can have shape memory so as to automatically return to the original orientation, such as substantially straight or curved. However, the flexible portion 32 can also be configured to be malleable so as to retain the orientation once obtained. Such malleability can be used to bend the distal end of the medical device 30 in one direction and retain that direction until the distal end is bent in a different direction. The bending can be achieved by pushing one of the bending elements 31a or 31b and pulling the other so that the contraction point 33a contracts one side of the medical device 30 and the extension point 33b extends the other side of the medical device, which functionally bends the medical device in a desired direction.

Figure 1C:
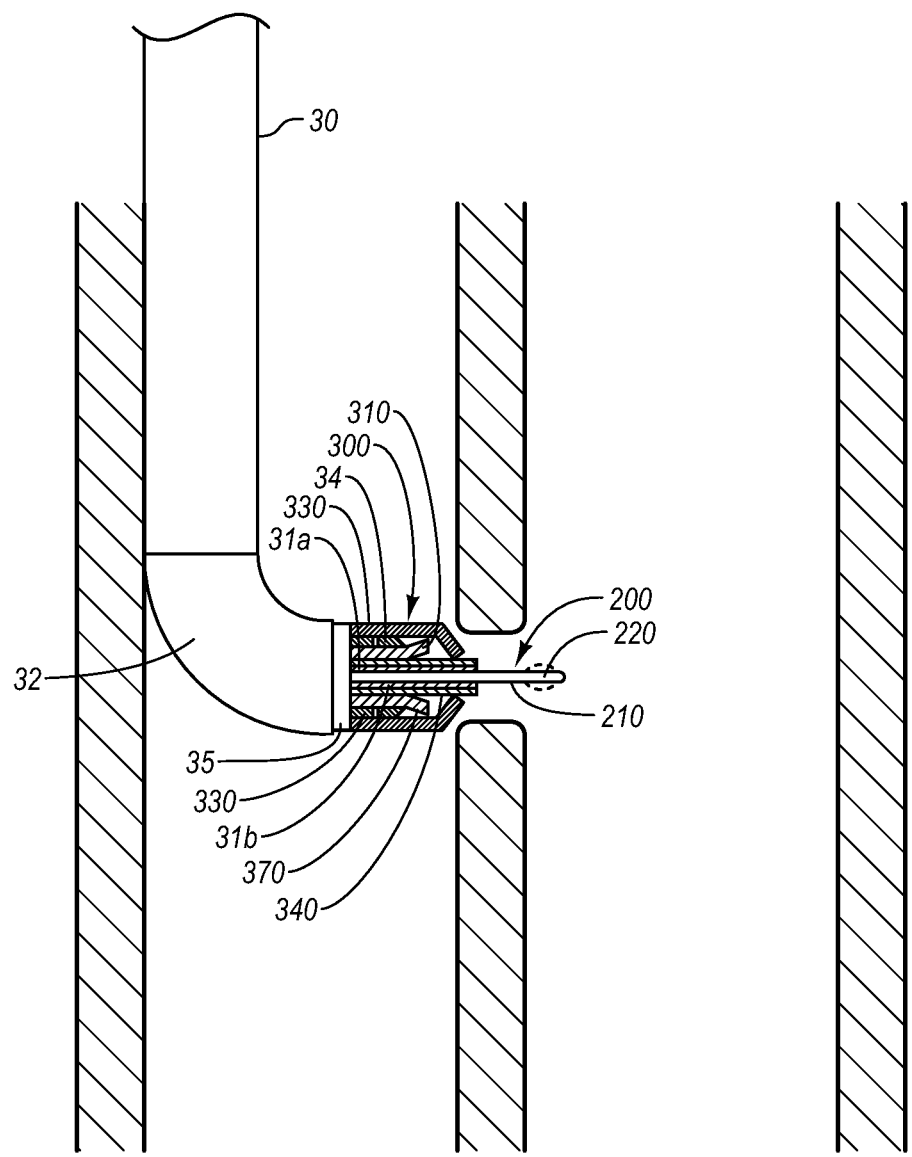
FIG. 1C is a schematic representation of a locator being extended from the medical device into the fistula.

FIG. 1C shows the medical device 30 after the flexible portion 32 has been bent so as to point the garage 35 toward the fistula 20. After the garage 35 is placed proximal to the fistula 20, a locator assembly 200 can be utilized to locate the fistula 20. The locator assembly 200 can include a locator 220 at the distal end 210. The locator 220 may be retained within the garage 35 during placement proximal to the fistula 20. As shown, the garage 35 can also include features of a carrier assembly 300, which can include a support member 340, a carrier member 310, a pusher member 320, and a cover member 330. The carrier member 310 can include the closure element 34 in a space 370 associated with the carrier member 310, pusher member 320, and cover member 330. The locator 220 can be extended into the fistula 20 by being distally pushed so that the distal end 210 is within the fistula 20.

Figure 1D:
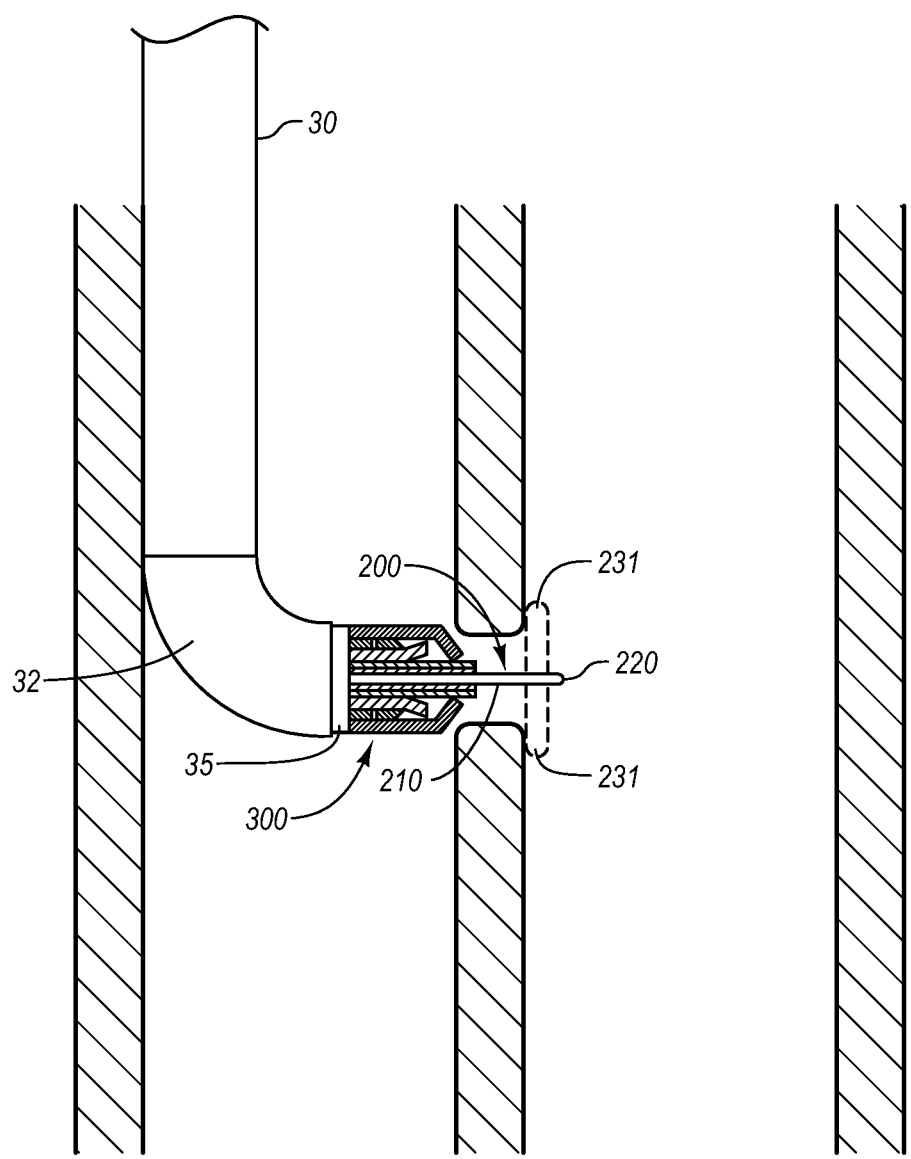
FIG. 1D is a schematic representation of locator wings of the locator being expanded so as to contact and locate the fistula.

After being placed within, adjacent or proximal to the fistula 20, the locator 220 can be expanded by radial or laterally expanding locator wings 231 as shown in FIG. 1D. The locator wings 321 can be expanded to a sufficient length for contacting tissue of the fistula 20, which can include the tissue of the body lumen 14. The contact of the locator wings 321 with the fistula 20 can be used to identify when the fistula 20 is located. Also, proximally pulling the locator 220 against the fistula 20 can also be useful. Additionally, radiopaque materials on the locator 220 and/or locator wings 231 can be helpful in locating the fistula 20.

Additionally, FIG. 1D shows the carrier assembly 300 being extended from the garage 35. However, the functionality of the medical device 30 can be retained when only selected components, such as components of the locator assembly 200 and carrier assembly 300, are extended from the garage 35.

Figure 1E:
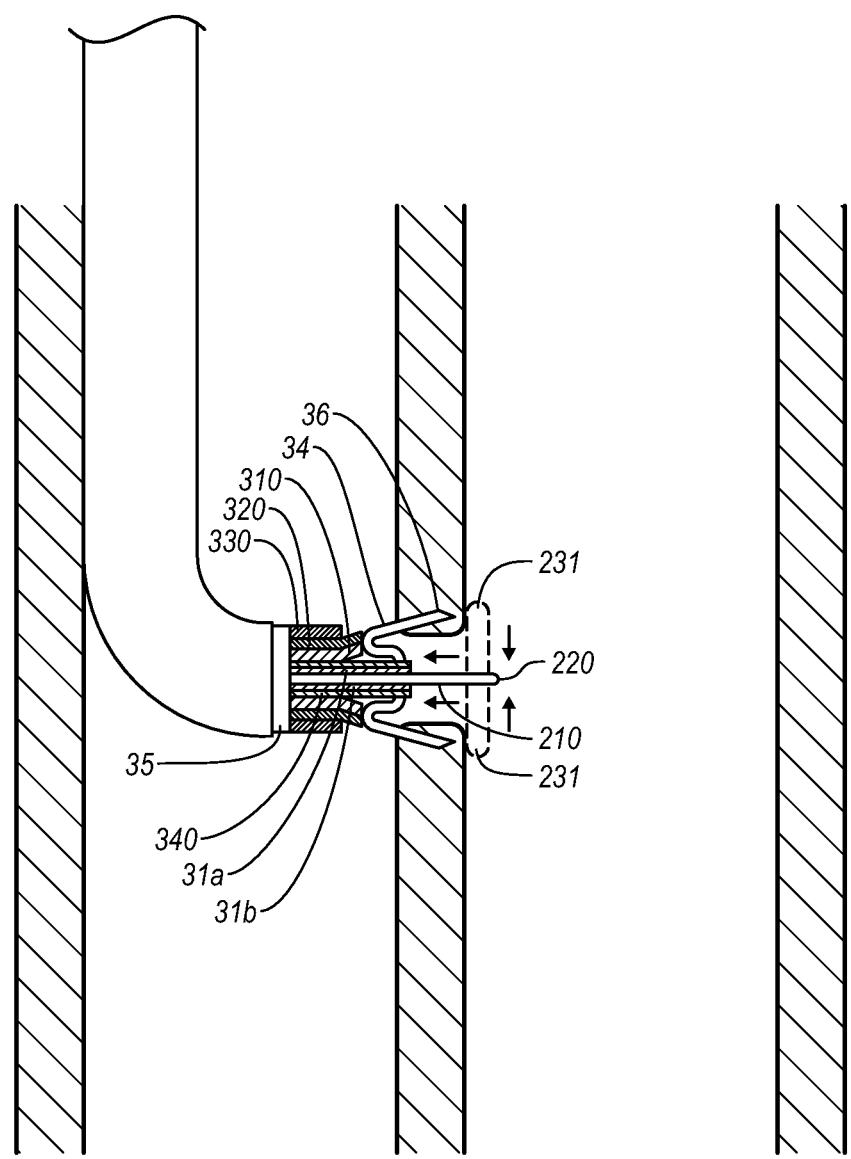
FIG. 1E is a schematic representation of a closure element being applied to tissue adjacent and/or within the fistula.

FIG. 1E shows the operation of the carrier assembly 300 in deploying the closure element 34 to repair the fistula 20. As shown in cross-sectional view, the pusher member 320 has pushed the closure element 34 over the carrier member 310 and out of the cover member 330 so as to penetrate the tissue of the fistula 20. The carrier member 310 is shown to have a radially expanding cross-section at the distal end, which allows for the closure element 34 to be radially expanded during deployment into the tissue. Such radial expansion of the closure element 34 allows for the tines 36 (e.g., tissue grabbing members) to enter the tissue of the fistula 20 at an angle that allows for more tissue to be grabbed.

During the deployment of the closure element 34 into the tissue of the fistula 20, the locator wings 231 can be retracted as shown by the arrows. The retraction of the locator wings 231 allows for the locator 220 to be withdrawn from the fistula 20 as the closure element 34 is repairing the fistula 20. Accordingly, many different functional actions can be occurring simultaneously or substantially simultaneously during the process of repairing the fistula 20 and/or after deployment of the closure element 34.

Figure 1F:
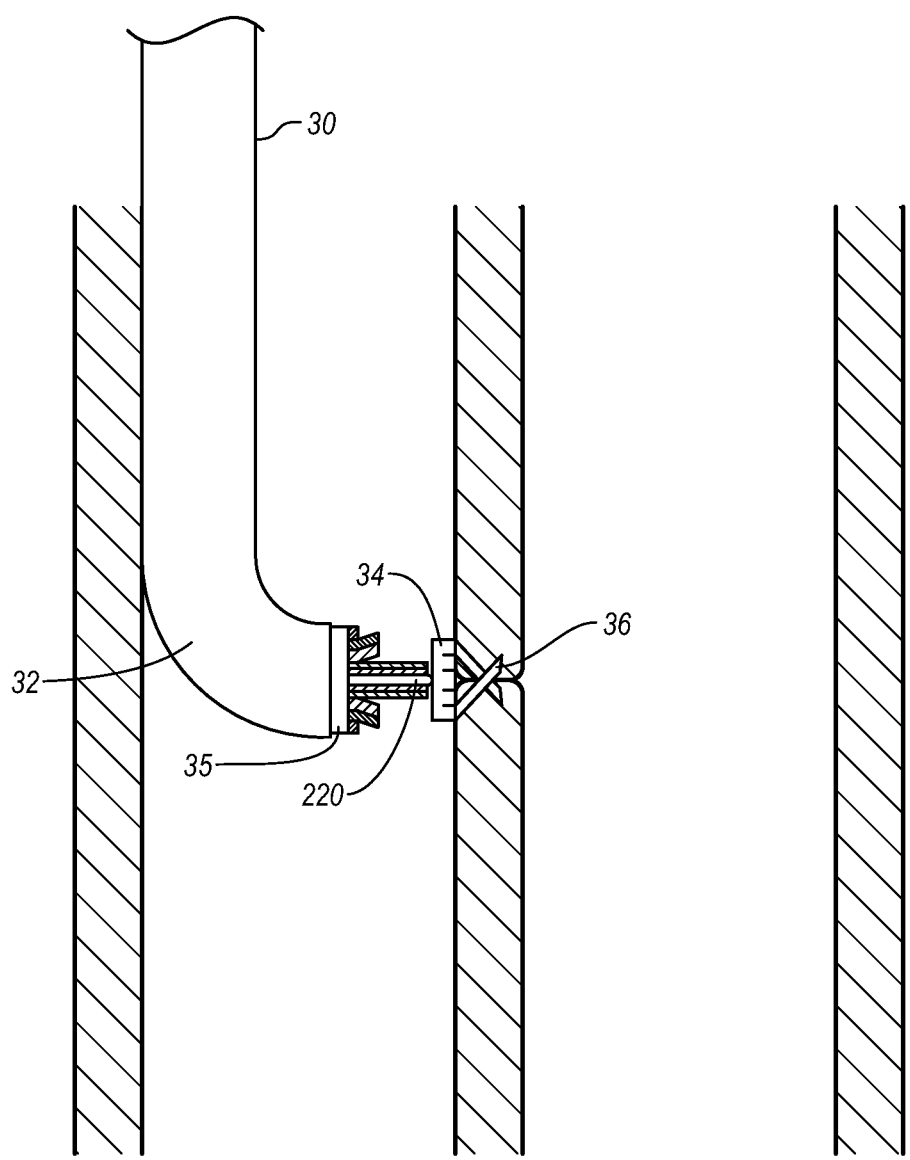
FIG. 1F is a schematic representation of the closure element closing with tissue-grabbing members pulling the tissue together to repair the fistula.

FIG. 1F shows the closure element 34 retracting to a closed orientation that repairs the fistula 20. The closed orientation of the closure element 34 can be achieved by the tines 36 being drawn, radially together. This allows the tines 36 to pull tissue together to repair the fistula 20.

Also, FIG. 1F shows the locator 220 being fully retracted from the fistula 20. It can be beneficial to retract the locator 220 from the fistula 20 during deployment of the closure element 34 so that the locator 220 or its components are not stuck or otherwise trapped within the repaired fistula 20. Accordingly, the timing of closure element 34 deployment and locator retraction can be correlated to achieve maximum benefit of having sufficient fistula location identification during the deployment of the closure element, but to also have selected retraction of the locator 220 to avoid any complications that may arise if the locator 220 was trapped by the closure element 34.

Figure 1G:
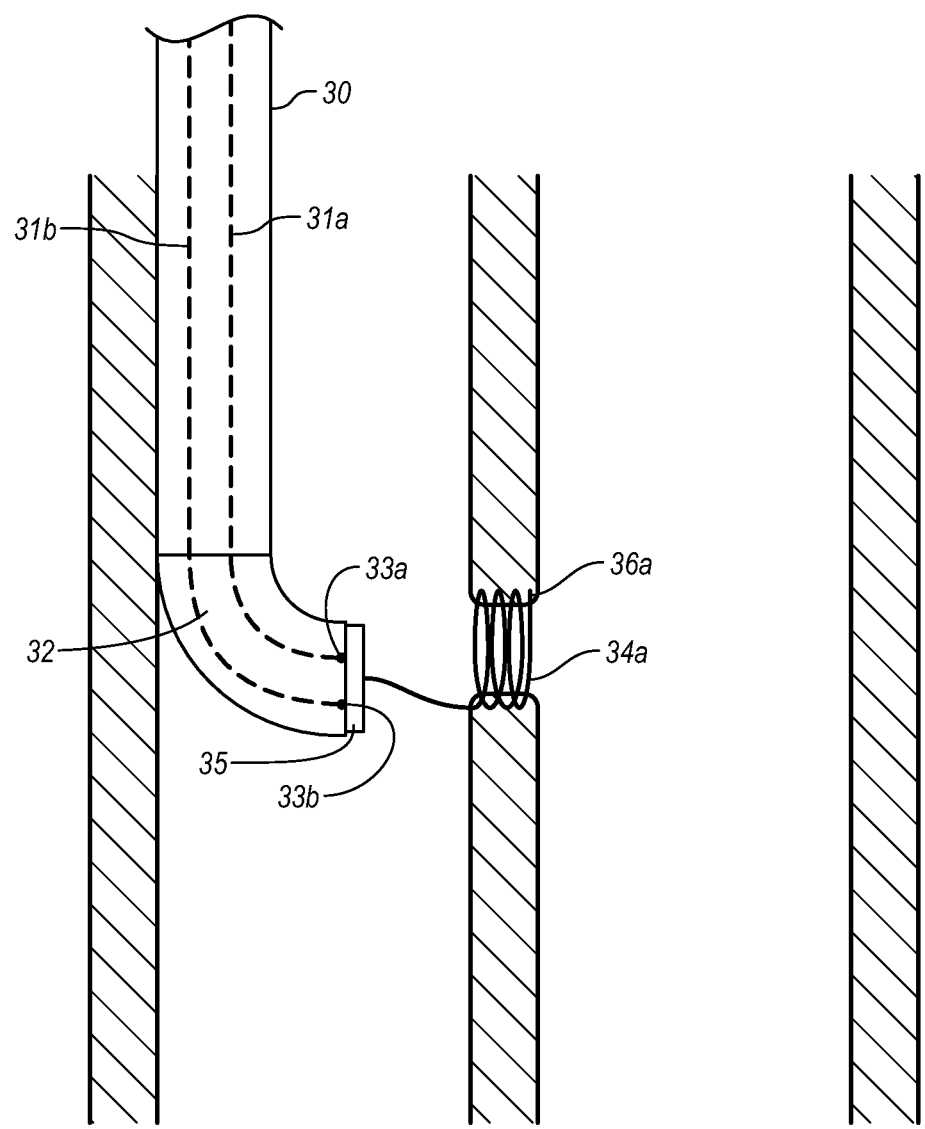
FIG. 1G is a schematic representation of another embodiment of a closure element repairing a fistula.

FIG. 1G is a schematic representation of an embodiment of a procedure to repair a fistula 20 with a medical device 30 that deploys a helical closure element 34. As described in FIG. 1B, the distal end of the medical device 30 is positioned at the opening 22 of the lumen 12 and the flexible portion 32 is bent so as to be directed toward the fistula 20. The flexible portion 32 is flexed by controlling bending elements 31a, 31b that are coupled to a contraction point 33a or an extension point 33b. For example, the bending element 31a is contracted so as to pull the contraction point 33a in a proximal direction, and the flexing element 31b is extended so as to push the extension point 33b in a distal direction. The simultaneous movement of the bending elements 31a, 31b can selectively bend the flexible portion 32. The helical closure element 34a is deployed from the garage 35 toward the fistula 20 with the helical turn being of a diameter larger than or about the size of the conduit 26 so that the tine 36a is capable of spiraling through the tissue of the conduit wall 26a until reaching a select point, such as the opposite opening 24. The helical closure element 34 can then be pulled taut so as to close the conduit 26. Alternatively, the winding of the helical closure element 34 can pull the tissue of the fistula 20 together.

Figure 1H:
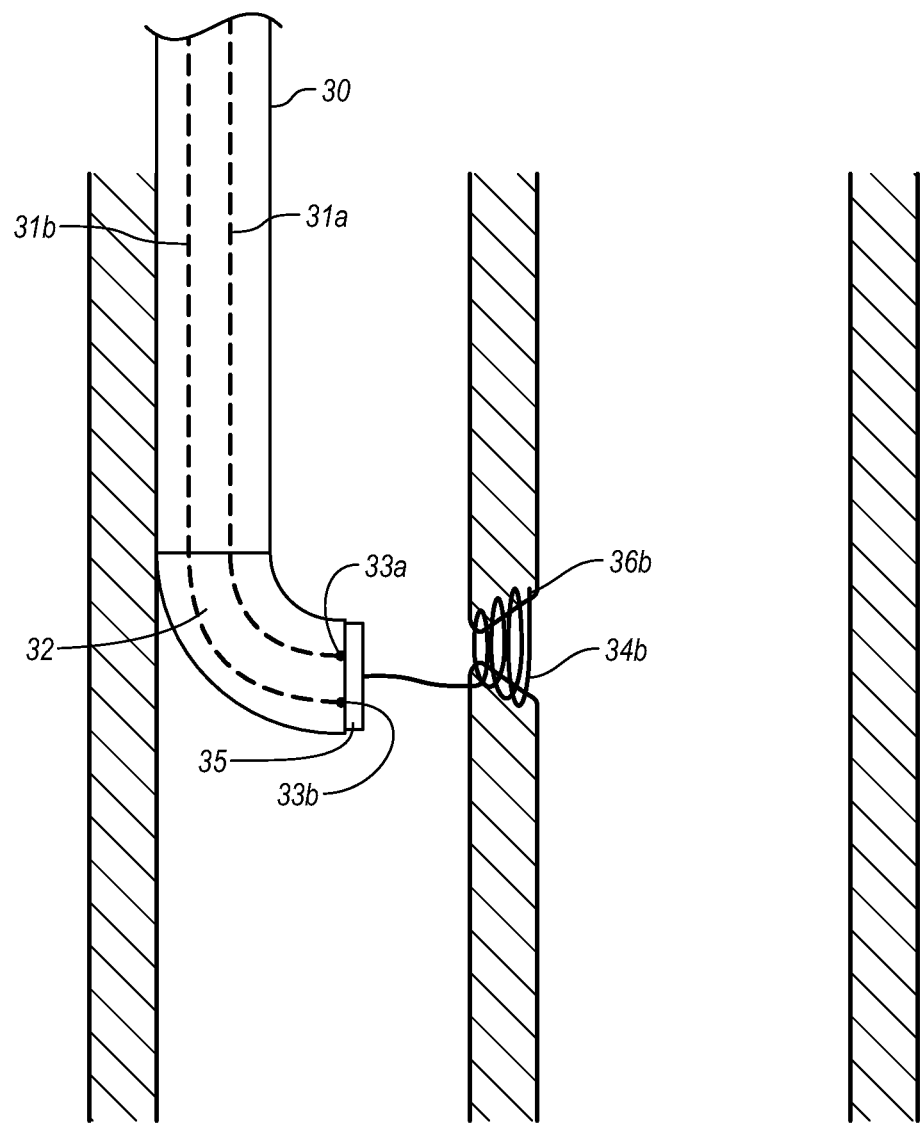
FIG. 1H is a schematic representation of another embodiment of a closure element repairing a fistula.

FIG. 1H is a schematic representation of an embodiment of a procedure to repair a fistula 20 with a medical device 30 that deploys a conical, helical closure element 34d. The conical, helical closure element 34 has a shape similar to that of a tornado so as to have a larger diameter distal end adjacent to the tine 36 compared to the diameter adjacent to the garage 35. The flexible portion 32 is flexed by controlling bending elements 31a, 31b that are coupled to a contraction point 33a or an extension point 33b. For example, the bending element 31a is contracted so as to pull the contraction point 33a is a proximal direction, and the bending element 31b is extended so as to push the extension point 33b in a distal direction. The simultaneous movement of the bending elements 31a, 31b can selectively bend the flexible portion 32 so as to point into the fistula 20. The conical, helical closure element 34b is deployed from the garage 35 toward the tissue of the fistula 20 with the distal helical turn being of a diameter at least or larger than the conduit 26 so that the tine 36b is capable of spiraling through the tissue of the conduit wall 26a until reaching a select point, such as the opposite opening 24. As the conical, helical closure element 34b is deployed, the conical shape pulls the conduit 26 closed from the first opening 22 to the second opening 24. This preferentially closes one opening (e.g., 22) compared to the opposite opening (e.g., 24).

The medical device 30 can deploy the closure element 34 (shown retained within the medical device) at a suitable repair location at the first opening 22, second opening, 24, or any location within the fistula conduit 26. Depending on the location of the fistula 20 and the organs and/or vessels affected by the fistula 20 it may be advantageous in some circumstances to close the fistula 20 at one of the openings 22, 24. However, a closure element that can be deployed within the fistula conduit 26 can be advantageous in other circumstances.

Figure 1I:
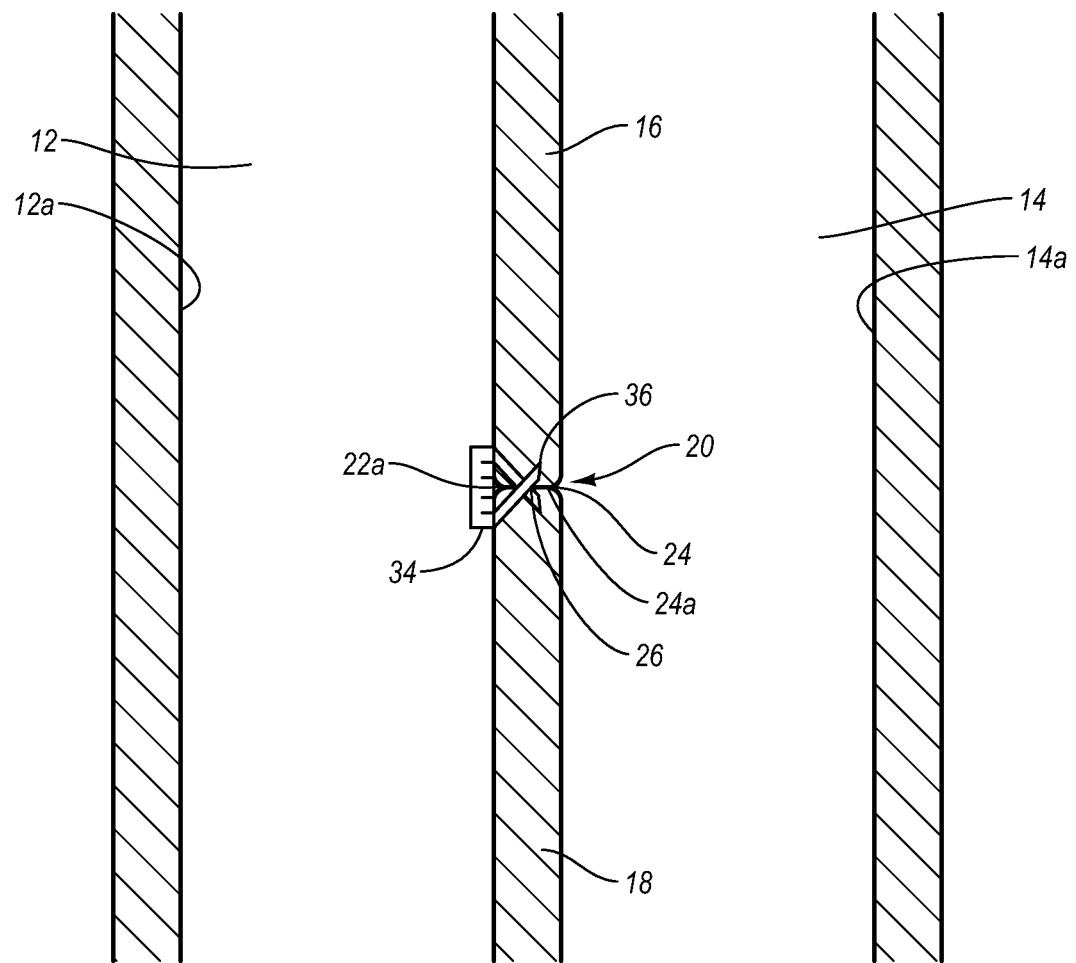
FIG. 1I is a schematic representation of a repaired fistula.

FIG. 1I is an illustration of an embodiment of a closure element 34 closing a fistula 20. As shown, the fistula of FIG. 1A has been closed by applying a closure element as in FIG. 1B to the first opening wall 22a of the first opening 22. By the first opening 22 being sealed, the fistula conduit 26 can drawn closed. The second opening 24 can thereby also be closed.

In on embodiment, the medical device can be delivered by a methodology that utilizes a catheter to deliver the medical device. In such a configuration, the garage of the medical device can be directed through the lumen of a catheter. This can include the medical device being traversed through an internal lumen of the catheter so that the distal end and garage can be passed therethrough and be directed toward the fistula. The catheter can be delivered to the fistula in any manner of catheter delivery, such as being passed over a guidewire (not shown). Thus, the flexibility of the medical device is sufficient to be passed through a catheter to the fistula.

Optionally, the medical device, including the garage and other portions of the medical device, can be substantially devoid of deployment components, such as the bending members and the like. As such, the flexibility is suitable for traversing the body lumen to the site of the fistula by being passed through a catheter lumen.

In on embodiment, the medical device can be configured to include components of an endoscope so that the medical device can be delivered to the fistula in a manner that endoscopes are delivered to sites within a body. In such a configuration, the endoscope can be delivered to the fistula, and the garage of the medical device can be directed through the lumen of the endoscope to the fistula. This can include the medical device being traversed through an internal lumen of the endoscope so that the distal end and garage can be passed therethrough. The endoscope can be delivered to the fistula an any manner of endoscope delivery, such as utilizing an endoscope light and camera for maneuvering the endospcope through body lumen to the fistula. The endoscope can also include standard endoscope components that enable the endoscope to traverse a body lumen so as to be deployed at a fistula. As such, the flexibility of the medical device is sufficient to be passed through an endoscope to the fistula. The medical device, including the garage and other portions of the medical device, can be substantially devoid of deployment components (e.g., bending members) such that the endoscope provides a route, and the medical device is flexible enough to traverse the route. Optionally, the medical device is integrated with an endoscope such that the garage having the closure element is delivered to the fistula while the endoscope is being delivered to the fistula.

In one embodiment, the medical device can be inserted into one of the body lumens or into the fistula conduit via an incision made through the skin and tissue proximate to the fistula. Accordingly, an incision can be made in the skin (not shown) and tissue adjacent to the fistula. This can allow for percutaneous delivery of the garage of the medical device to the fistula. Medical devices commonly configured to be traversed through an incision for percutaneous delivery, such as catheters, can be configured without the flexibility and/or maneuverability of other medical devices as described herein because the incision can provide a substantially straight conduit for passing the medical device to the repair site of the fistula without having to traverse any tight bends or other similar features. Also, it may be desirable for the incision to be substantially smaller than a normal opening so as to impart less trauma to the subject. As such, the medical device can have dimensions similar to catheters that are deployed percutaneously.

II. Closure Element Applier

The closure element applier can be configured to receive and retain the closure element (i.e., fistula closure element) such that the closure element is disposed substantially within the closure element applier. The closure element applier is configured to engage the tissue within and/or adjacent to one of the openings of the fistula, and to position and deliver the closure element into tissue to draw the tissue together in order to repair the fistula. When properly positioned, the closure element applier can be activated to distally deploy the closure element. During deployment of the closure element, the closure element applier can be configured to substantially uniformly or asymmetrically expand the closure element beyond a natural cross-section of the closure element such that the tines, barbs, or the like engage a significant amount of the tissue for repairing the fistula. After engaging the tissue, the closure element can then return to substantially the natural cross-section area and shape of the memory material. Thereby, the engaged tissue is drawn substantially closed and/or sealed, such that the fistula is repaired.

Figure 2A:
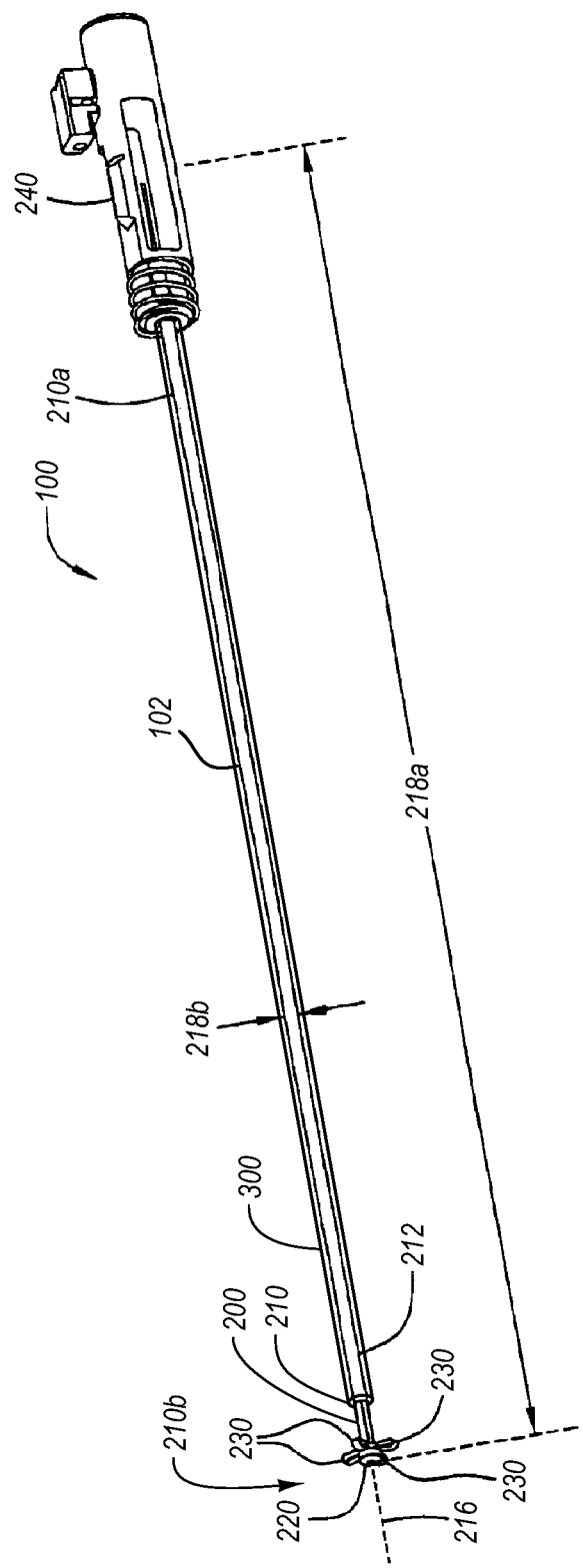
FIG. 2A illustrates an embodiment of a medical device having a locator assembly.

FIGS. 2A-2D illustrate a closure element applier apparatus 100 in accordance with the present invention. The apparatus 100 can be configured to receive and retain a closure element (not shown; discussed below) such that the closure element is disposed substantially within the shaft 102 of the closure element applier apparatus 100. The apparatus 100 can be provided as one or more integrated components and/or discrete components. As shown in FIG. 2A, the apparatus 100 can include a locator (or obturator) assembly 200 and a carrier assembly 300. For purposes of illustration, the locator assembly 200 and the carrier assembly 300 are shown in FIG. 2A as including substantially separate assemblies. As desired, however, the locator assembly 200 and the carrier assembly 300 each can be provided, in whole or in part, as one or more integrated assemblies. Information related to closure element appliers, locator assemblies, carrier assemblies, components thereof, mechanics thereof, and operation thereof can be obtained from U.S. Pat. No. 6,197,042 and co-pending applications and Ser. Nos. 09/610,128, 09/732,835, 09/866,551, 10/006, 400, 10/081,723, 10/356,214, 10/638,115, 11/048,503, 11/396,731, 11/744,089, 12/113,092, 60/946,042, and 60/946,030, the disclosures of which are expressly incorporated herein by reference.

Being configured to extend into a fistula opening, the locator assembly 200 can selectably contact tissue within the fistula canal or adjacent to the fistula. Whereby, the locator assembly 200 can be configured to draw the closure element applier 100 taut and maintain the proper position of the closure element applier 100 in relation to the fistula. The locator assembly 200 can include a flexible tubular body 210, wherein the flexibility allows for delivery through a body lumen and placement at the fistula. As illustrated in FIG. 2A, the locator tubular body 210 has a proximal end region 210a and a distal end region 210b and includes a predetermined length 218a and a predetermined outer cross-section 218b, both of which can be of any suitable dimension. The distal end region 210b of the locator assembly 200 can include a substantially rounded, soft, and/or flexible distal end or tip 220 (e.g., locator) to facilitate atraumatic advancement and/or retraction of the flexible distal end region 210b through the body lumen and to the fistula. As desired, the locator 220 can be more flexible to allow for being placed at or within the fistula, and can include deployment components (not shown) that bend and flex distal end region 210 so as to point the locator 220 toward the fistula.

Figure 2B:
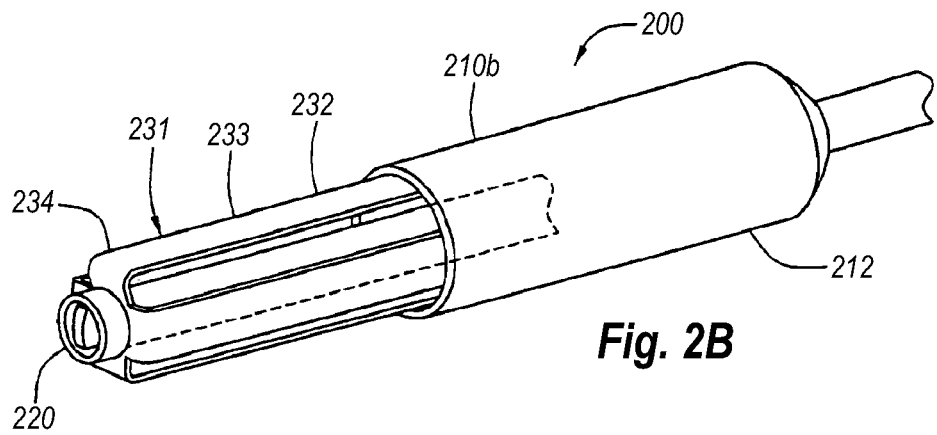
FIG. 2B illustrates the locator assembly of FIG. 2A having locator wings in an unexpanded state.
Figure 2C:
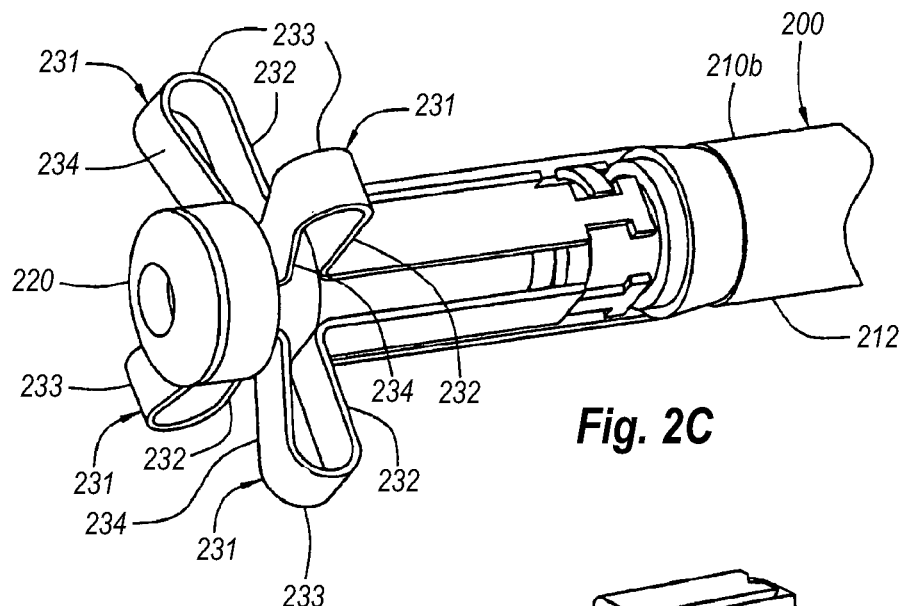
FIG. 2C illustrates the locator assembly of FIG. 2B having locator wings in an expanded state.

The locator 220 of the locator assembly 200 further can be selectably controllable between an unexpanded state (FIG. 2B) and an expanded state (FIGS. 2A and 2C). In the unexpanded state, the locator 220 has an unexpanded size; whereas, the locator 220 in the expanded state has an expanded size, which is greater than the unexpanded size. The locator 220 can be configured to expand from the unexpanded size to the expanded size and/or to contract from the expanded size to the unexpanded size, and the expansion and contraction of the locator can be substantially uniform about a longitudinal axis of the locator assembly 200. For example, one or more expansion elements 230 (i.e., locator wings 230) can be provided on the locator 220, and can be configured to expand substantially transversely with respect to a longitudinal axis 216 of the locator assembly 200. The expansion elements 230 can be substantially equally distributed about an outer periphery 212 of the locator 220. Optionally, the expansion elements 230 may include radiopaque markers (not shown) or may be wholly or partially formed from a radiopaque material to facilitate observation of the expansion elements 230 and/or the locator 220 using fluoroscopy or other imaging systems.

At least one of the expansion elements 230 can include a substantially flexible member 231 with a substantially fixed end region 232, an intermediate region 233, and a movable end region 234 as shown in FIGS. 2B-2C. For each substantially flexible member 231, the fixed end region 232 can be fixedly coupled with the locator 220; whereas, the movable end region 234 can be movably coupled with the locator 220, and configured to be axially movable relative to the fixed end region 232. When each movable end region 234 can be axially moved toward the relevant fixed end region 232, the intermediate regions 233 buckle and/or expand transversely outwardly, thereby transitioning the locator 220 of the locator assembly 200 from the unexpanded state to the expanded state. In contrast, the locator 220 transitions from the expanded state to the unexpanded state as each of the movable end regions 234 are axially moved away from the relevant fixed end region 232. Although the expansion elements 230 are shown as including the flexible members 231 in FIGS. 2B-2C for purposes of illustration, it is understood that the expansion elements 230 can include any type of expansion elements and are not limited to the illustrated embodiments. It is further contemplated that the expansion elements 230 may further include geometric features that allow/enhance the ability of the expansion elements to bend or fold from a retracted position to an expanded position. The expansion elements 230 may be constructed of a material such as steel, spring steel, plastics or composites. In one embodiment, the expansion elements are constructed of nitinol.

Figure 2D:
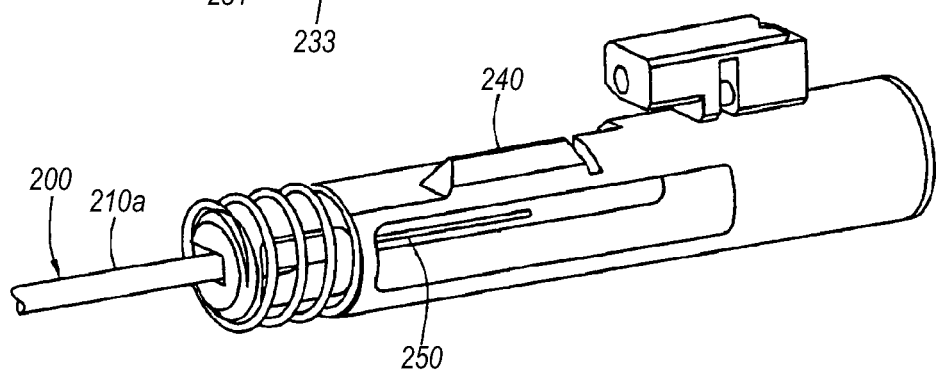
FIG. 2D illustrates a proximal end region of the locator assembly of FIG. 2A that has controllers.

Referring now to FIG. 2D, the locator assembly 200 may further include a locator control system 240 associated with the locator assembly. As shown in FIG. 2D, the locator control system 240 can be associated with the proximal end region 210a of the locator assembly 200 and can be configured to selectively control the distal end region 210b (e.g., flexibility, straightness, bends, positioning, and the like) and locator 220 of the locator assembly 200 between the unexpanded and expanded states. The locator control system 240 can selectively control the distal end region 210b to be longitudinally oriented or bent away to an angle up to 45, 90, 120 and/or 90 degrees. The locator control system 240 can also control the locator 220 and the locator wings 230 between the unexpanded and expanded states, such as by being activated by a switching system (not shown). For example, at least one control member 250, such as a rod, wire, or other elongate member, can be moveably disposed within a lumen (not shown) formed by the tubular body 210 and extending substantially between the proximal end region 210a and the distal end region 210b. The control member 250 has a proximal end region 250a that is coupled with the locator control system 240, which can be via a control block 260 (shown in FIG. 4D), and a distal end region (not shown) that is coupled with the distal end region 210b and locator 220 of the locator assembly 200, the expansion elements 230, and/or the movable end regions 234 of the substantially flexible members 231.

Additionally, the locator control system 240 can selectively transition the distal end region 210b from being straight to being bent, curved, or the like, and change the expansion elements 230 and/or the substantially flexible members 231 between the unexpanded and expanded states by moving the control member 250 axially relative to the tubular body 210. However, the control member 250 can be configured such that any articulation by other mechanical components can control the bending of the distal end region 210b as well as the expansion and contraction of the locator wings 230.

The locator control system 240 further includes a locator release system 490 (FIG. 4D) for maintaining the unexpanded state and/or the expanded state of the locator 220, the expansion elements 230, and/or the substantially flexible members 231. The locator release system 490 can be configured to maintain the expanded state of the locator 220, and can include any type of locking system and can be engaged, for instance, by activating a switching system or other means of activation. For example, once the substantially flexible members 231 have entered the expanded state, the locator release system 490 can secure the control member 250 to prevent axial movement relative to the tubular body 210, thereby maintaining the substantially flexible members 231 in the expanded state.

In the manner described in more detail below, the locator control system 240 also can be configured to disengage the locator release system 490, such that the locator 220, the expansion elements 230, and/or the substantially flexible members 231 can transition between the expanded and unexpanded states. The locator release system 490 can be disengaged, for example, by activating a mechanism (e.g., an emergency release system) (not shown). As desired, the locator control system 240 may further include a biasing system (not shown), such as one or more springs or other resilient members, to bias the locator 220, the expansion elements 230, and/or the substantially flexible members 231 to enter and/or maintain the unexpanded state when the locator release system 490 is disengaged.

Figure 3A:
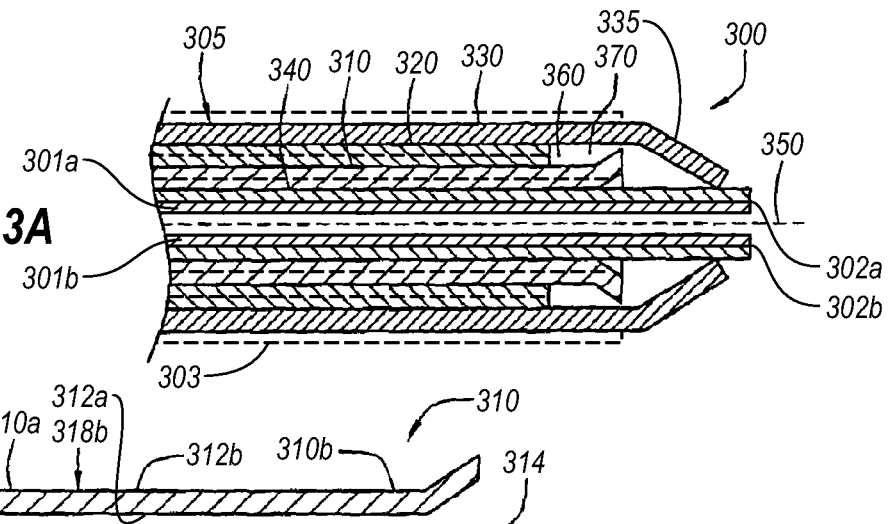
FIG. 3A illustrates an embodiment of a carrier assembly for carrying a closure element in a medical device.

Returning to FIG. 2A, the carrier assembly 300 can be coupled with, and slidable relative to, the locator assembly 200. The carrier assembly 300 is configured to receive and retain the closure element (not shown), which can be disposed substantially within the carrier assembly 300. Turning now to FIGS. 3A-3D, the carrier assembly 300 can include a tube set 305, including a carrier member 310, a pusher member 320, a support member 340, and a cover member 330. The carrier member 310, the pusher member 320, the support tube 340, and the cover member 330 can be provided as a plurality of nested, telescoping members with a common longitudinal axis 350 as illustrated in FIG. 3A. The carrier member 310 can be configured to receive and support the closure element (not shown). While being disposed on the carrier member 310, the closure element can be deformed from the natural or memory set shape and configuration to a retention or delivery configuration, which retention or delivery configuration can be different in different embodiments as described herein. Being disposed substantially about, and supported by, an outer periphery 312b of the carrier member 310, the closure element can be substantially in axial alignment with the carrier member 310 with the tines 520 pointed an a variety of directions ranging from being pointed substantially distally, at about 45 degrees, about 90 degrees, about 120 degrees, to about 180 degrees or substantially proximally.

The position of the closure element with regard to the tube set can vary depending on various factors, such as the flexibility of the tube set or the distal end of the tube set. As such, the closure element can be located in a storage configuration (e.g., tubular) at a proximal position, distal position, or any position therebetween.

As shown in FIG. 3A, the carrier assembly 300 includes at least one bending member 301 (e.g., 301a and 301b). Each bending member 301 is shown to be disposed internally to the support member 340; however, the bending member 301 could be placed between the support member 340 and the carrier member 310, between the carrier member 310 and the pusher member 320, between the pusher member 330 and the cover member 330, or even external to the cover member 330 or internal to the support member 340 as shown by the dashed lines. The bending members 301a,b can bend the carrier assembly 300 by one bending member 301a being pushed while the other bending member 301b is held or pulled, or vice versa. Alternatively, the bending member 301a can be pulled while the other bending member 301b is pushed or held. Optionally, each bending member 301a,b can be coupled to a member of the carrier assembly 300 to facilitate bending. As shown, the first bending member 301a is coupled to a first bending point 302a of the support member 340 and the second bending member is coupled to a second bending point 302b. For example, the first bending member 301a is contracted so as to pull the bending point 302a in a proximal direction, and the second bending member 301b is extended so as to push the second bending point 302b in a distal direction. The simultaneous movement of the bending member 301a,b can selectively bend the carrier assembly 300 so as to point into the fistula.

Figure 3B:
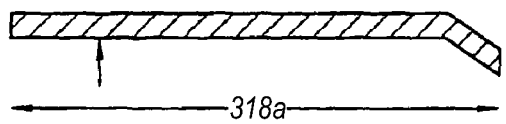
FIG. 3B illustrates an embodiment of a carrier member for the carrier assembly of FIG. 3A.

FIG. 3B illustrates an embodiment of a carrier member 310. The carrier member 310 can be formed as a substantially rigid, semi-rigid, or flexible tubular member; however, it can be advantageous for the distal end region 310b of the carrier member 310 to have sufficient flexibility to be bent and placed at or within a fistula. For example, the carrier member 310 can be longitudinally stiffer and radially or laterally flexible. Additionally, the carrier member 310 can have a proximal end region 310a and a predetermined length 318a and a predetermined cross-section 318b, both of which can be of any suitable dimension. The carrier member 310 also can have an external surface 312b and an internal surface 312a that defines a lumen 314 that extends substantially between the proximal end region 310a and the distal end region 310b and that is configured to slidably receive at least a portion of the tubular body 210 of the locator assembly 200. Although the cross-section 318b of the carrier member 310 generally is substantially uniform, the distal end region 310b of the carrier member 310 can have a cross-section that increases distally, as illustrated in FIGS. 3A-3B, for substantially uniformly expanding the closure element during deployment into tissue of the fistula. To deploy the closure element without expansion, the distal end region 310b can be formed with a cross-section (not shown) that is substantially uniform, which can be of similar dimensions of the proximal end region 310a. Although shown and described as having the cross-section that increases distally for expanding the closure element, it will be understood that the distal end region 310b of the carrier member 310 can be provided with the substantially-uniform cross-section.

Figure 3C:
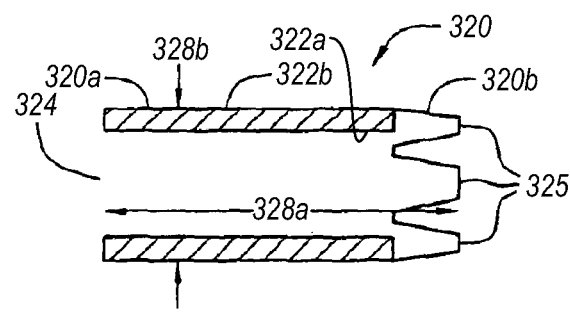
FIG. 3C illustrates an embodiment of a pusher member for the carrier assembly of FIG. 3A.

FIG. 3C illustrates an embodiment of a pusher member 320 that is configured to distally deploy the closure element for repairing a fistula. The pusher member 320 has a proximal end region 320a and a distal end region 320b, and includes a predetermined length 328a and a predetermined cross-section 328b, both of which can be of any suitable dimension. Also, the pusher member 320 can include an external surface 322b and an internal surface 322a that defines a lumen 324 for slidably receiving the carrier member 310 such that the distal end region 320b of the pusher member 320 is offset proximally from the distal end region 310b of the carrier member 310 as shown in FIG. 3A. As desired, the predetermined length 328a of the pusher member 320 can be shorter than, greater than, or substantially equal to the predetermined length 318a of the carrier member 310. The predetermined length 328a of the pusher member 320, however, can be less than the predetermined length 318a of the carrier member 310 such that the carrier member 310 and the pusher member 320 at least partially define a space 360 distal to the distal end region 320b of the pusher member 320 and along the periphery 312b of the carrier member 310. The space 360 is also referred to as the garage 360 in which the closure element is retained within the closure element applier 100.

The pusher member 320 can be a substantially rigid, semi-rigid, or flexible tubular member; however, the distal end region 320b can be flexible as described herein so that the tip 220 (i.e., locator 220) can be placed at or within the fistula. The cross-section 328b of the pusher member 320 can be substantially uniform, and the distal end region 320b of the pusher member 320 can include one or more longitudinal extensions 325, which extend distally from the pusher member 320 and along the periphery 312b of the carrier member 310 as shown in FIG. 3C. The longitudinal extensions 325 can be biased such that the longitudinal extensions 325 extend generally in parallel with common longitudinal axis 350 of the carrier assembly 300. The longitudinal extensions 325 are sufficiently flexible to bend for placement of the tip 220 with respect to the fistula and to expand radially, and yet sufficiently rigid to inhibit buckling, as the distal end region 320b is directed distally along the carrier member 310 and engage the distally-increasing cross-section of the distal end region 310b of the carrier member 310 to deploy the closure element. For example, the pusher member 320 and longitudinal extensions 325 can be longitudinally stiffer and radially or laterally flexible.

Figure 3D:
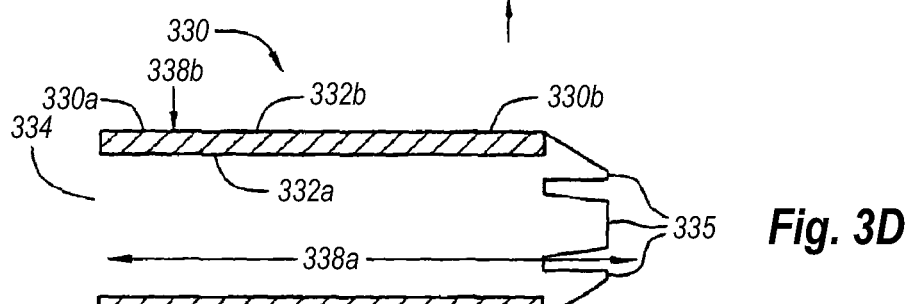
FIG. 3D illustrates an embodiment of a cover member for the carrier assembly of FIG. 3A.

FIG. 3D illustrates an embodiment of a cover member 330 configured to retain the closure element substantially within the carrier assembly 300 prior to deployment. Being coupled with, and slidable relative to, the pusher member 320, the cover member 330 has a proximal end region 330a and a distal end region 330b and includes a predetermined length 338a and a predetermined cross-section 338b, both of which can be of any suitable dimension. The cover member 330 can also be formed as a substantially rigid, semi-rigid, or flexible tubular member, and the distal end region 330b can be flexible for placement of the tip 220 with respect to a fistula as described herein. For example, the cover member 330 can be longitudinally stiffer and radially or laterally flexible. Additionally, the cover member 330 can have an inner periphery 332a that defines a lumen 334, and an outer periphery 332b. The lumen 334 can extend substantially between the proximal and distal end regions 330a, 330b of the cover member 330 and can be configured to slidably receive at least a portion of the pusher member 320. When the cover member 330 is properly positioned within the carrier assembly 300, the distal end region 330b can be configured to extend over the space 360, thereby defining an annular cavity 370 for receiving and retaining the closure element. The annular cavity 370 along with the space 360 can be referred to as the garage because they cooperate to retain the closure element within the carrier assembly 300.

The cross-section 338b of the cover member 330 can be substantially uniform, and the distal end region 330b of the cover member 330 can include one or more longitudinal extensions 335, which extends distally from the cover member 330 and along an outer periphery 322b of the pusher member 320. Although the longitudinal extensions 335 can extend generally in parallel with common longitudinal axis 350, the longitudinal extensions 335 can be biased such that the plurality of longitudinal extensions 335 extend substantially radially inwardly as illustrated in FIGS. 3A and 3D. Thereby, the longitudinal extensions 335 can at least partially close the lumen 334 substantially adjacent to the distal end region 330b of the cover member 330. To permit the closure element to be deployed from the annular cavity 370, the longitudinal extensions 335 can be sufficiently flexible to expand radially to permit the distal end region 310b of the carrier member 310 to move distally past the cover member 330 to open the annular cavity 370 such that the distal end region 330b no longer extends over the space 360. This effectively opens the garage so that the closure element can be deployed into the tissue of the fistula.

When the carrier assembly 300 is assembled as the plurality of nested, telescoping members as shown in FIG. 3A, the carrier member 310 can be at least partially disposed within, and slidable relative to, the lumen 324 of the pusher member 320. The pusher member 320, in turn, can be at least partially disposed within, and slidable relative to, the lumen 334 of the cover member 330. To couple the carrier assembly 300 with the locator assembly 200, the tubular body 210 of the locator assembly 200 can be at least partially disposed within, and slidable relative to, the lumen 314 of the carrier member 310. The corresponding positioning of the locator assembly 200 and carrier assembly 300 is shown in FIG. 2A. The longitudinal axis of the locator assembly 200 can be substantially in axial alignment with the common longitudinal axis 350 of the carrier member 310, the pusher member 320, the cover member 330, and the support tube 340.

Figure 3E:
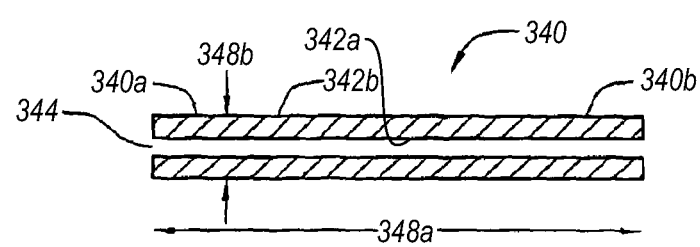
FIG. 3E illustrates an embodiment of a support member for the carrier assembly of FIG. 3A.

It will be appreciated that the tube set 305 can optionally include a support member 340 as shown in FIGS. 3A and 3E. The carrier assembly 300 can advantageously include the support member 340, for example, if the tubular body 210 of the locator assembly 200 is not sufficiently rigid or under other circumstances in which support for the tubular body 210 might be desirable. It also will be appreciated that the support member 340 also can be configured to inhibit the plurality of longitudinal extensions 335, which extend from the distal end region 330b of the cover member 330, from expanding prematurely prior to the closure element being deployed. The support member 340 is configured to slidably receive the tubular body 210 of the locator assembly 200 and to provide radial support for the distal end region 210b of the tubular body 210 when the locator assembly 200 is coupled with the carrier assembly 300.

The support member 340 can be formed as a substantially rigid, semi-rigid, or flexible tubular member having a proximal end region 340a and a distal end region 340b. The distal end region 340b can be sufficiently flexible so as to allow for the tip 220 to be placed at or within a fistula. For example, the support member 340 can be longitudinally stiffer and radially or laterally flexible. The support member 340 includes an outer surface 342b and an inner surface 342a that defines a lumen 344 that extends substantially between the proximal end region 340a and the distal end region 340b. The lumen is configured to slidably receive and support at least a portion of the tubular body 210 of the locator assembly 200. The support member 340, in turn, can be at least partially slidably disposed within the lumen 314 of the carrier member 310 such that the tubular body 210 of the locator assembly 200 may be coupled with, and slidable relative to, the carrier member 310 in the manner described herein. The support member 340 can have a predetermined length 348a and a predetermined cross-section 348b, both of which can be of any suitable dimension, and the cross-section 348b can be substantially uniform. Although shown and described as being substantially separate for purposes of illustration, it will be appreciated that the carrier member 310, the pusher member 320, the cover member 330, and/or the support member 340 can be provided, in whole or in part, as one or more integrated assemblies.

FIGS. 4A-4D illustrates an embodiment of a medical device 100 including a housing 380 that stores components for actuating the deployment of the closure element (not shown). The housing 380 can be formed as an elongate member with a longitudinal axis 386. Additionally, the housing 380 can have an outer surface 382, and includes a proximal end region 380a and a distal end region 380b. While not specifically shown, when the medical device 100 is properly assembled, the tubular body 210 of the locator assembly 200 can be at least partially disposed within the tube set 305 of the carrier assembly 300. The distal end region 210b of the tubular body 210 either extends or is extendable beyond the distal end regions 310b, 320b, 330b, and/or 340b (FIG. 4C) of the tube set 305. Further, the proximal end region 210a of the tubular body 210 and the proximal end regions 310a, 320a, 330a, and/or 340a (FIGS. 3A-3E) of the tube set 305 are at least partially disposed within, and slidable relative to, the housing 380. By being configured to slidably retain the respective proximal end regions 210a, 310a, 320a, 330a, and 340a, the housing 380 supports the tube set 305 and can have one or more handles 390 to facilitate use of the medical device 100. The handles 390 extend substantially radially from the outer surface 382 of the housing 380 and can be provided in any shape, size, orientation, and manner known in the art.

The locator control system 240 and at least one control member 250 (both shown in FIG. 2D) of the locator assembly 200, and a switching system 450 of the triggering system 400 can be accessible external to the housing 380 as shown in FIGS. 4A-4D. The tube set 305 can be functionally coupled include a switching system 450 so as to operate and control the members of the tube set 305 for deployment of the closure element.

Figure 4A:
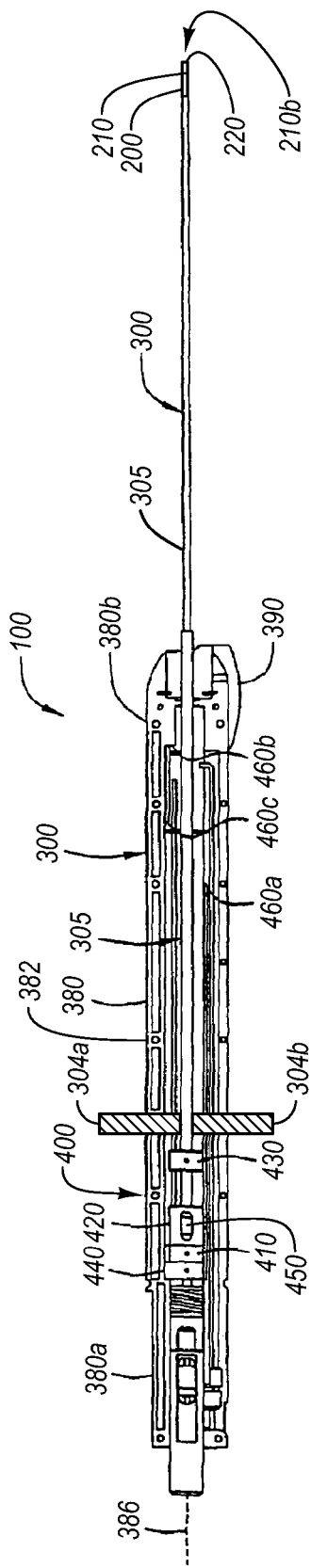
FIGS. 4A-4C illustrate different cross-sectional side views of an embodiment of a medical device configured to deliver a closure element to repair a fistula.
Figure 4B:
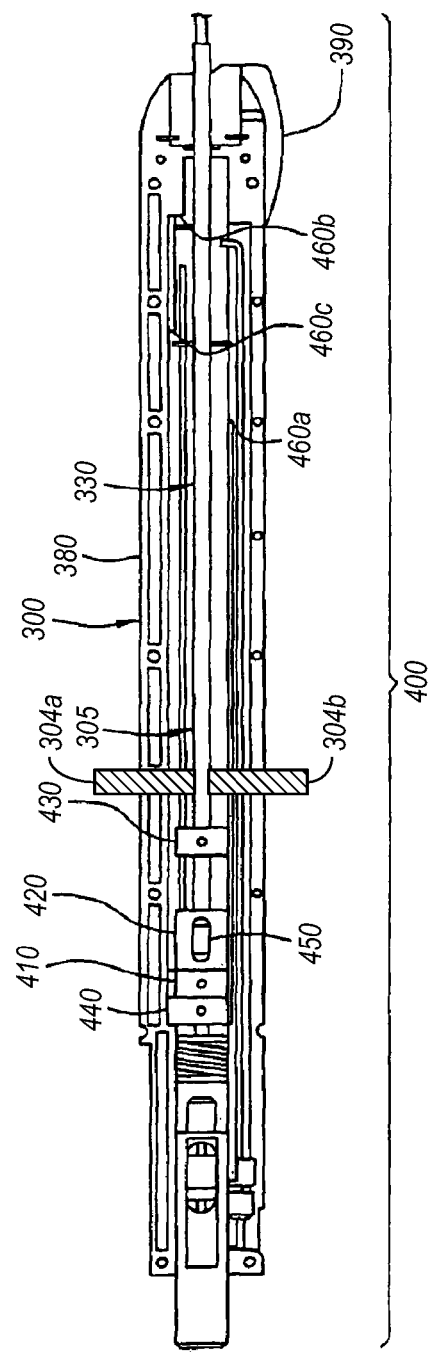
Figure 4C:
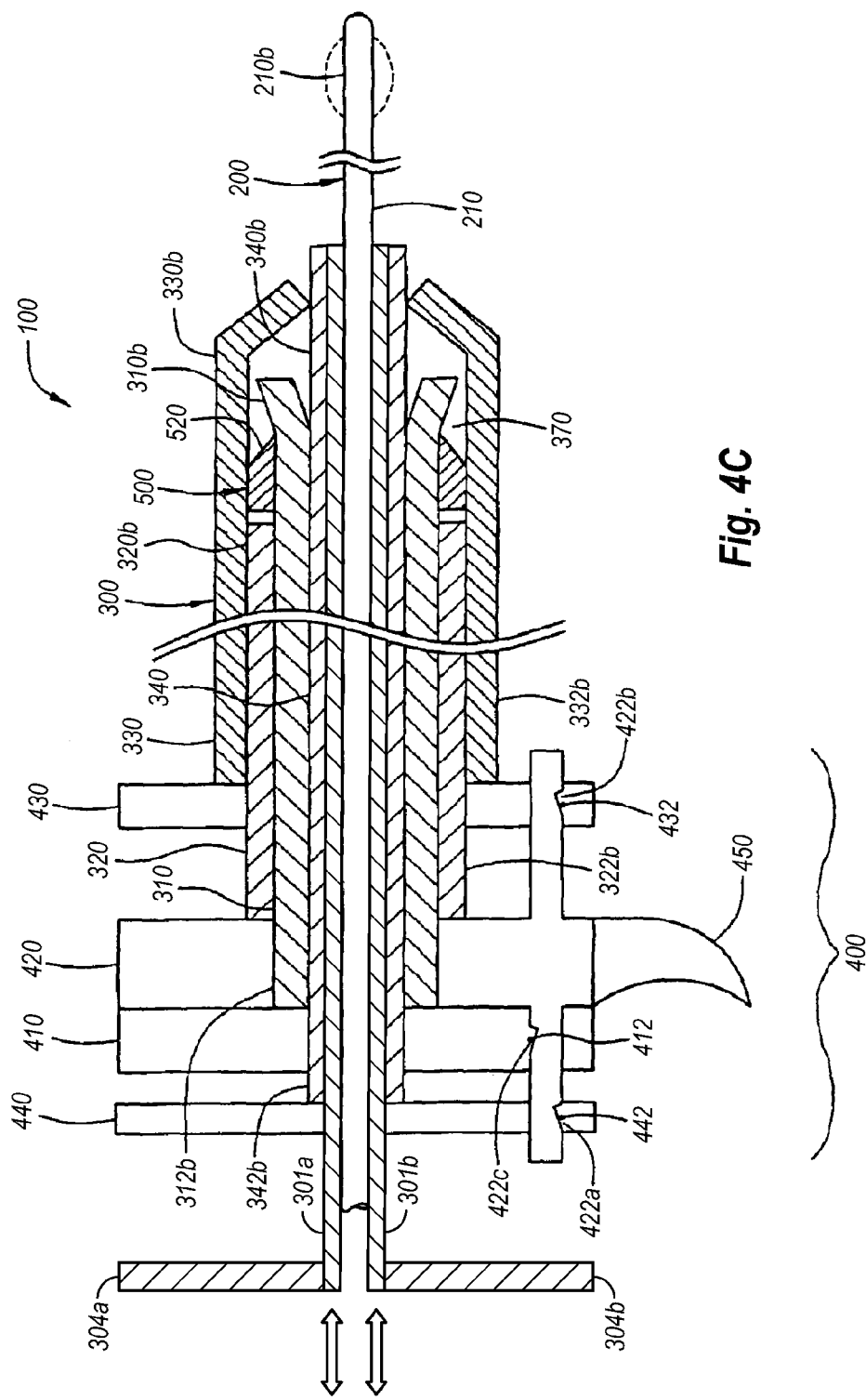

FIGS. 4A-4C illustrate a pair of bending levers 304a,b that protrude through the housing 380. The bending levers 304a,b are coupled to the bending members 301a,b. The bending members 301a,b can be coupled to any member of the tube set 305, and are shown to be coupled to the support member 340. The bending members 301a,b can be coupled to a single point or at any points along the support member. In operation, axially sliding one or both of the bending levers 304a,b causes the bending members 301a,b to also slide axially so as to bend the carrier assembly 300 by compressing or extension of one side of the carrier assembly 300 such as through the compression of the support member 340. The bending function is accomplished by one bending member 301a being pushed while the other bending member 301b is held or pulled, or vice versa, by sliding one of the bending levers 304a,b relative to the other bending lever. Alternatively, the bending member 301a can be pulled by pulling the bending lever 304a while the other bending member 301b is pushed or held by controlling the bending lever 304b. As shown, the first bending member 301a is coupled to a first bending lever 304a, and the second bending member is coupled to a second bending lever 304b.

Figure 5A:
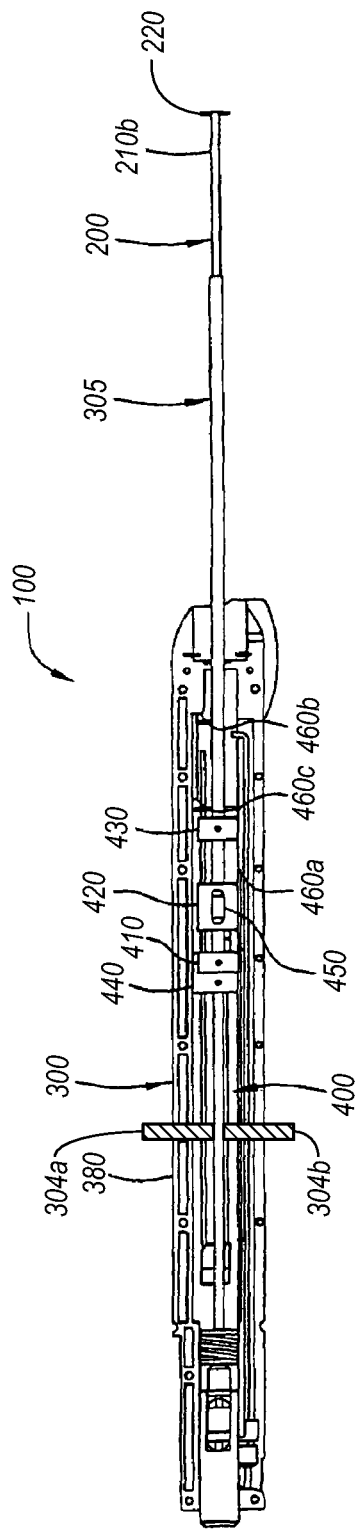
FIG. 5A illustrates the medical device of FIGS. 4A-4D as the carrier assembly of FIG. 3A moves distally from an initial predetermined position.
Figure 5B:
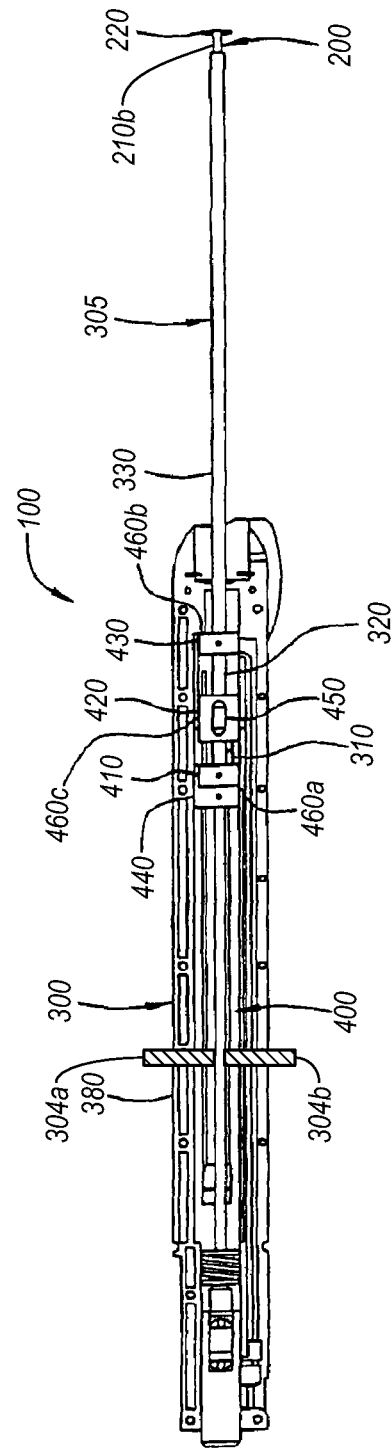
FIG. 5B illustrates the medical device of FIGS. 4A-4D as the carrier assembly reaches a first predetermined position.
Figure 5C:
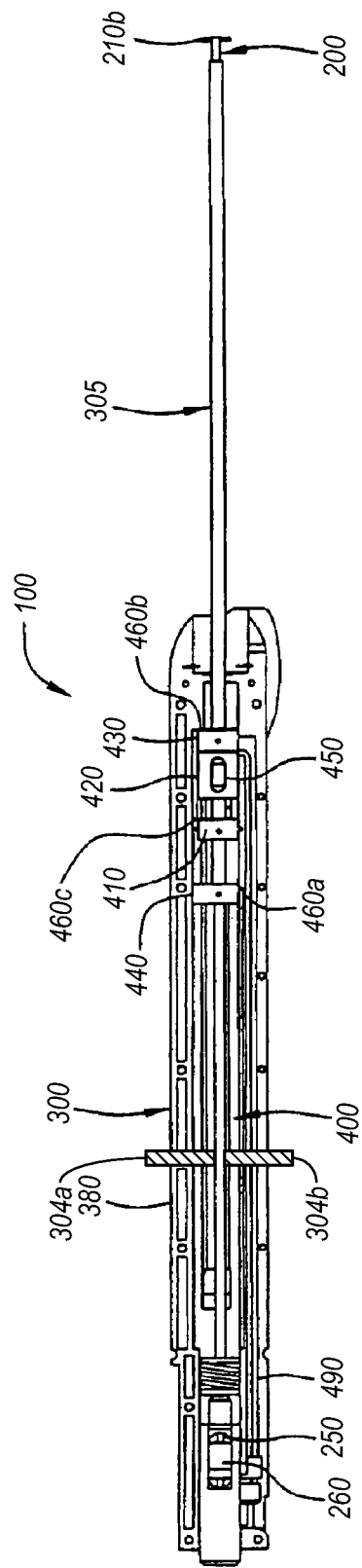
FIG. 5C illustrates the medical device of FIGS. 4A-4D as the carrier assembly reaches a second predetermined position.
Figure 5D:
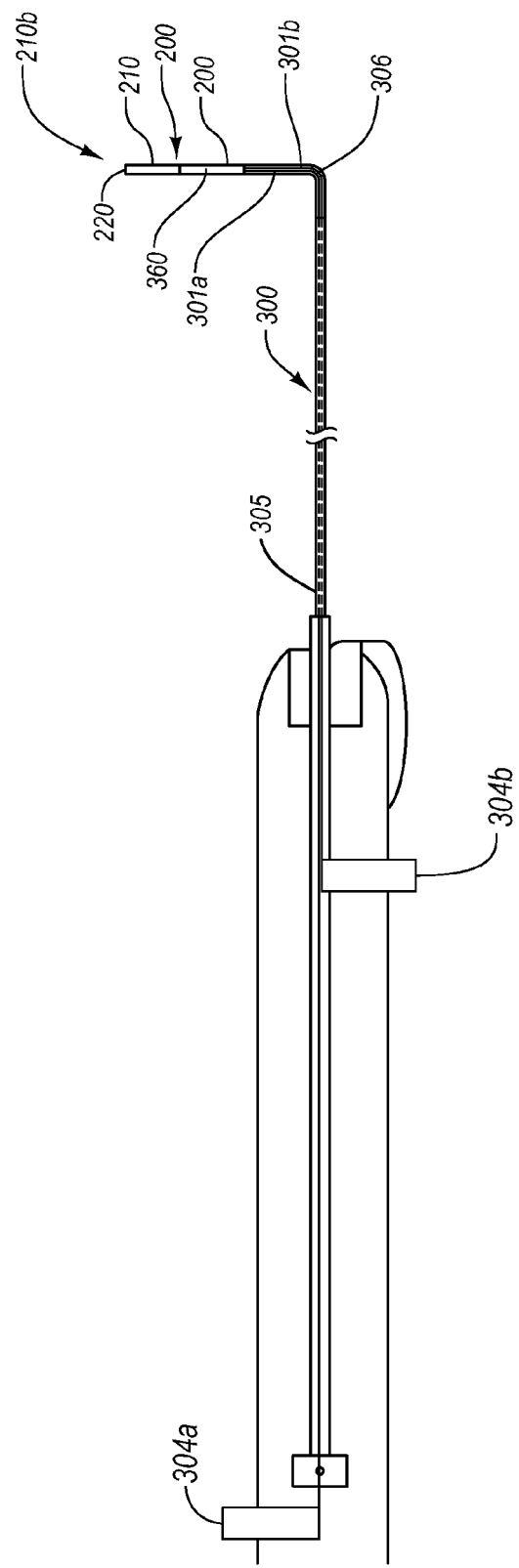
FIG. 5D illustrates the medical device of FIGS. 4A-4D as the carrier assembly is bent in a first direction.

As shown in FIG. 5D, when the first bending member 301a is pulled in a proximal direction by proximally pulling the first bending lever 304a in a proximal direction, and/or the second bending member 301b is pushed in a distal direction by distally pushing the second bending lever 304b in a distal direction, the carrier assembly 300 is bent in a first direction. Accordingly, a bending portion 306 of the carrier assembly 300 is shown to bend so that the locator 220 points toward the fistula.

Figure 5E:
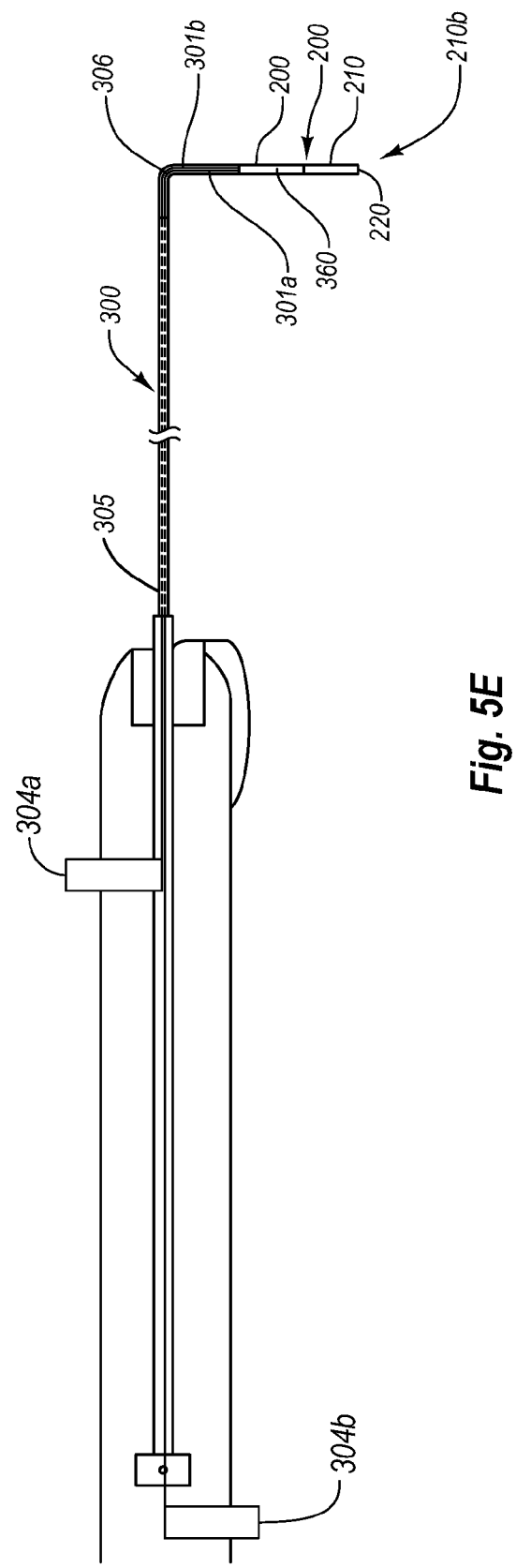
FIG. 5E illustrates the medical device of FIGS. 4A-4D as the carrier assembly is bent in a second direction.

As shown in FIG. 5E, when the first bending member 301a is pushed in a distal direction by distally sliding the first bending lever 304a in a distal direction, and/or the second bending member 301b is pulled in a proximal direction by proximally sliding the second bending lever 304b in a proximal direction, the carrier assembly 300 is bent in a second direction. Accordingly, a bending portion 306 of the carrier assembly 300 is shown to bend so that the locator 220 points toward the fistula.

The simultaneous relative movement of the bending levers 304a,b can selectively bend the carrier assembly 300 so as to point into the fistula. Each bending member 301 is shown to be disposed internally to the support member 340; however, the bending member 301 could be placed between the support member 340 and the carrier member 310, between the carrier member 310 and the pusher member 320, between the pusher member 330 and the cover member 330, or even external to the cover member 330 or internal to the support member 340 as shown in the dashed lines of FIG. 3A.

Alternatively, the bending members 301 can be slid distally and/or proximally by being attached to some other actuating mechanism. Accordingly, the bending levers 304 (e.g., axially sliding levers) can be configured into a different actuating mechanism or can be coupled to a different actuating mechanism. For example, the bending members 301 and/or the bending levers 304 can be coupled to a rotating dial, screw and thread mechanism, worm gear, laterally-moving lever, or the like to facilitate proximal or distal movements of the bending members 301 that causes lateral and/or radial bending of the carrier assembly 300 so that the locator 220 and the closure element (not shown) is directed toward a fistula.

Additionally, while only two bending members 301 and bending levers 304 are shown in the figures, any number of bending members, bending levers, or other actuating components that can bend the carrier assembly 300 can be included. This can include 1, 2, 3, 4, 5, 6, or more bending members, bending levers, or other components that facilitate bending by axial motion. Also, the bending members 301, bending levers 304, or other axially moving members can be present in pairs disposed opposite from each other as illustrated. Bending member pairs can be disposed oppositely so that the relative movement bends the carrier assembly in a first direction or in the opposite second direction.

Referring back to FIGS. 4A-4D, a triggering system 400 can be disposed substantially within the housing 380. The triggering system 400 can be configured to control the relative axial movement and/or positioning of the respective distal end regions 310b, 320b, 330b, and 340b of the tube set 305 and/or the distal end region 210b and/or tip 220 of the locator assembly 200. By being coupled with the proximal end regions 210a, 310a, 320a, 330a, and/or 340a, the triggering system 400 can control the relative axial movement of the distal end regions 210b, 310b, 320b, 330b, and/or 340b in any manner, such as by being activated by the switching system 450. Actuation of the triggering system 400 and switching system 450 can induce axial motion, such as distal motion, with respect to one or more of the distal end regions 210b, 310b, 320b, 330b, and/or 340b. Axial motion of one or more of the carrier member 310, the pusher member 320, the cover member 330, and the support member 340 and/or the tubular body 210 can be attained, for example, by applying an axial force to the switching system 450.

Also, the triggering system 400 and switching system 450 can be configured for providing transverse or radial movement or bending from the central axis 386 that allows the distal ends of the members of the tube set 305 to be bent away from the longitudinal axis 386, which allows for enhanced placement of the tip 220 with respect to the fistula.

To facilitate monitoring of the positioning of the carrier assembly 300 and/or the closure element, one or more of the distal end regions 210b, 310b, 320b, 330b, and/or 340b may include radiopaque markers (not shown) or may be wholly or partially formed from a radiopaque material.

The triggering system 400 can be configured to overcome internal resistance such that the relative axial movement and/or positioning of the respective distal end regions 310b, 320b, 330b, and 340b of the tube set 305 and/or the distal end region 210b of the locator assembly 200 are controlled in accordance with a predetermined manner when the triggering system 400 is activated. Thereby, axial movement and/or positioning of the distal end regions 310b, 320b, 330b, 340b, and/or 210b can be initiated when at least a predetermined quantity of force is applied to the switching system 450. Stated somewhat differently, a force that is less than the predetermined quantity generally may be insufficient to activate the triggering system 400; whereas, when the force increases to a level that is greater than or substantially equal to the predetermined quantity, the triggering system 400 is configured to activate, move and/or position the distal end regions 310b, 320b, 330b, 340b, and/or 210b in accordance with the predetermined manner. The triggering system 400, once activated, can continue to move and/or position the distal end regions 310b, 320b, 330b, 340b, and/or 210b in accordance with the predetermined manner until the closure element 500 is deployed.

The triggering system 400, for example, can include one or more sets of cooperating detents for coupling the axial motion of the distal end regions 310b, 320b, 330b, and 340b in accordance with a predetermined manner when the triggering system 400 is activated. The term "detents" refers to any combination of mating elements, such as blocks, tabs, pockets, slots, ramps, locking pins, cantilevered members, support pins, and the like, that may be selectively or automatically engaged and/or disengaged to couple or decouple the carrier member 310, the pusher member 320, the cover member 330, and the support member 340 relative to one another and with respect to the triggering system 400, switching system 450, and housing 380. It will be appreciated that the cooperating detents as illustrated and described below are merely exemplary and not exhaustive. For example, the cooperating detents can include a first set of cooperating blocks and pockets for releasably coupling the support member 340, the carrier member 310, the pusher member 320, and the cover member 330. When the carrier assembly 300 reaches a first predetermined distal position, the support member 340 can be decoupled from the carrier member 310, the pusher member 320, and the cover member 330 and can be substantially inhibited from further axial movement. Thereby, the carrier member 310, the pusher member 320, and the cover member 330 may continue to be directed distally as the support member 340 remains substantially stationary.

As shown in FIGS. 4A-4C, the cooperating detents can include a carrier block 410, a pusher block 420, a cover block 430, and a support block 440, which can be configured to couple and decouple in accordance with the predetermined manner. For example, the carrier block 410 can be disposed on the proximal end region 310a of the carrier member 310 and can include a carrier pin 412 that extends from the carrier block 410; whereas, the proximal end region 330a of the cover member 330 and the proximal end region 340a the support member 340 are respectively coupled with the cover block 430 and the support block 440. A cover pin 432 can extend from the cover block 430, and the support block 440 can have a support pin 442, which extends from the support block 440. The support pin 442, the cover pin 432, and the carrier pin 412 each can be formed from a substantially rigid material, such as an alloy of nickel-titanium.

The pusher block 420 can be disposed on the proximal end region 320a of the pusher member 320 and forms a support slot 422a, a cover slot 422b, and a carrier slot 422c. The support slot 422a can be configured to receive and releasable engage the support pin 442 by which the support member 340 can be coupled with, and decoupled from, the pusher member 320. The cover member 330 can be coupled with, and decoupled from, the pusher member 320 via the cover slot 422b, which is configured to receive and releasable engage the cover pin 432. The carrier slot 422c can be configured to receive and releasable engage the carrier pin 412 such that the carrier member 310 can be coupled with, and decoupled from, the pusher member 320. The carrier block 410, the pusher block 420, the cover block 430, and the support block 440 can be respectively disposed substantially on the outer peripheries (i.e., outer surfaces) 312b, 322b, 332b, and 342b of the members of the tube set 305, and can be configured to couple and decouple in accordance with the predetermined manner.

The triggering system 400 can further include one or more stops for engaging the pusher block 420, the cover block 430, and/or the support block 440, respectively. As illustrated in FIGS. 4A-4B, a support stop 460a, a cover stop 460b, and a carrier stop 460c each can be formed in the housing 380 and are configured to receive, and substantially inhibit further movement of, the support block 440, the cover block 430, and the carrier block 410, respectively, in accordance with the predetermined manner. For example, when an axial force is applied to the tube set 305 via the switching system 450, the cover block 430 can move distally within the housing 380, and the cover block 430 approaches the cover stop 460b. Upon being received by the cover stop 460b, the cover block 430 can be substantially locked in place, substantially preventing any further motion of the cover block 430.

Resisting the axial force, the cover pin 432 can provide a static load while the axial force is less than the predetermined quantity of force. As the axial force increases to a level that is greater than or substantially equal to the predetermined quantity, the cover pin 432 can be displaced from the cover slot 422b, decoupling the cover member 330 from the carrier member 310, the pusher member 320, and the support member 340. Creating the internal resistance to be overcome by the triggering system 400, the static forces provided by the pins 442, 432, and 412 is approximately proportional to a composition and cross-section of the respective pins 442, 432, and 412 and/or a depth and a slope of the respective slots 422a, 422b, and 422c. As desired, the pins 442, 432, and 412 can be configured to provide static loads that are differing and/or substantially uniform.

FIG. 4C illustrates an embodiment of the medical device 100 having the tube set 305 and the closure element 500 being retained within the garage 370 and adjacent to the distal end 320b of the pusher tube 320. The closure element 500 can be configured into a retention orientation and slidably received over the distally-increasing cross-section 318b of the distal end region 310b of the carrier member 310 and disposed about the outer surface 312 of the carrier member 310 within the garage 370. If the closure element 500 has a reduced cross-section that is less than the cross-section 318b of the distally-increasing cross-section 318b, the closure element 500 can be temporarily radially deformed to a wider diameter in order to be received over the distal end region 310b. Also, as the closure element 500 is received over the distal end region 310b, the opposing tines 520 are oriented toward the distal end region 310b. The closure element 500 on the carrier member 310 can form the substantially tubular closure element 500 in the manner described in more detail herein. Also, the closure element 500 can be oriented so that the tines are pointed substantially in any direction, such as about 45 degrees, about 90 degrees, about 120 degrees and about 180 degrees or substantially proximally. The size of the garage and configuration of the tube set 305 can be modulated to accommodate a closure element 500 in substantially any retention orientation, which can include members of the tube set 305, such as the pusher tube 320 having tapered, slotted, grooved, curved, inclined, declined, or other similar faces that contact the closure element 500.

After being received over the distal end region 310b, the closure element 500 can be disposed in the garage 370, and the tines 520 are directed substantially distally. As desired, one or more of the tines 520 can be disposed proximally of the distally-increasing cross-section 318b of the distal end region 310b, and/or can be at least partially disposed upon, and contact, the distally-increasing cross-section 318b of the distal end region 310b. To improve the engagement between the closure element 500 and the tissue of the fistula, the closure element can be disposed on the carrier member 310 such that the tines 520 define a first plane that is substantially perpendicular to a second plane defined by the switching system 450 and/or the handles 390 (collectively shown in FIG. 4D).

Once disposed in the garage 370, the closure element 500 can be retained on the outer surface 312b of the carrier member 310 when distal end region 310b of the carrier member 310 and the distal end region 320b of the pusher member 320 are slidably received within the lumen 334 of the cover member 330. When the cover member 330 is properly positioned within the carrier assembly 300, the distal end region 330b of the cover member 330 can extend over the closure element 500 and define the garage 370 (i.e., annular cavity 370) for retaining the closure element. As such, the closure element 500 is disposed substantially between the outer surface 312b of the carrier member 310 and the inner surface 332a of the cover member 330 such that the closure element 500 maintains the substantially tubular configuration with the tines 520 being directed substantially distally. As desired, the cover member 330 may radially compress the closure element 500 maintains a compressed tubular configuration. The body of the closure element 500 can be disposed distally of the distal end region 320b of the pusher member 320, or can engage the distal end region 320b, as desired.

Figure 4D:
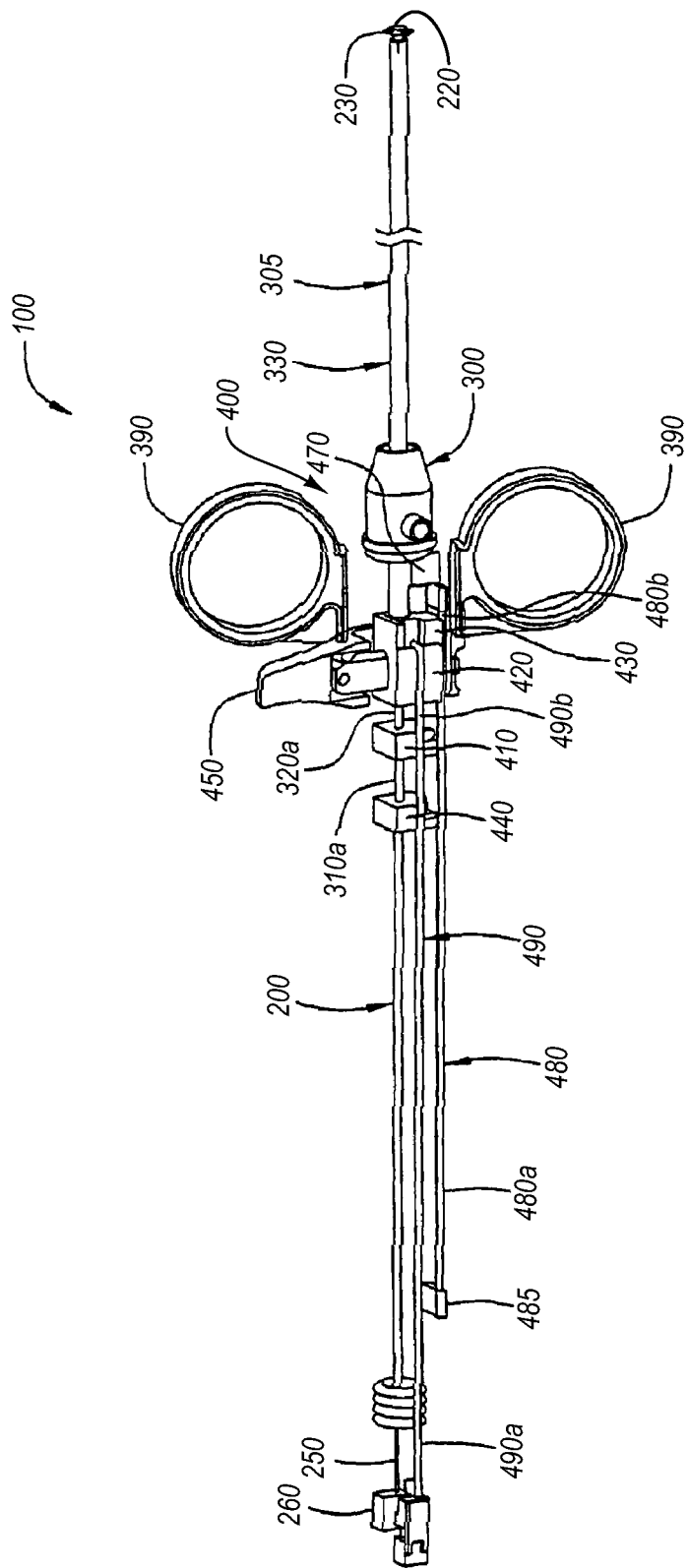
FIG. 4D illustrates a detailed cross-sectional side view of a triggering system of the medical device.

Turning to FIG. 4D, the triggering system 400 may further include a tube release system 470 for inhibiting inadvertent advancement of the tube set 305. The tube release system 470 is coupled with a tube release member 480, such as a rod, wire, or other elongate member. The tube release member 480 has a proximal end region 480a that is disposed substantially between the pusher block 420 and the housing 380 (shown in FIG. 4A) and a distal end region 480b that is coupled with the tube release system 470. Optionally, a tab 485 is coupled with the proximal end region 480a of the tube release member 480, and a pin (not shown) extends from the pusher block 420 and is disposed substantially between the tab 485 and a groove (not shown) formed in the housing 380. The tube release system 470 is configured to release the tube set 305 when the tube release member 480 is moved proximally, freeing the pusher block 420.

A locator release system 490 for permitting the locator 220, the expansion elements 230, and/or the substantially flexible members 231 of the locator assembly 200 to be manipulated and transition from the expanded state to the unexpanded state can be included with the triggering system 400. The locator release system 490 can include a rod, wire, or other elongate member and has a proximal end region 490a and a distal end region 490b. The proximal end region 490a of the locator release system 490 can be coupled with, and configured to activate, the locator control system 240 (shown in FIG. 2D), and the distal end region 490b extends beyond the pusher block 420. Thereby, when the pusher block 420 is advanced during deployment of the closure element 500, the control block 260 can be disengaged such that the distal end region 210b, locator 220, the expansion elements 230, and/or the substantially flexible members 231 of the locator assembly 200 to transition from the expanded state to the unexpanded state.

The operation of the triggering system 400 in accordance with one predetermined manner is illustrated in FIGS. 5A-5C. As shown in FIG. 5A, the distal end region 210b of the locator assembly 200 has been positioned as desired and the locator 220 has transitioned from the unexpanded state to the expanded state. While the locator control system 240 (shown in FIG. 2D) maintains the distal end region 210b in a desired position and the locator 220 in the expanded state, a distally-directed axial force can be applied to the triggering system 400 via the switching system 450. Once the tube release member 480 (shown in FIG. 4D) has been moved proximally to free the pusher block 420, the tube set 305 can be substantially freely slidable within the housing 380 and responds to the axial force by sliding distally from an initial predetermined position to a first predetermined position.

In the initial predetermined position, the carrier member 310, the pusher member 320, the cover member 330, and the support member 340 can be coupled via the slots 422c, 422b, and 422a (shown in FIG. 4C) and the pins 412, 432, and 442 (shown in FIG. 4C). Stated somewhat differently, the support pin 442, the cover pin 432, and the carrier pin 412 can be respectively disposed within, and engaged by, the support slot 422a, the cover slot 422b, and the carrier slot 422c such that the carrier block 410, the pusher block 420, the cover block 430, and the support block 440 are coupled as illustrated in FIG. 4C. Therefore, the carrier member 310, the pusher member 320, the cover member 330, and the support member 340 each can slide distally from the initial predetermined position to the first predetermined position in response to the axial force.

FIG. 5B illustrates the positions of the carrier member 310, the pusher member 320, the cover member 330, and the support member 340 (FIG. 4C) upon reaching the first predetermined position. In the first predetermined position, the support block 440 and the cover block 430 can respectively engage the support stop 460a and the cover stop 460b. Thereby, the support stop 460a can receive, and substantially inhibit further movement of, the support block 440 and, therefore, the support member 340; whereas, the cover stop 460b receives, and substantially inhibits further movement of, the cover block 430 and, therefore, the cover member 330. Although the support block 440 and the cover block 430 can engage the support stop 460a and the cover stop 460b in the first predetermined position, it will be appreciated that the support block 440 can engage the support stop 460a and the cover block 430 can engage the cover stop 460b in different predetermined positions. In other words, the predetermined manner can include any number of predetermined positions, each predetermined position being associated with any number of the blocks 410, 420, 430, and 440 engaging any number of relevant stops 460a, 460b, and 460c.

To continue distally from the first predetermined position, the carrier member 310 and the pusher member 320 can be decoupled from the cover member 330 and the support member 340 by disengaging the support pin 442 and the cover pin 432 from the support slot 422a and the cover slot 422b, respectively. In the manner described in more detail above with reference to FIGS. 4A-4C, the support pin 442 and the cover pin 432 each resist the axial force. While the axial force is less than the combined static force provided by the support pin 442 and the cover pin 432, the carrier member 310 and the pusher member 320 remain coupled with the cover member 330 and the support member 340. As the axial force increases to a level that is greater than or substantially equal to the combined static force, the support pin 442 and the cover pin 432 are respectively displaced from the support slot 422a and the cover slot 422b, decoupling the carrier member 310 and the pusher member 320 from the cover member 330 and the support member 340. Thereby, the cover member 330 and the support member 340 can be inhibited from further distal movement and remain substantially stationary; whereas, the carrier member 310 and the pusher member 320 can proceed distally toward a second predetermined position.

The pusher member 320 and the carrier member 310 can continue distally until the second predetermined position is reached as shown in FIG. 5C. In the second predetermined position, the carrier block 410 can engage the carrier stop 460c. Whereby, the carrier stop 460c can receive, and substantially inhibit further movement of, the carrier block 410 and, therefore, the carrier member 310. To continue distally from the second predetermined position, the pusher member 320 can be decoupled from the carrier member 310 by disengaging the carrier pin 412 from the carrier slot 422c. In the manner described in more detail above with reference to FIG. 4B-C, the carrier pin 412 resists the axial force. While the axial force is less than the static force provided by the carrier pin 412, the pusher member 320 remains coupled with the carrier member 310.

As the axial force increases to a level that is greater than or substantially equal to the static force, the carrier pin 412 can be displaced from the carrier slot 422c, decoupling the pusher member 320 from the carrier member 310. Thereby, the carrier member 310 can be inhibited from further distal movement and remains substantially stationary; whereas, the pusher member 320 proceeds distally to deploy the closure element 500 and to activate the locator release system 490 (shown in FIG. 4D) such that the locator 220, the expansion elements 230, and/or the substantially flexible members 230' of the locator assembly 200 transition from the expanded state to the unexpanded state. The axial force that is applied to overcome the static force associated with the first predetermined position is sufficient to overcome the static forces associated with the subsequent predetermined positions, to deploy the closure element 500, and to activate the locator release system 490 such that the triggering system 400 operates in one substantially-continuous motion.

It will be appreciated that the triggering system 400 can include an energy storing element (not shown), which can be disposed substantially between the housing 380 and the blocks 410, 420, 430, and 440 and which can be configured to store potential energy for moving the tube set 305 from the initial predetermined position through the other predetermined positions, deploying the closure element 500, and/or activating the locator release system 490. The energy-storing element can be configured store the potential energy when the tube set 305 is in the initial predetermined position and to release the potential energy, when activated, such that the tube set 305 travels through the predetermined positions at a substantially constant and continuous rate. For example, the energy-storing element can include one or more springs (not shown). Each of the springs can be in a compressed state when the tube set 305 is in the initial predetermined position and released from the compressed state when the switching system 450 of the triggering system 400 is activated.

A. Distal End Flexibility

In one embodiment, the closure device includes a flexible distal portion, which is flexible from the distal tip to a predefined location on the shaft. The flexibility of the distal portion of the closure device enables the locator to be selectively bent around corners or directed through intersections of the body lumen during placement of the tip of the closure device. The flexible distal portion also allow the tip to be inserted into the fistula that can be at an angle compared to the body lumen, which can allow the tip to be directed at an angle with respect to the shaft, fistula, and body lumen, such as from 0 to 180 degrees. However, the flexibility can be controlled to be any angle from the shaft that allows the tip, and thereby the closure element to be deployed to close the fistula. This can include flexibility that allows for the tip to be inserted into or through the fistula so that the locator can locate a surface of the fistula and so that the closure element can be applied to close the fistula as shown herein. Often, the closure device will be delivered through a body lumen in which the fistula is located so that the fistula opening and/or fistula conduit is 120 degrees or less with respect to the shaft, which can be less than 90 degrees or less than 45 degrees. Also, the closure device can be delivered through the fistula. Thus, the flexibility allows the tip to be inserted into the fistula in order for the closure element to gather the tissue defining the fistula and pull the tissue together to close the fistula.

For example, trachea-esophageal fistula, which is not close to the mouth opening, requires navigation over the tongue and down through the back of the throat into either the airway or the esophagus. Such delivery requires flexibility, especially when the fistula is perpendicular or at an angle from 90 degrees to 180 degrees with respect to the route of delivery. As such, the distal end of the shaft can bend to an angle of up to about 45 degrees, up to about 90 degrees, up to about 120 degrees, and up to about 180 degrees, which enables the tip to be inserted into fistula at any angle.

B. Shaft Diameter

In one embodiment, the closure device has an outer diameter that is larger than a percutaneous incision for the placement of a standard catheter, such as those used in an arteriotomy. Previous medical devices for closing incisions in blood vessels after a catheter procedure have small dimensions so as to fit through the smallest incisions possible. However, the closure device of the present invention can be sized much larger when delivered through a body lumen that opens to the outside environment, such as through the mouth, nostrils, anus, vagina, and urethra, instead of being delivered through an incision. Often, incisions and catheter diameters have a circumference of about 13.56 mm, which is commonly referred to as 13F through about 1.56 mm, which is commonly referred to as 11F. The outer diameter of the closure device can be configured much larger because of the site of entry into the human body; however, smaller diameters may be employed in some instances. For example, the outer diameter of the shaft and/or carrier assembly can from about 0.2 cm to about 1 cm, more preferably from about 0.3 cm to about 0.75, and most preferably from about 0.4 cm to about 0.6 cm, or larger than about 0.17 inches.

In another example, the outer dimension (e.g., outer diameter) of a closure device in accordance with the present invention can be larger than about 0.17 inches, more preferably larger than about 0.2 inches, and the dimension can be larger than about 0.50 inches, about 0.75 inches, and about 1 inch in some instances, such as for closing a fistula in the colon, vagina, and esophagus. This can allow for the closure element to be retained in the garage at an angle other than congruent with the longitudinal axis of the garage and retaining portion of the shaft. Accordingly, the closure element can be retained in the garage at an angle from the longitudinal axis of from about 0 to about 45 degrees, about 45 degrees to about 90 degrees, about 90 degrees to about 120 degrees, and about 120 degrees to about 180 degrees such that the tines are directed proximally rather then distally as described in more detail herein.

C. Shaft Length

In one embodiment, the shaft of the closure device has a length to be delivered into a normal body opening to the site of the fistula. This can allow for the medical device to be extremely elongate in a length similar to a catheter. Previous medical devices for closing incisions in blood vessels after a catheter procedure have relatively short lengths because they are utilized in a manner that delivers the tip through an incision in the skin and tissue directly outward from the incision in the blood vessel into which the catheter has been deployed. Traversing through the skin and underlying tissue to a blood vessel that receives a catheter requires a length much shorter than the length needed for a closure device of the present invention to be delivered into a normal body opening, through the connecting body lumen or conduit, and into the fistula in a manner that allows for a closure element to be applied to close the fistula. Accordingly, the length can be longer than about 5 cm, between about 10 cm to about 200 cm, more preferably about 20 cm to about 150 cm, and most preferably about 30 cm to about 100 cm. Also, the length of the shaft can be tailored for the type of fistula to be closed, which allows for the length to be sufficient for treating a specific fistula, such as those recited herein.

D. Locator

In one embodiment, the locator of the closure device has a length sufficient to be passed through the fistula canal from one opening to the opposite opening. Normally, the fistula is formed by the tissue between adjacent body lumen, organs, or the like, which forms a fistula canal having a length much longer than the thickness of a blood vessel. The length of the fistula canal can be traversed with a locator having a length sufficient to be passed through the fistula canal so that the locator wings can contact tissue opposite from the opening in which the distal end of the closure element applier is disposed. Previous medical devices for closing incisions in blood vessels after a catheter procedure have relatively short locator lengths because the locator only has to be passed through the thickness of a blood vessel, which is a relatively short distance.

In some instances, traversing through the fistula canal can require a locator length much longer than previous locators configured for closing a hole in a blood vessel. Accordingly, the length of the locator of the present invention can be at least about 0.25 cm, between about 0.3 cm to about 3 cm, more preferably about 0.4 cm to about 2 cm, and most preferably about 0.5 cm to about 1 cm. Also, the length of the shaft can be tailored for the type of fistula to be closed.

In one embodiment, the locator wings of the locator can be of a sufficient size to contact tissue of the fistula to allow for identification of the location of the tip of the closure device with respect to the fistula. Previous medical devices for closing incisions in blood vessels after a catheter procedure have locator wings of the locator with smaller dimensions because they only flair large enough to contact the tissue surrounding the opening of the incision in the blood vessel, which is usually as small as possible. However, the dimension of the flared locator wings of the present invention can be sized much larger because the size of a fistula may be larger, irregular, and more difficult to locate than a controlled incision. The present invention provides locator wings that can flare to a diameter larger than about 0.25 cm, between about 0.3 cm to about 5 cm, more preferably about 0.4 cm to about 2.5 cm, and most preferably about 0.5 cm to about 1 cm.

Of course, the sizes (e.g., lengths and diameters) of the shaft, locator, locator wings, and the like can be configured to be larger or smaller depending on the size of the fistula and its location in the body. For example, the sizes can allow for a working channel to be disposed internally of the locator assembly, where channel can have a size sufficient for passing wires therethrough, such as a guide wire.

In one embodiment, the medical device is configured such that the distal portion of the shaft can be controlled for placement of the tip with respect to the fistula so that the closure element can be deployed in order to close the fistula. This can include the distal portion be sufficiently flexible and/or controllable to negotiate through a body lumen and to turn into a fistula opening. The distal portion (e.g., tip) of the medical device of the present invention can be delivered to the fistula in a manner that any medical device, such as a catheter or endoscope, is delivered to a site within a body of a subject. The configurations, components, equipment, and techniques for the delivery of catheters, endoscopes, and the like to specific sites within the body of a subject can be employed for delivering the tip of the medical device to a fistula. This can include the use of guidewires, delivery catheters, fluoroscopy, endoscopes, scopes, combinations thereof, and the like. For example, a guidewire can be delivered to the fistula as is commonly performed, and the medical device is delivered to the fistula by being directed over the guidewire, and the guidewire is removed at some point, such as before or during deployment of the closure element into the tissue of the fistula. In another example, the distal portion of the medical device is delivered to the fistula by direct visual control or with fluoroscopy, where the medical device includes a controller that controls the deflection of the tip during delivery to the fistula and within the fistula. In another example, the medical device is associated with or included with an endoscope, and the endoscope is delivered to the fistula to deliver the distal portion and closure element to the appropriate position. Also, the distal tip of the medical device can be delivered to a fistula by controlling bending members and bending components as described herein that selectively bend the tip to point in a radial or lateral direction compared to the axis or longitudinal direction of the medical device.

The medical device can include a tip deflection controller system that includes a controller that can move the tip in the directions described herein during placement of the tip of the closure element applier to and/or within the fistula. A multidirectional controller, such as those used in the delivery of catheters, can be used to deflect the tip any one direction by at least one bending member (e.g., rod, tube, wire, etc.) and in the opposite direction within the same plane by a second bending member (e.g., rod, tube, wire, etc). The tip deflection controller system can actuate bending members as described in or similar to FIGS. 4A-4C and FIGS. 5D-5E. Any number of bending member can be used to provide for multiple angles of deflection. For example of deflection in opposite directions, the bending members extend into opposing off-axis lumens within the tip section of the closure element applier. So that the tip section can bend in both directions in the same plane, the puller wires and their associated lumens must be located along a diameter of the tip section.

For example, U.S. Pat. No. 6,210,407, the disclosure of which is incorporated herein by reference, is directed to a bi-directional catheter comprising two puller wires and a control handle having at least two moveable members longitudinally movable between first and second positions. The same principle, components, and operation can be applied to the medical device of the present invention and any number of pull wires (e.g., bending member) can be used for multiple planes of deflection. The proximal end of each puller wire is connected to an associated movable member of the control handle. Proximal movement of a movable member relative to the shaft and carrier assembly results in proximal movement of the puller wire associated with that movable member relative to the shaft, and thus deflection of the tip section in the direction of the lumen in which that puller wire extends.

In another example, U.S. Pat. No. 6,171,277, the disclosure of which is incorporated herein by specific reference, is directed to a bidirectional steerable catheter having a control handle that houses a generally-circular spur gear and a pair of spaced apart rack gears. Each rack gear is longitudinally movable between first and second positions, whereby proximal movement of one rack gear results in rotational movement of the spur gear, and correspondingly distal movement of the other rack gear. Two puller wires extend from the control handle whose the distal ends are fixedly attached to the tip section, and whose proximal ends are each anchored to a separate associated rack gear in the control handle. Proximal movement of a rack gear and its associated puller wire relative to the catheter body results in deflection of the tip section in the direction of the off axis lumen into which that puller wire extends.

In another example, U.S. Pat. No. 6,198,974, the disclosure of which is incorporated herein by specific reference, is directed to a bi-directional catheter comprising a control handle. At their proximal ends, two pairs of puller wires are attached to movable pistons in the control handle. Each piston is controlled by an operator using a slidable button fixedly attached to each piston. Movement of selected buttons results in deflection of the tip section into a generally planar "U"- or "S"-shaped curve In another example, U.S. Pat. No. 5,891,088, the disclosure of which is incorporated herein by specific reference, is directed to a steering assembly with asymmetric left and right curve configurations. Proximal ends of left and right steering wires are adjustably attached to a rotatable cam housed in a control handle. The rotatable cam has first and second cam surfaces which may be configured differently from each other to accomplish asymmetric steering.

In another example, the shaft has an elongated shaft body, a distal shaft section with first and second diametrically-opposed off-axis lumens, and a control handle which includes a steering assembly having a lever structure carrying a pair of pulleys for simultaneously drawing and releasing corresponding puller wires (e.g., bending members) to deflect the distal section of the shaft. In particular, the pulleys are rotatably mounted on opposing portions of the lever structure such that one pulley is moved distally as the other pulley is moved proximally when the lever structure is rotated. Because each puller wire is trained on a respective pulley, rotation of the lever structure causes the pulley that is moved proximally to draw its puller wire to deflect the tip section in the direction of the off-axis lumen in which that puller wire extends another embodiment, the control handle includes a deflection knob that is rotationally coupled to the lever structure which enables the user to control deflection of the tip section with, preferably, a thumb and an index finger, when grasping the control handle. The closure element applier may also include a tension adjustment mechanism for adjusting the tightness of the deflection knob. Optionally, the adjustment mechanism can include a cap and a dial rotationally coupled to each other, a friction nut, and a screw rotationally coupled to cap, whereby rotation of the dial selectively increases or decreases the frictional bearing on the lever structure The same type of or similar mechanics and components discussed above can be incorporated into the closure element applier so that the tip can be delivered to a fistula and turned to that the tip can be directed into or even inserted into the fistula. With reference to FIGS. 4A-4D, the controller, mechanics, and components described for deflection of the distal end of the shaft, and thereby the locator assembly and carrier assembly, can be included with the housing 380. As such, the various elongate members can represent members that are actuated in order to deflect or bend the distal end and tip in a desired direction and in a desired angle. Also, the controllers described herein or others well known in the art can be configured as distal end and/or tip deflection controllers that are operated in order to induce the components to bend the distal end and/or tip as described.

In one embodiment, the actuators for actuating the medical device can be configured in any manner that allows for operation of the medical device as described herein, which include deliver of the distal portion of the medical device to the fistula with the tip being disposed in a position suitable for deploying the closure element into the tissue adjacent to the fistula so as to close the fistula. As such, the actuators can be triggers, knobs, wheels, buttons, levers, switches, and the like. This can allow for any type of actuator to be included in the medical device to operate the different components of the medical device, which includes: maneuvering the tip of the shaft; retraction of the garage; movement of the pusher, carrier, cover, support, and other members associated with retention and deployment of the closure element; deployment of the closure element; operation of the locator, including insertion into the fistula and expansion of the wings and identification of the fistula location; combinations thereof, and the like.

III. Closure Element

A closure element in accordance with the present invention can have a variety of shapes, sizes, and modes of operation. A star closure element or circular closure element with a central lumen and tines pointing toward the lumen can be configured for being disposed on a carrier member can be convenient for storage in the garage, and for being delivered into tissue for fistula repair. The closure element can be similar in form and function to closure elements used for closing incisions in blood vessels. Such a closure element can be configured to be retained within the garage in an orientation to optimize space and deployment potential and efficacy, and can be configured for automatically changing to an orientation that grabs an optimum amount of tissue before reverting to the normal or set orientation that pulls the grabbed tissue together to close the fistula. The closure element can also be configured to flare to a larger diameter during the process of changing from the retained or delivery orientation to the orientation for penetrating and grabbing tissue. Additionally, various materials can be used for a closure element that has the functionality and characteristics as described herein. Moreover, the closure element can be coated with a polymer/drug coating so that a drug can aid in closing and sealing the fistula. Also, a drug can be used for treating complications or infections associated with fistulas or the process of closing the fistula.

Figure 6A:
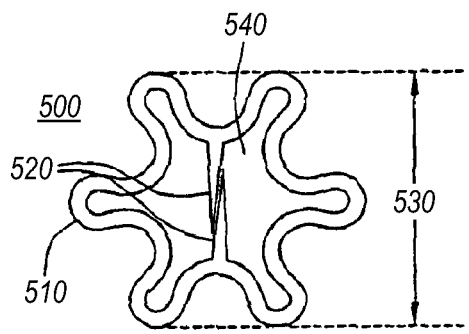
FIG. 6A illustrates a top view of a closure element in a natural, planar configuration and with a natural cross-section for use with the apparatus of FIG. 1.
Figure 6B:
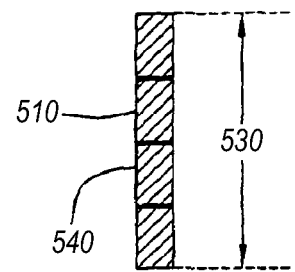
FIG. 6B illustrates a side view of the closure element of FIG. 6A.
Figure 6C:
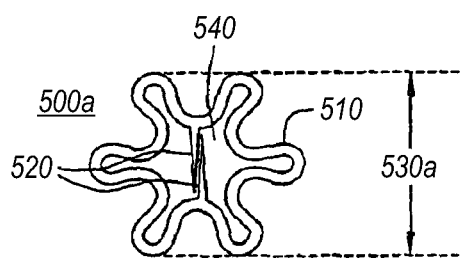
FIG. 6C illustrates a top view of the closure element of FIGS. 6A-6B after a natural cross-section of the closure element has been reduced.
Figure 6D:
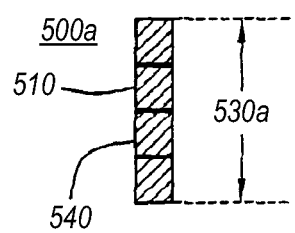
FIG. 6D illustrates a side view of the reduced closure element of FIG. 6C.
Figure 6E:
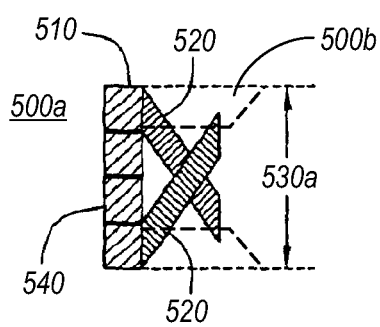
FIG. 6E illustrates a side view of the reduced closure element of FIGS. 6C-6D as the reduced closure element transitions from the natural, planar configuration to a tubular configuration.
Figure 6F:
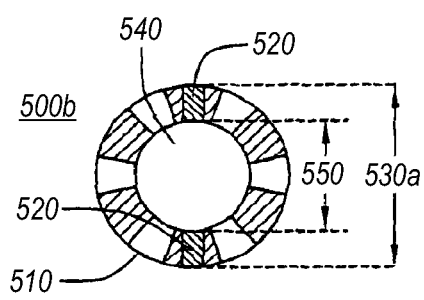
FIG. 6F illustrates a bottom view of the closure element of FIGS. 6C-6D upon completing the transition from the natural, planar configuration to a substantially tubular configuration.
Figure 6G:
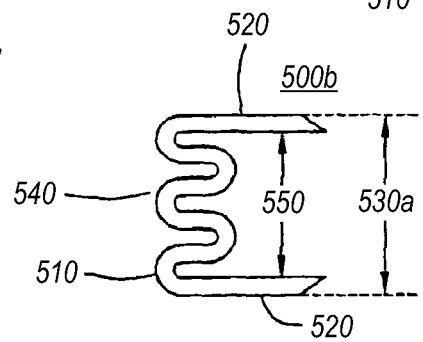
FIG. 6G illustrates a side view of the closure element of FIG. 6F.
Figure 6H:
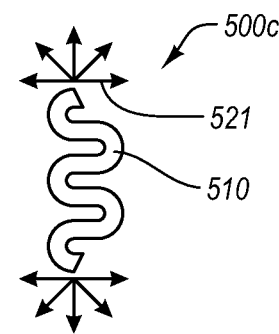
FIG. 6H illustrates a side view of the closure element with the tines at various angles.

FIGS. 6A-6G illustrate one embodiment of a closure element (also referred to herein as a "star closure element") 500 in accordance with the present invention. The closure element 500 can have a generally annular-shape body 510 (shown in FIG. 6A-6B) defining a channel 540 and one or more barbs and/or tines 520 (shown in FIGS. 6A-6B) for receiving and engaging tissue adjacent or within a fistula. While only two tines 520 are shown, any number of tines can be included in the closure element. Although the closure element 500 has a natural shape and size that is set as a memory shape, the closure element 500 can be deformed into other shapes and sizes, as desired, and is configured to return to the natural shape and size when released. For example, the closure element 500 can have a natural, planar configuration with opposing tines 520 and a natural cross-section 530 as shown in FIGS. 6A-6B. The natural cross-section 530 of the closure element 500 can be reduced to form a reduced closure element 500a that has a natural, planar configuration with opposing tines 520 and a reduced cross-section 530a as shown in FIGS. 6C-6D. By rotating the opposing tines 520 axially as shown in FIG. 6E, the reduced closure element 500a can be further deformed to form a substantially tubular closure element 500b (shown by dashed lines in FIG. 6E and shown along the central axis in FIG. 6F) having the reduced cross-section 530a and aperture diameter 550 as well as being in a substantially tubular configuration with the tines 520 in an axial configuration. FIG. 6G illustrates a side profile of the closure element 500b in the substantially tubular configuration. FIG. 6H illustrates a side profile of the closure element 500c in which the body is in the substantially tubular configuration; however, the tines 521 are directed at any one of various angles from 0 degree (distally) to 180 degrees (proximally).

The closure element can have any number of tines. The tines can be equal in length or some can be longer than others.

As shown in FIGS. 1G-1H, the closure element can be a helical or wound wire or spring. The closure element can be configured to be similar to an unwound spring so as to be threaded through the tissue around the fistula canal.

Being configured to draw the tissue surrounding a fistula or within a fistula together so as to be substantially close, the closure element 500 can be formed from any suitable material, including any biodegradable material, any shape memory alloy, such as alloys of nickel-titanium, or any combination thereof. Additionally, it is contemplated that the closure element may be coated with a beneficial agent or be constructed as a composite, wherein one component of the composite would be a beneficial agent. As desired, the closure element 500 may further include radiopaque markers (not shown) or may be wholly or partially formed from a radiopaque material to facilitate observation of the closure element 500 using fluoroscopy or other imaging systems. Exemplary embodiments of a closure element are disclosed in U.S. Pat. Nos. 6,197,042, and 6,623,510, and in co-pending application Ser. Nos. 09/546,998, 09/610,238, and 10/081,726, which are expressly incorporated herein by reference.

In one embodiment, the closure element is configured to flare in an amount sufficient so that the times are capable of penetrating into the tissue defining the fistula. Accordingly, the closure element and tines are configured to flare to a maximum size and/or diameter during deployment so as to maximize the amount of tissue grabbed by the tines and drawn inward to close the fistula. This can include when the closure element is applied to as shown in the FIGS. 1A-1I. The closure element is dimensioned so as to be retained and/or deployed in a manner that flares and extends the tines further outwardly from the fistula opening and/or into the tissue around the fistula opening, which allows for more tissue to be grabbed and pulled together. The present invention provides for the closure element to flare to a diameter sufficient to close a fistula. Since fistulas can vary greatly in the diameter of the opening, the closure elements correspondingly vary so as to be capable of penetrating tissue surrounding the fistula opening. Also, the tines can vary in size with some being larger than others. The closure element diameter and/or tines allow for more tissue to be pulled together and are suitable for closing fistulas without causing more trauma from larger incisions when the closure device is delivered through a natural opening.

In one embodiment, the closure element is configured to extend the tines further outward during deployment before turning and penetrating into the tissue. With respect to the longitudinal axis of the garage, the tines are directed radially away from the axis to form a larger and/or maximum diameter before turning and penetrating into the tissue surrounding the opening of the fistula. The superelastic property of the closure element allows for such a configuration and function during deployment and closure of the fistula, which can be likened to the closure element body and tines being more flat and extending perpendicularly (or angle between 45 degrees to 90 degrees) before turning inwardly to a more tubular shape, and then to the closed and natural shape with the tines pointing more inwardly. As such, the tines would make substantially a 90 degree turn during the deployment into the tissue to close the fistula.

In one embodiment, the closure element body and/or tines (e.g., extended tines) have barbs, hooks, spikes, prongs, protrusions, roughened surfaces, and the like in order to increase the efficiency of tissue contact and grab. As such, the closure element has increased contact points for increasing the contact with the tissue during deployment.

FIGS. 7A-7B illustrate an embodiment of a collapsible tubular closure element 560. As shown in the tubular orientation of FIG. 7A, the closure element 560a includes a tubular body 562 that is defined by body elements 564 that intersect at various locations to leave a plurality of apertures 566 disposed therebetween. The body 562 includes a plurality of tissue-grabbing members 568 disposed thereon. The tissue-grabbing members 568 can be tines, spikes, blades, hooks, barbs, claws, and the like that are configured to penetrate and grab skin. FIG. 7B shows the closure element 560b in the collapsed orientation. Such a closure element 560 can be utilized substantially as described herein, and the closure element applier can be modified to accommodate the tubular closure element 560 for delivery and deployment into a fistula. The tubular closure element 560 can be advantageous for being inserted into the fistula canal and then being released which causes the body 562 to revert to the collapsed orientation which is substantially flat. The collapsed orientation provides the apertures 566 for the tissue to grow between in order to repair the fistula. Also, the tubular closure element 560 can be utilized with or without a locator.

Additionally, the collapsible tubular closure element 560 can be configured to be substantially similar to a stent having tissue-grabbing members 568; however, it is deployed in the expanded orientation into the fistula and then collapses to a narrower tube to pull the fistula together. Accordingly, the collapsible tubular closure element 560 can function as an anti-stent by operating in the opposite manner of a stent.

FIGS. 8A-8B illustrate an embodiment of a self-rolling closure element 570. FIG. 8A shows the self-rolling closure element 570a in a substantially flat orientation. The self-rolling closure element 570a is shown to have a body 572 with a plurality of tissue-grabbing members 574 disposed thereon. When the self-rolling closure element 570a is inserted into a fistula, it transformed from being substantially flat to a rolled closure element 570b as shown in FIG. 8B. Such a closure element 570 can be utilized substantially as described herein, and the closure element applier can be modified to accommodate the self-rolling closure element 570 for delivery and deployment into a fistula. The self-rolling closure element 570 can be advantageous for being inserted into the fistula canal and then being released which causes the body 572 to revert to the rolled orientation so as to pull the tissue of the fistula together. The self-rolling closure element 570 can include apertures 576 for the tissue to grow between in order to repair the fistula. Also, the closure element 570 can be utilized with or without a locator. The self-rolling closure element 570 can also be configured in the opposite manner in which it is delivered rolled as shown in FIG. 8B and then it unrolls to the orientation shown in FIG. 8A in order to repair the fistula. In any event, the change in orientation allows for the tissue-grabbing members 574 to pull the tissue of the fistula together.

FIGS. 9A-9B illustrate a side view an embodiment of a reverse closure element 580. FIG. 9A shows the reverse closure element 580a in a substantially an "S" orientation. The reverse closure element 580a is shown to have a body 582 with a first tissue-grabbing member 584a disposed thereon and an oppositely disposed second tissue-grabbing member 584b. When the reverse closure element 580a is inserted into a fistula, it transformed from being substantially "S" shaped to substantially an "8" shape 570b (FIG. 9B) with the tissue grabbing members 584a-b passing the body in order to grab and pull the tissue of the fistula closed. Such a closure element 580 can be utilized substantially as described herein, and the closure element applier can be modified to accommodate the reverse closure element 580 for delivery and deployment into a fistula. The reverse closure element 580 can be advantageous for being inserted into the fistula canal and then being released which causes the body 582 to revert to the substantially "8" shaped closure element 580b in a manner that pulls the tissue from opposite openings of the fistula together. The closure element 580 an also pull opposite portions of tissue from within the fistula canal. The reverse closure element 580 can be annular, have a plurality of reverse tissue-grabbing members 584a-b, be flat, or other similar configuration. Also, the closure element 580 can be utilized with or without a locator.

FIGS. 10A-10B illustrate a side view an embodiment of a clam closure element 590. FIG. 10A shows the clam closure element 590a in a substantially an open clam orientation. The clam closure element 590a is shown to have two opposite body portions 592a-b, each body portion having a corresponding tissue-grabbing member 594a-b disposed thereon. When the clam closure element 590a is inserted into a fistula, it transformed from being in a substantially open clam shape to substantially a closed clam shape 590b (FIG. 9B) with the tissue grabbing members 594a-b passing by each other in order to grab and pull the tissue of the fistula closed. During deployment, the claim closure element 590 passes through substantially a "C" shape. Such a closure element 590 can be utilized substantially as described herein, and the closure element applier can be modified to accommodate the clam closure element 580 for delivery and deployment into a fistula. The clam closure element 580 can be advantageous for being inserted into the fistula canal and then being released which causes the body segments 592a-b to revert to the substantially closed clam shaped closure element 580b in a manner that pulls the tissue from opposite openings of the fistula together. It can also be used applied to the tissue around the opening of the fistula. The clam closure element 590 can be annular, have a plurality of tissue-grabbing members 594a- b, be flat, or other similar configuration. Also, the closure element 590 can be utilized with or without a locator.

In one embodiment, the closure element has increased flexibility and/or decreased mechanical strength with respect to the relaxed orientation due to the fistula not being a high pressure system. Previous closure elements employed in closing incisions formed in blood vessels have been designed with decreased flexibly and/or increased mechanical strength due to the blood vessel being a high pressure network with blood pressure against the arterial walls. Accordingly, closure elements configured for closing an incision in a blood vessel had to be configured to resist blood pressure. The closure elements of the present invention can be configured for application in a system with much less pressure requirements. That is, a closure element configured for closing a fistula does not have the same strength and mechanical requirements for closing an incision in a blood vessel. Thus, the closure elements for closing a fistula can be comparatively more flexible and have decreased mechanical strength.

In one embodiment, the closure element can be prepared from a biodegradable material. This allows for the closure element to be degraded over time after being inserted into the body to close the fistula. Biodegradable polymers can be formed into closure elements to have the properties described herein. The list of biocompatible polymers includes such biodegradable polymers that would be suitable for preparing a biodegradable closure element of the present invention.

In one embodiment, the closure element is coated with an active pharmaceutical ingredient with or without a polymeric carrier. The active pharmaceutical ingredient can be any drug; however, it is preferable for it to increase tissue growth The polymeric coating and drug are configured to cooperate so as to form a diffusion pathway (e.g., lipophilic, hydrophilic, and/or amphipathic) with tissue when the closure element penetrates the tissue and closes the fistula. This allows for the drug to preferentially diffuse into the tissue instead of into a body fluid passing over the closure element.

A biocompatible closure element or polymeric coating on the closure element can also be provided so that the closure element can be loaded with and deliver beneficial agents or drugs, such as therapeutic agents, pharmaceuticals and radiation therapies. Accordingly, the polymeric closure element and/or coating material can contain a drug or beneficial agent to improve the use of the closure element. Such drugs or beneficial agents can include antithrombotics, anticoagulants, antiplatelet agents, thrombolytics, antiproliferatives, anti-inflammatories, agents that inhibit hyperplasia, inhibitors of smooth muscle proliferation, antibiotics, growth factor inhibitors, or cell adhesion inhibitors, as well as antineoplastics, antimitotics, antifibrins, antioxidants, agents that promote endothelial cell recovery, antiallergic substances, radiopaque agents, viral vectors having beneficial genes, genes, siRNA, antisense compounds, oligionucleotides, cell permeation enhancers, and combinations thereof. Another example of a suitable beneficial agent is described in U.S. Pat. No. 6,015,815 and U.S. Pat. No. 6,329,386 entitled "Tetrazole-containing rapamycin analogs with shortened half-lives", the entireties of which are herein incorporated by reference.

More specific examples of drugs that can be included in the coating of the closure element include any of the following: anti-proliferative/antimitotic agents including natural products such as *vinca* alkaloids (i.e. vinblastine, vincristine, and vinorelbine), paclitaxel, epidipodophyllo-toxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents such as G(GP) II$_b$/III$_a$ inhibitors and vitronectin receptor antagonists; anti-proliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes-dacarbazinine (DTIC); anti-proliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives i.e. aspirin; para-aminophenol derivatives i.e. acetaminophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), everolimus, azathioprine, mycophenolate mofetil); angiogenic agents: vascular endothelial growth factor (VEGF), fibroblast growth factor (FGF); angiotensin receptor blockers; nitric oxide donors; antisense oligionucleotides and combinations thereof; cell cycle inhibitors, mTOR inhibitors, and growth factor receptor signal transduction kinase inhibitors; retenoids; cyclin/CDK inhibitors; HMG co-enzyme reductase inhibitors (statins); and protease inhibitors. Also, it should be recognized that many active agents have multiple pharmaceutical uses other than those specifically recited.

The closure element (i.e., fistula closure element) of the present invention can be made of a variety of biocompatible materials, such as, but not limited to, those materials which are well known in the art of endoprostheses. Generally, the materials for the closure element can be selected according to the structural performance and biological characteristics that are desired, such as superelasticity, flexibility, size, shape, changes in orientation, biodegradability, drug elution, and the like.

In one configuration, the closure element can be made of a single material or of multiple layers, with at least one layer being applied to a primary material. This can include a metal primary material and polymer/drug topcoat or a different metal top layer. The multiple layers can be resiliently flexible materials or rigid and inflexible materials, and selected combinations thereof. For example, materials such as Ti3Al2.5V, Ti6Al4V, 3-2.5Ti, 6-4Ti and platinum may be particularly good choices for adhering to a flexible material, such as, but not limited to, nitinol and providing good crack arresting properties. The use of resiliently flexible materials can provide force-absorbing characteristics, which can also be beneficial for absorbing stress and strains, which may inhibit crack formation at high stress zones. Also, the multiple layers can be useful for applying radiopaque materials. For example, types of materials that are used to make a closure element can be selected so that the closure element is capable of being in a first orientation (e.g., delivery orientation) during placement and capable of transforming to a second orientation (e.g., deploying orientation) when deployed to close the fistula.

Embodiments of the closure element can include a material made from any of a variety of known suitable biocompatible materials, such as a biocompatible shaped memory material (SMM). For example, the SMM can be shaped in a manner that allows for a delivery orientation while within the garage of the shaft of the medical device, but can automatically retain the memory shape of the closure element once deployed from the garage and into the tissue to close the fistula. SMMs have a shape memory effect in which they can be made to remember a particular shape. Once a shape has been remembered, the SMM may be bent out of shape or deformed and then returned to its original shape by unloading from strain or heating. Typically, SMMs can be shape memory alloys (SMA) comprised of metal alloys, or shape memory plastics (SMP) comprised of polymers. The materials can also be referred to as being superelastic.

Usually, an SMA can have an initial shape that can then be configured into a memory shape by heating the SMA and conforming the SMA into the desired memory shape. After the SMA is cooled, the desired memory shape can be retained. This allows for the SMA to be bent, straightened, twisted, compacted, and placed into various contortions by the application of requisite forces; however, after the forces are released, the SMA can be capable of returning to the memory shape. The main types of SMAs are as follows: copper-zinc-aluminium; copper-aluminium-nickel; nickel-titanium (NiTi) alloys known as nitinol; nickel-titanium platinum; nickel-titanium palladium; and cobalt-chromium-nickel alloys or cobalt-chromium-nickel-molybdenum alloys known as elgiloy alloys. The temperatures at which the SMA changes its crystallographic structure are characteristic of the alloy, and can be tuned by varying the elemental ratios or by the conditions of manufacture. This can be used to tune the closure element so that it reverts to the memory shape to close the fistula when deployed at body temperature and when being released from the garage.

For example, the primary material of a closure element can be of a NiTi alloy that forms superelastic nitinol. In the present case, nitinol materials can be trained to remember a certain shape, retained within the garage in the shaft, and then deployed from the garage so that the tines penetrate the tissue as it returns to its trained shape and closes the fistula. Also, additional materials can be added to the nitinol depending on the desired characteristic. The alloy may be utilized having linear elastic properties or non-linear elastic properties.

An SMP is a shape-shifting plastic that can be fashioned into a closure element in accordance with the present invention. Also, it can be beneficial to include at least one layer of an SMA and at least one layer of an SMP to form a multilayered body; however, any appropriate combination of materials can be used to form a multilayered endoprosthesis. When an SMP encounters a temperature above the lowest melting point of the individual polymers, the blend makes a transition to a rubbery state. The elastic modulus can change more than two orders of magnitude across the transition temperature (Ttr). As such, an SMP can formed into a desired shape of an endoprosthesis by heating it above the Ttr, fixing the SMP into the new shape, and cooling the material below Ttr. The SMP can then be arranged into a temporary shape by force, and then resume the memory shape once the force has been applied. Examples of SMPs include, but are not limited to, biodegradable polymers, such as oligo(ε-caprolactone)diol, oligo(ρ-dioxanone)diol, and non-biodegradable polymers such as, polynorborene, polyisoprene, styrene butadiene, polyurethane-based materials, vinyl acetate-polyester-based compounds, and others yet to be determined. As such, any SMP can be used in accordance with the present invention.

A closure element body having at least one layer made of an SMM or suitable superelastic material and other suitable layers can be compressed or restrained in its delivery configuration within the garage, and then deployed into the tissue so that it transforms to the trained shape and closes the fistula.

Also, the closure element can be comprised of a variety of known suitable deformable materials, including stainless steel, silver, platinum, tantalum, palladium, nickel, titanium, nitinol, nitinol having tertiary materials (U.S. 2005/0038500, which is incorporated herein by specific reference), niobium-tantalum alloy optionally doped with a tertiary material (U.S. 2004/0158309, 2007/0276488, and U.S. Ser. No. 12/070,646, which are each incorporated herein by specific reference) cobalt-chromium alloys, or other known biocompatible materials. Such biocompatible materials can include a suitable biocompatible polymer in addition to or in place of a suitable metal. The polymeric closure element can include biodegradable or bioabsorbable materials, which can be either plastically deformable or capable of being set in the deployed configuration.

In one embodiment, the closure element is made from a superelastic alloy such as nickel-titanium or nitinol, and includes a ternary element selected from the group of chemical elements consisting of iridium, platinum, gold, rhenium, tungsten, palladium, rhodium, tantalum, silver, ruthenium, or hafnium. The added ternary element improves the radiopacity of the nitinol closure element. The nitinol closure element has improved radiopacity yet retains its superelastic and shape memory behavior and further maintains a thin body thickness for high flexibility. For example, the closure element according to the present invention has 42.8 atomic percent nickel, 49.7 atomic percent titanium, and 7.5 atomic percent platinum.

In one embodiment, the closure element can be made at least in part of a high strength, low modulus metal alloy comprising Niobium, Tantalum, and at least one element selected from the group consisting of Zirconium, Tungsten, and Molybdenum. The closure element according to the present invention provide superior characteristics with regard to bio-compatibility, radio-opacity and MRI compatibility.

In one embodiment, the closure element can be made from or be coated with a biocompatible polymer. Examples of such biocompatible polymeric materials can include hydrophilic polymer, hydrophobic polymer biodegradable polymers, bioabsorbable polymers, and monomers thereof. Examples of such polymers can include nylons, poly(alpha-hydroxy esters), polylactic acids, polylactides, poly-L-lactide, poly-DL-lactide, poly-L-lactide-co-DL-lactide, polyglycolic acids, polyglycolide, polylactic-co-glycolic acids, polyglycolide-co-lactide, polyglycolide-co-DL-lactide, polyglycolide-co-L-lactide, polyanhydrides, polyanhydride-co-imides, polyesters, polyorthoesters, polycaprolactones, polyesters, polyanydrides, polyphosphazenes, polyester amides, polyester urethanes, polycarbonates, polytrimethylene carbonates, polyglycolide-co-trimethylene carbonates, poly(PBA-carbonates), polyfumarates, polypropylene fumarate, poly(p-dioxanone), polyhydroxyalkanoates, polyamino acids, poly-L-tyro sines, poly(beta-hydroxybutyrate), polyhydroxybutyrate-hydroxyvaleric acids, polyethylenes, polypropylenes, polyaliphatics, polyvinylalcohols, polyvinylacetates, hydrophobic/hydrophilic copolymers, alkylvinylalcohol copolymers, ethylenevinylalcohol copolymers (EVAL), propylenevinylalcohol copolymers, polyvinylpyrrolidone (PVP), combinations thereof, polymers having monomers thereof, or the like.

IV. Endoscope Closure Element Applier

In one embodiment, the medical device of the present invention is associated with or included as part of an endoscope. This includes the closure element applier and components there being coupled with an endoscope so as to be integrated therewith. Alternatively, the closure element applier medical device can be coupled to or operated with an endoscope such that the scope and closure element applier are separate, but couplable.

The medical device can be associated with or included with an endoscope, and the endoscope is delivered to the fistula to deliver the distal portion and closure element to the appropriate position. Many endoscopes include a working channel or lumen disposed in the center of the scope and extending from the proximal end to the distal end. Such an endoscope can be utilized and/or configured for receiving the closure element applier within the working channel so that it can be delivered to the fistula.

Figure 11:
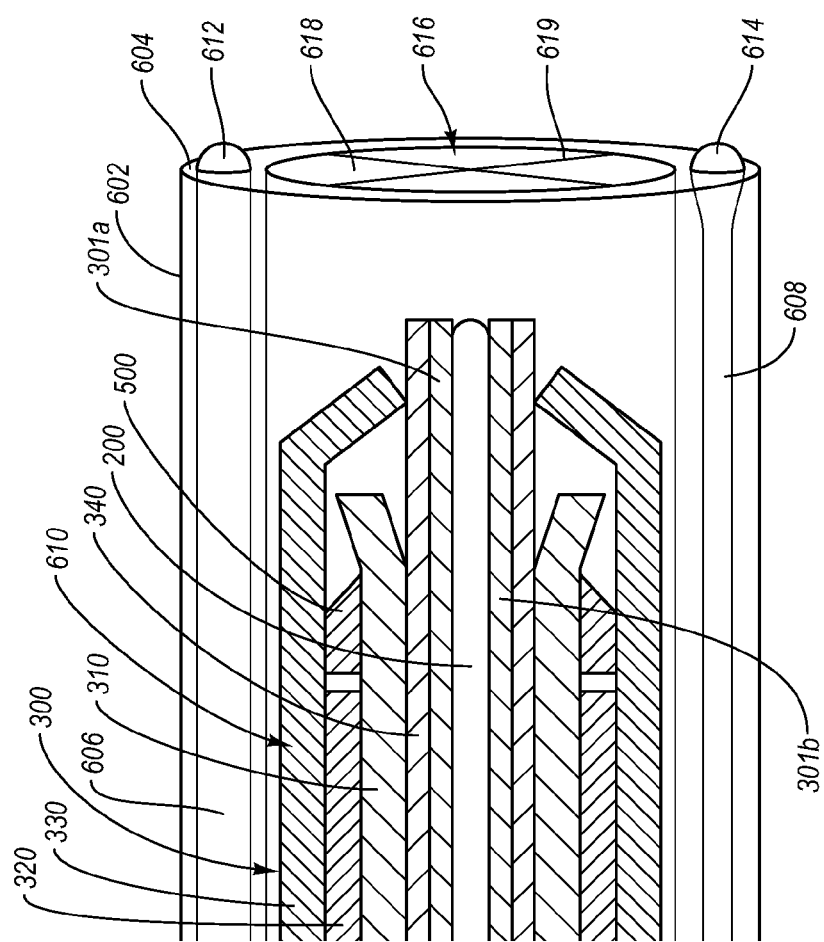
FIG. 11 illustrates an endoscope having medial device components for repairing a fistula.

FIG. 11 is a cutaway side view illustrating an embodiment of an endoscope closure element applier 600, which includes endoscope components and closure element components. As shown, the endoscope closure element applier 600 can have a tubular body 602 with a distal end 604. The tubular body 602 can include a camera lumen 606 that contains a camera 612 at the distal end 604 and can include other camera components commonly used in endoscopes. The tubular body 602 can also include a lighting device lumen 608 that contains a lighting device 614 at the distal end 604 and can include other lighting devices commonly used in endoscopes. Additionally, the tubular body 602 can include a closure element applier lumen 610 that contains a carrier assembly 300 containing a closure element 500. The closure element applier lumen 610 can open at the distal end 604 at a distal opening 616. The distal opening can include an opening member 618 that can remain closed until the closure element 500 is ready to be deployed to close the fistula. The opening member 618 can optionally include slits 619 that allow for the carrier assembly 300 to pass therethrough so that the closure element 500 can be deployed. Also, the carrier assembly 300 can include the features and components as described herein.

In one embodiment, an endoscope includes components of a closure element applier so as to be a combination medical device having endoscopic components and closure element applier components. In such an embodiment, the endoscope portion can be utilized for delivery of the closure element applier portion to the fistula. The closure element applier can then be utilized as described herein for deploying a closure element into the tissue so as to close the fistula. Alternatively, a closure element applier includes components of an endoscope. For example, the locator assembly 200 can include the locator tip 200 having a portion (not shown) that functions as the optical portion of an endoscope. Accordingly, the tip 200 and distal portion 210b of the locator assembly can be configured to operate as an endoscope, such as is shown in FIGS. 2A-2C.

In one embodiment, the medical device of the present invention is configured to be delivered through the lumen of an endoscope. In this embodiment, the endoscope is delivered to the fistula as endoscopes are normally utilized, and then the closure element applier is delivered through the lumen of the endoscope to the fistula such that the closure element can be deployed to close the fistula. For example, a guidewire can be delivered to the fistula using standard equipment and techniques, and the endoscope is delivered to the fistula by being passed over the guidewire, which is disposed within the working channel of the endoscope. When the distal end of the endoscope is appropriately positioned with respect to the fistula, the guidewire is retracted through the working channel and the closure element applier is traversed through the working channel so as to be positioned appropriately so that the closure element can be applied to close the fistula.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope. All references recited herein are incorporated herein by specific reference in their entirety.

What is claimed is:

1. A tissue closure system for engaging with tissue within or adjacent to a fistula to close and repair the fistula, the tissue closure system comprising:
   a tissue closure element comprising:
      an elongate body portion, the elongate body portion including an inflection portion;
      a first tissue-grabbing member joined to the elongate body portion;
      a second tissue-grabbing member joined to the elongate body portion and disposed opposite the first tissue-grabbing member; and
      wherein the first and second tissue-grabbing members move about the inflection portion as the tissue closure element moves from an expanded configuration toward a closed configuration, wherein at least a portion of the first tissue-grabbing member overlaps a portion of the elongate body portion when the tissue closure element moves from the expanded configuration toward the closed configuration, wherein the tissue closure element is substantially "S"-shaped in the expanded configuration and moves toward an "8"-shape as it moves toward the closed configuration, such that the first and second tissue-grabbing members move toward the elongate body as the tissue closure element moves from the expanded configuration toward the closed configuration;
   a carrier assembly having a garage for retaining the tissue closure element, said carrier assembly having a flexible portion being selectively controlled to bend to direct the tissue closure element toward tissue within or near the fistula, the flexible portion selectively controllable to bend to an angle of at least about 45 degrees;

a carrier assembly controller system operatively coupled to the flexible portion of the carrier assembly for controlling the delivery of the carrier assembly to the fistula; and a closure element deployment controller system operatively coupled to the carrier assembly for deploying the tissue closure element to the tissue to repair the fistula, the tissue closure element disposed within the garage and oriented such that both the first and second tissue grabbing members are both oriented toward the tissue.

2. The tissue closure system of claim 1, wherein at least a portion of the first tissue-grabbing member is adjacent to at least a portion of the second tissue-grabbing member in the closed configuration.

3. The tissue closure system of claim 1, wherein an arcuate path of the first tissue-grabbing member while passing from the expanded configuration toward the closed configuration is in the same rotational direction as an arcuate path of the second tissue-grabbing member while passing from the expanded configuration toward the closed configuration.

4. The tissue closure system of claim 1, wherein an arcuate path of the first tissue-grabbing member while passing from the expanded configuration toward the closed configuration is in the opposite rotational direction as an arcuate path of the second tissue-grabbing member while passing from the expanded configuration toward the closed configuration.

5. The tissue closure system of claim 1, wherein the tissue closure element is prepared from a biodegradable material.

6. The tissue closure system of claim 1, wherein the tissue closure element is treated with an active pharmaceutical ingredient.

7. The tissue closure system of claim 1, wherein the tissue closure element is configured with greater flexibility or decreased mechanical strength when in a deployed configuration relative to the flexibility or mechanical strength of a blood vessel incision closure device configured to resist blood pressure when in a deployed configuration in a blood pressurized blood vessel environment.

8. The tissue closure system of claim 1, further comprising a locator assembly operably coupled to the carrier assembly, the locator assembly being slidable around or through the tissue closure element.

9. The tissue closure system of claim 8, wherein the locator assembly includes a locator, the locator including at least two locator wings.

10. The tissue closure system of claim 8, wherein the locator assembly is configured to collapse and withdraw from the fistula simultaneously as the tissue closure element is deployed.

11. The tissue closure system of claim 1, wherein the carrier assembly includes a carrier member that is bendable from a predeployment configuration to a deployment configuration.

12. The tissue closure system of claim 1, further comprising endoscope components configured such that the medical device is capable of functioning as an endoscope.

13. A method for closing and repairing a fistula, the method comprising:

positioning a tissue closure element near tissue within or adjacent to the fistula with a carrier assembly having a garage for retaining the closure element, the carrier assembly having a flexible portion being selectively controlled to bend to direct the closure element toward tissue within or near the fistula, the tissue closure element disposed within the garage, the tissue closure element comprising:

an elongate body portion, the body portion including an inflection portion;

a first tissue-grabbing member having a tine joined to the elongate body portion;

a second tissue-grabbing member having a tine joined to the elongate body portion and disposed opposite the first tissue-grabbing member;

wherein the first and second tissue grabbing-members are both oriented toward the tissue in the garage, the first and second tissue-grabbing members move about the inflection portion as the tissue closure element moves from an expanded configuration toward a closed configuration, wherein at least a portion of the first tissue-grabbing member overlaps a portion of the elongate body portion when the tissue closure element moves from the expanded configuration toward the closed configuration, wherein the tissue closure element is substantially "S"-shaped in the expanded configuration and moves toward an "8"-shape as it moves toward the closed configuration, such that the first and second tissue-grabbing members move toward the elongate body as the tissue closure element moves from the expanded configuration toward the closed configuration;

moving the tissue closure element from the predeployed configuration into an expanded configuration; and deploying the tissue closure element into tissue within or adjacent to the fistula, the tissue closure element moving toward the closed configuration upon deployment into the tissue to close and repair the fistula.

14. The method of claim 13, wherein at least a portion of the first tissue-grabbing member is adjacent to at least a portion of the second tissue-grabbing member in the closed configuration.

15. The method of claim 13, wherein at least a portion of the first tissue-grabbing member overlaps a portion of the elongate body portion when the tissue closure element moves from the expanded configuration toward the closed configuration.

16. The tissue closure system of claim 1, wherein the first tissue-grabbing member and the second tissue-grabbing member are tines.

17. The tissue closure system of claim 1, wherein the first tissue-grabbing tine and the second tissue-grabbing tine taper to their distal end.

* * * * *